(12) United States Patent
Takemura et al.

(10) Patent No.: US 10,457,779 B2
(45) Date of Patent: Oct. 29, 2019

(54) TETRACARBOXYLIC ACID DIESTER COMPOUND, POLYIMIDE PRECURSOR POLYMER AND METHOD FOR PRODUCING THE SAME, NEGATIVE PHOTOSENSITIVE RESIN COMPOSITION, POSITIVE PHOTOSENSITIVE RESIN COMPOSITION, PATTERNING PROCESS, AND METHOD FOR FORMING CURED FILM

(71) Applicant: SHIN-ETSU CHEMICAL CO., LTD., Tokyo (JP)

(72) Inventors: Katsuya Takemura, Jyoetsu (JP); Hiroyuki Urano, Jyoetsu (JP); Masashi Iio, Jyoetsu (JP); Masayoshi Sagehashi, Jyoetsu (JP); Koji Hasegawa, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/457,493

(22) Filed: Mar. 13, 2017

(65) Prior Publication Data
US 2017/0298186 A1    Oct. 19, 2017

(30) Foreign Application Priority Data
Apr. 19, 2016  (JP) .................................. 2016-83787

(51) Int. Cl.
*G03F 7/023*   (2006.01)
*G03F 7/031*   (2006.01)
(Continued)

(52) U.S. Cl.
CPC .......... *C08G 73/1039* (2013.01); *C07C 69/76* (2013.01); *C07C 69/92* (2013.01); *C08G 73/105* (2013.01); *C08G 73/106* (2013.01); *C08G 73/1007* (2013.01); *C08G 73/1042* (2013.01); *C08G 73/1071* (2013.01); *C08G 73/123* (2013.01); *C08G 73/126* (2013.01); *C09D 179/08* (2013.01); *G03F 7/0045* (2013.01); *G03F 7/0046* (2013.01); *G03F 7/0226* (2013.01); *G03F 7/0233* (2013.01); *G03F 7/031* (2013.01); *G03F 7/037* (2013.01); *G03F 7/038* (2013.01); *G03F 7/039* (2013.01); *G03F 7/0387* (2013.01); *G03F 7/0388* (2013.01);
(Continued)

(58) Field of Classification Search
CPC ...... G03F 7/0233; G03F 7/0226; G03F 7/031; G03F 7/037; G03F 7/038; G03F 7/0387; G03F 7/0388; G03F 7/38; G03F 7/40; C07C 69/76; C07C 69/88; C08G 73/1039; C08G 73/1042; C08G 73/105; C08G 73/106; C08G 73/1071; C08G 73/123; C08G 73/126

USPC ......... 430/165, 191, 192, 193, 281.1, 287.1, 430/325, 326, 330; 528/353; 560/76, 80, 560/87, 95
See application file for complete search history.

(56) References Cited

U.S. PATENT DOCUMENTS 3,957,512 A    5/1976  Kleeberg et al.
6,001,534 A   12/1999  Kato
(Continued)

FOREIGN PATENT DOCUMENTS

JP    S49-115541 A    11/1974
JP    S55-45746 A     3/1980
(Continued)

OTHER PUBLICATIONS

Jul. 4, 2017 Extended Search Report issued in European Patent Application No. 17000643.1.
(Continued)

*Primary Examiner* — John S Chu
(74) *Attorney, Agent, or Firm* — Oliff PLC

(57) ABSTRACT

The present invention provides a tetracarboxylic acid diester compound shown by the following general formula (1),

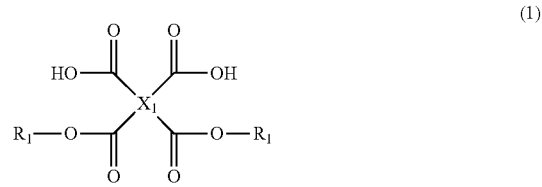

wherein $X_1$ represents a tetravalent organic group; and $R_1$ represents a group shown by the following general formula (2),

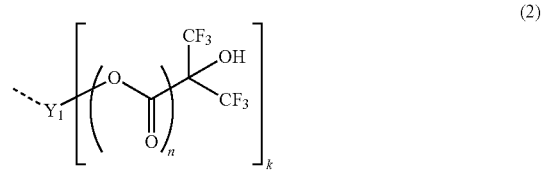

wherein the dotted line represents a bond; $Y_1$ represents an organic group with a valency of k+1; "k" represents 1 or 2; and "n" represents 0 or 1. There can be provided a tetracarboxylic acid diester compound that can give a polyimide precursor polymer soluble in a safe organic solvent widely used as a solvent of a composition and usable as a base resin of a photosensitive resin composition.

18 Claims, No Drawings

(51) Int. Cl.
| | |
|---|---|
| *G03F 7/037* | (2006.01) |
| *G03F 7/038* | (2006.01) |
| *G03F 7/38* | (2006.01) |
| *G03F 7/40* | (2006.01) |
| *C08G 73/10* | (2006.01) |
| *C08G 73/12* | (2006.01) |
| *C07C 69/76* | (2006.01) |
| *C07C 69/88* | (2006.01) |
| *G03F 7/022* | (2006.01) |
| *C07C 69/92* | (2006.01) |
| *G03F 7/004* | (2006.01) |
| *G03F 7/039* | (2006.01) |
| *G03F 7/16* | (2006.01) |
| *G03F 7/20* | (2006.01) |
| *G03F 7/32* | (2006.01) |
| *C09D 179/08* | (2006.01) |

(52) U.S. Cl.
CPC .............. *G03F 7/162* (2013.01); *G03F 7/168* (2013.01); *G03F 7/2037* (2013.01); *G03F 7/322* (2013.01); *G03F 7/38* (2013.01); *G03F 7/40* (2013.01)

(56) References Cited

U.S. PATENT DOCUMENTS

| | | | |
|---|---|---|---|
| 7,851,121 B2* | 12/2010 | Yamanaka | G03F 7/0046 430/191 |
| 9,793,483 B2* | 10/2017 | Uoyama | C09K 11/06 |
| 2009/0263745 A1 | 10/2009 | Sakayori | |
| 2009/0272295 A1 | 11/2009 | Miyazawa et al. | |

FOREIGN PATENT DOCUMENTS

| | | |
|---|---|---|
| JP | 3232022 B2 | 11/2001 |
| JP | 2005-049504 A | 2/2005 |
| JP | 3627488 B2 | 3/2005 |
| JP | 3721768 B2 | 11/2005 |
| JP | 2007-199653 A | 8/2007 |
| JP | 5417623 B2 | 2/2014 |
| KR | 20080056231 | 6/2008 |
| WO | 2013/168675 A1 | 11/2013 |
| WO | 2014/084185 A1 | 6/2014 |

OTHER PUBLICATIONS

Aug. 13, 2018 Office Action issued in Korean Patent Application No. 10-2017-0049942.

* cited by examiner

TETRACARBOXYLIC ACID DIESTER COMPOUND, POLYIMIDE PRECURSOR POLYMER AND METHOD FOR PRODUCING THE SAME, NEGATIVE PHOTOSENSITIVE RESIN COMPOSITION, POSITIVE PHOTOSENSITIVE RESIN COMPOSITION, PATTERNING PROCESS, AND METHOD FOR FORMING CURED FILM

BACKGROUND OF THE INVENTION

Field of the Invention

The present invention relates to a tetracarboxylic acid diester compound useful as a structural unit of a polyimide precursor polymer, a polyimide precursor polymer obtained by using the tetracarboxylic acid diester compound, a method for producing the same, a negative photosensitive resin composition and a positive photosensitive resin composition using the polyimide precursor polymer as their base resin, a patterning process using the negative photosensitive resin composition or the positive photosensitive resin composition, and a method for forming a cured film.

Description of the Related Art

As various electronic devices including a personal computer, a digital camera, and a mobile phone progress toward downsizing and higher performance, requirements are rapidly increasing for further downsizing, thinning, and densifying in semiconductor devices. It is thus desired to develop a photosensitive insulating material that can accommodate an increase in surface area of a substrate for the sake of higher productivity and can form a fine pattern with high aspect ratio on a substrate, in high density mounting technologies including chip size package or chip scale package (CSP) and three-dimensional lamination.

As the photosensitive insulating material capable of forming a pattern on a substrate in the high density mounting technology including three-dimensional lamination, a polyimide film has been used for a top coat or an insulator layer. The polyimide film has attracted attention because of its insulating property, mechanical strength, and adhesiveness to a substrate, and has been still actively developed.

Conventional examples of the photosensitive polyimide material include materials using polyamic acid, which is a precursor of polyimide. For example, there are proposed materials in which a photosensitive group is introduced into a carboxyl group of polyamic acid by an ester bond (Patent Documents 1 and 2). However, these proposed materials require imidization treatment at a high temperature exceeding 300° C. after forming a patterned film to obtain an intended polyimide film. Thus, these materials need to restrict a base substrate and oxidize a copper wiring in order to withstand the high temperature.

To solve such problems, there are proposed photosensitive polyimides using a solvent-soluble resin that has been already imidized to lower the temperature for post-curing (Patent Documents 3, 4, and 5). A negative photosensitive resin composition containing the polyimide described in Patent Document 3 uses N-methyl-2-pyrrolidone (NMP) for development in patterning. However, N-methyl-2-pyrrolidone has a risk of environmental hazard and health hazard, especially aspiration hazard. In particular, N-methyl-2-pyrrolidone is included in SVHC (Substance of Very High Concern) by European REACH (Registration, Evaluation, Authorization and Restriction of Chemicals) regulation. Thus, the use of N-methyl-2-pyrrolidone as a solvent should be avoided as much as possible. Moreover, Patent Document 3 fails to specifically describe the resolution capacity in patterning.

On the other hand, Patent Document 4 describes that an alkaline aqueous solution is used for development in patterning, but a solvent used in this composition is also N-methyl-2-pyrrolidone, which should be avoided for the same reason as above. Moreover, it is known that mechanical strength of a polyimide film is reduced when N-methyl-2-pyrrolidone is used as a solvent of its photosensitive resin composition. N-methyl-2-pyrrolidone is a solvent having a high boiling point and thus can remain even after drying a polyimide film and a pattern. This residue reduces mechanical strength of the polyimide film. For the foregoing reasons, the use of N-methyl-2-pyrrolidone as the solvent of the photosensitive resin composition should be avoided.

A photosensitive resin composition proposed in Patent Document 5 uses a base resin that has been already imidized for curing at low temperature. This composition contains cyclopentanone as a solvent and utilizes an alkaline aqueous solution for development process, and thus the use of N-methyl-2-pyrrolidone is avoided. However, its resolution capacity still should be improved. More specifically, patterning using the photosensitive resin composition described in Patent Document 5 is performed with an ultrathin film, and the size of a resolved pattern is large. This insufficient resolution capacity is due to a polyimide resin used as the base resin disclosed in Patent Document 5, which has poor solubility in an alkaline aqueous solution used as the developer.

In practice, with respect to the resolution capacity of the photosensitive insulating material recently required in the high density mounting technology including three-dimensional lamination, a pattern to be formed requires an aspect ratio (final film thickness (or pattern height)/pattern dimension) of 1 or more to about 2. In other words, when a desired final film thickness or pattern height is 10 μm, the pattern must be formed with a dimension of 10 μm or less, or about 5 μm.

Besides, Patent Document 6 describes a patterning process using a photosensitive resin composition that contains a material utilizing polyamic acid, which is a precursor of polyimide, for example, a resin in which an ester bond is introduced into a carboxyl group of polyamic acid. In some examples of this patterning process, a formed film is baked at a relatively low temperature of 250° C. to obtain an intended polyimide film. However, a solvent in this photosensitive resin composition is N-methyl-2-pyrrolidone, and N-methyl-2-pyrrolidone is also used for development process. Thus, it is not preferred for the above reasons. Moreover, this patent document fails to specifically disclose the resolution capacity.

Patent Document 7 refers to patterning of a negative photosensitive resin composition using a polyimide precursor. This photosensitive resin composition contains N-methyl-2-pyrrolidone-based solvent, but utilizes cyclopentanone for development. This patent document discloses about the resolution capacity, specifically, that an aspect ratio of 1 or more can be achieved. However, this aspect ratio is not a ratio of final film thickness or pattern height to pattern dimension, but a ratio of film thickness to dimension after coating and drying. Thus, this resolution capacity is not a practical value and should be improved. Moreover, although the use of cyclopentanone, which is an organic solvent widely used, as the developer is preferred, the use of an organic solvent sometimes easily causes overhang profile just after development due to swelling of the film during the development.

Furthermore, Patent Document 8 refers to patterning of a negative photosensitive resin composition using a polyimide precursor. This photosensitive resin composition contains γ-butyrolactone as a solvent and utilizes an alkaline aqueous solution as a developer. In the patterning process, solubility in the alkaline developer is improved by incorporating acidic groups, i.e., alkali-soluble groups such as carboxyl groups into the resin of the polyimide precursor, and a pattern is formed by development with alkaline aqueous solution. The development with alkaline aqueous solution is difficult to cause swelling and can improve pattern profile and resolution capacity. However, when the alkali-soluble groups are incorporated into the resin, although the resolution is improved, the resin after curing cannot withstand a removing liquid having an extremely strong alkalinity, which is used for removing a resist pattern for plating in a step of forming a metal wiring. This problem still remain unsolved. To form an excellent insulating top coat, the alkali-soluble groups in the resin require completely sealing or completely removing from the system.

As mentioned above, the pattern miniaturization in rewiring technology of an insulating top coat is expected to progress more and more in future with the increase of density and integration of chips. It is thus strongly desired to develop a photosensitive resin composition using a polymer having a polyimide precursor structural unit that can achieve high resolution while maintaining excellent properties such as mechanical strength and adhesiveness of a pattern and a top coat of polyimide obtained by baking.

It is also strongly desired that the insulating top coat after patterning and curing has resistance to heat in various steps and resistance to various chemicals.

In summary, it is desired to rapidly develop the photosensitive resin composition having all of the above properties without lack.

PRIOR ART DOCUMENTS

Patent Documents

Patent Document 1: Japanese Patent Laid-Open Publication No. S49-115541
Patent Document 2: Japanese Patent Laid-Open Publication No. S55-45746
Patent Document 3: Japanese Patent No. 3232022
Patent Document 4: Japanese Patent No. 3721768
Patent Document 5: Japanese Patent No. 5417623
Patent Document 6: Japanese Patent Laid-Open Publication No. 2005-49504
Patent Document 7: WO2013/168675
Patent Document 8: Japanese Patent No. 3627488

SUMMARY OF THE INVENTION

The present invention was accomplished in view of the above-described circumstances. It is an object of the present invention to provide a tetracarboxylic acid diester compound that can give a polyimide precursor polymer soluble in a safe organic solvent widely used as a solvent of a composition and usable as a base resin of a photosensitive resin composition; a polyimide precursor polymer obtained by using the tetracarboxylic acid diester compound; and a method for producing the same.

Another object of the present invention is to provide a photosensitive resin composition using as a base resin a polyimide precursor polymer that can improve the resolution without deteriorating the pattern profile due to swelling or the like at development with organic solvent in patterning, and to provide a photosensitive resin composition that can utilize a widely used safe organic solvent at development with organic solvent.

Further object of the present invention is to provide a photosensitive resin composition excellent in resolution and capable of forming a fine pattern by development with alkaline aqueous solution in patterning.

To achieve this object, the present invention provides a tetracarboxylic acid diester compound shown by the following general formula (1),

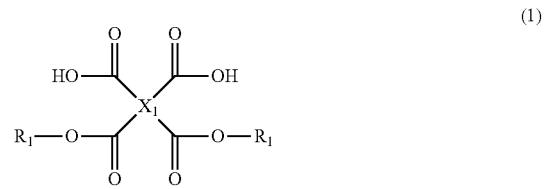

wherein $X_1$ represents a tetravalent organic group; and $R_1$ represents a group shown by the following general formula (2),

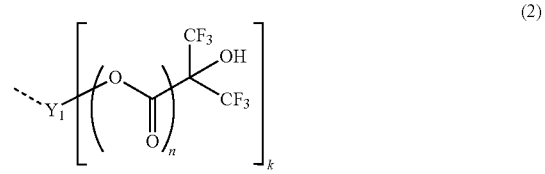

wherein the dotted line represents a bond; $Y_1$ represents an organic group with a valency of k+1; "k" represents 1 or 2; and "n" represents 0 or 1.

This tetracarboxylic acid diester compound can give a polyimide precursor polymer that is soluble in a safe organic solvent widely used as a solvent of a composition and is usable as a base resin of a photosensitive resin composition.

In the compound, $Y_1$ in the general formula (2) is preferably a divalent organic group selected from linear or branched alkylene groups having 1 to 6 carbon atoms.

This compound sufficiently shows the effect of the present invention.

In the compound, $R_1$ in the general formula (1) is preferably an organic group selected from groups shown by the following formulae (3), (4), and (5),

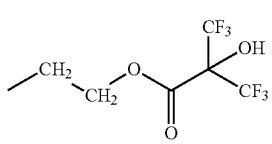

(5)

wherein the dotted line represents a bond.

$R_1$ is preferably the above group because a compound used as a raw material for introducing $R_1$ is available.

Furthermore, the present invention provides a polyimide precursor polymer comprising a structural unit shown by the following general formula (6),

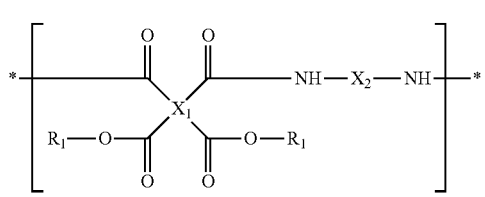

(6)

wherein $X_1$ represents a tetravalent organic group; $X_2$ represents a divalent organic group; and $R_1$ represents a group shown by the following general formula (2),

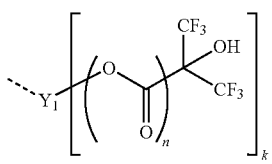

(2)

wherein the dotted line represents a bond; $Y_1$ represents an organic group with a valency of k+1; "k" represents 1 or 2; and "n" represents 0 or 1.

The polyimide precursor polymer having the structural unit shown by the general formula (6) can be derived from the tetracarboxylic acid diester compound shown by the general formula (1). The tetracarboxylic acid diester compound shown by the general formula (1) contains an organic group $R_1$ shown by the general formula (2) (for example, an organic group selected from groups shown by the formulae (3) to (5)), which contains a hexafluoroisopropanol group. Generally, most polymers having a polyimide precursor structural unit are soluble only in a polar solvent such as N-methyl-2-pyrrolidone, but the polyimide precursor structural unit shown by the general formula (6) derived from the tetracarboxylic acid diester compound shown by the general formula (1), which incorporates the hexafluoroisopropanol group into the polymer, allows the polymer to easily dissolve in a widely used organic solvent and to form a composition with the widely used organic solvent.

Furthermore, the hexafluoroisopropanol group incorporated into the polymer is an alkali-soluble acidic group, and thus the polyimide precursor polymer having the structural unit shown by the general formula (6) can give an alkali-soluble photosensitive resin composition.

This polyimide precursor polymer preferably further comprises a structural unit shown by the following general formula (7),

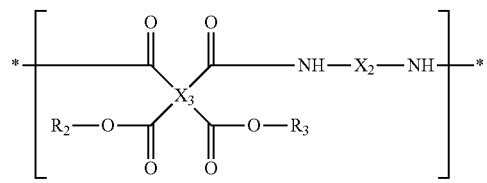

(7)

wherein $X_2$ has the same meaning as above; $X_3$ represents a tetravalent organic group that is the same as or different from $X_1$; and $R_2$ and $R_3$ independently represent a hydrogen atom, a linear, branched, or cyclic alkyl group having 1 to 6 carbon atoms, or an organic group shown by the following general formula (8), provided that at least one of $R_2$ and $R_3$ is an organic group shown by the general formula (8),

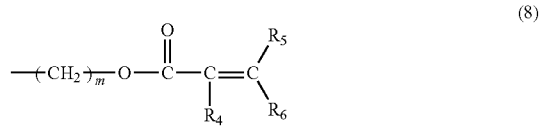

(8)

wherein the dotted line represents a bond; $R_4$ represents a hydrogen atom or an organic group having 1 to 3 carbon atoms; $R_5$ and $R_6$ independently represent a hydrogen atom or an organic group having 1 to 3 carbon atoms; and "m" represents an integer of 2 to 10.

This polymer has a polymerizable unsaturated bonding group in the structural unit thereof. Thus, when this polymer is combined with a later-described photo radical initiator, radical polymerization progresses by radicals generated at an exposed part in patterning as an initiator, and the polymer is insolubilized in a developer. This allows the polymer to form a negative photosensitive resin composition without an additional crosslinking agent.

Moreover, while the structural unit shown by the general formula (6), which contains a hexafluoroisopropanol group, i.e., an acidic group, makes the polymer alkali-soluble, the polyimide precursor structural unit shown by the general formula (7) incorporated into the polymer at an appropriate proportion enables adjustment of the dissolution rate of the polymer in an alkaline aqueous solution. This allows an optimal pattern formation by the development with alkaline aqueous solution.

Furthermore, the present invention provides a method for producing the above polyimide precursor polymer, comprising reacting a tetracarboxylic acid diester compound shown by the following general formula (1) with a diamine shown by the following general formula (9),

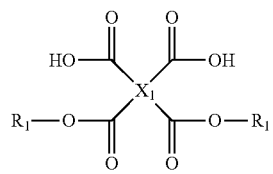

(1)

wherein $X_1$ and $R_1$ have the same meanings as above, $H_2N-X_2-NH_2$ (9)

wherein $X_2$ has the same meaning as above.

The polyimide precursor polymer having the structural unit shown by the general formula (6) can be produced, for example, by the above method.

Furthermore, the present invention provides a method for producing the above polyimide precursor polymer, comprising reacting a tetracarboxylic acid diester compound shown by the following general formula (1) with a diammine shown by the following general formula (9) and a tetracarboxylic acid diester compound shown by the following general formula (10),

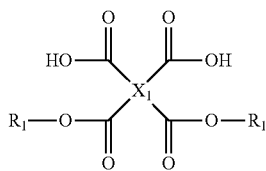

(1)

wherein $X_1$ and $R_1$ have the same meanings as above, $$H_2N-X_2-NH_2 \quad (9)$$

wherein $X_2$ has the same meaning as above,

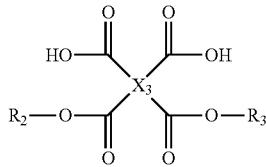

(10)

wherein $X_3$, $R_2$, and $R_3$ have the same meanings as above.

The polyimide precursor polymer having the structural unit shown by the general formula (7) can be produced, for example, by the above method.

Furthermore, the present invention provides a negative photosensitive resin composition comprising:

(A) the polyimide precursor polymer having the structural unit shown by the general formula (7);
(B) a photo-radical initiator; and
(D) a solvent.

As mentioned above, the polyimide precursor polymer having the structural unit shown by the general formula (7) has a polymerizable unsaturated bonding group in the structural unit. Thus, a negative photosensitive resin composition can be obtained by combining this polymer with a photo-radical initiator.

Furthermore, the present invention provides a negative photosensitive resin composition comprising:

(A') the above polyimide precursor polymer;
(B) a photo-radical initiator;
(C) a crosslinking agent having two or more photo-polymerizable unsaturated bonding groups per molecule; and
(D) a solvent.

In this composition, the polyimide precursor polymer that contains no structural unit shown by the general formula (7) can be a polymer having no polymerizable or crosslinkable structure in its molecule. In this case, a negative composition can be formed by adding a crosslinking agent having photo-polymerizable unsaturated bonding groups. On the other hand, the polyimide precursor polymer having the structural unit shown by the general formula (7) already has a polymerizable unsaturated bonding group in its molecule, but an additional crosslinking agent may be added.

Furthermore, the present invention provides a negative photosensitive resin composition comprising:

(A') the above polyimide precursor polymer;
(B') a photo acid generator;
(C') one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

(C-1)

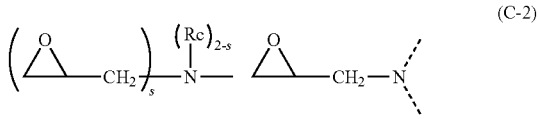

(C-2)

wherein the dotted line represents a bond, Rc represents a linear, branched, or cyclic alkyl group having 1 to 6 carbon atoms, and "s" represents 1 or 2; and (D) a solvent.

Use of the photo acid generator of component (B') generates an acid at an exposed part in patterning, thereby crosslinking between crosslinking groups of the added crosslinking agent of component (C') and crosslinking reaction points of the polymer. This makes the exposed part insoluble in a developer, providing the composition capable of forming a negative image.

Furthermore, the present invention provides a positive photosensitive resin composition comprising:

(A') the above polyimide precursor polymer;
(B") a compound having a quinonediazide structure for serving as a photosensitive agent capable of generating an acid by light and increasing a dissolution rate in an alkaline aqueous solution;
(C") one or two or more crosslinking agents selected from a crosslinking agent having two or more photo-polymerizable unsaturated bonding groups per molecule, an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

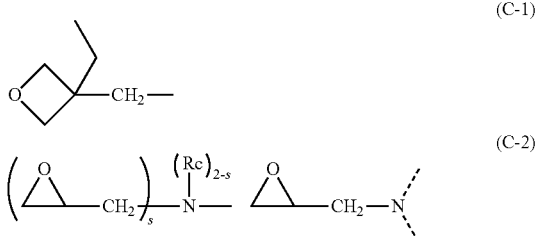

wherein the dotted line represents a bond, Rc represents a linear, branched, or cyclic alkyl group having 1 to 6 carbon atoms, and "s" represents 1 or 2; and (D) a solvent.

Use of the photosensitive agent of component (B") accelerates the dissolution rate of an exposed part with respect to an alkaline developer and makes the exposed part soluble in the developer in patterning, providing a positive image. The polyimide precursor polymer having the structural unit shown by the general formula (6) contains a hexafluoroisopropanol group, which is an alkali-soluble substituent, in its molecule, and thus the polymer itself is alkali-soluble. Accordingly, this polymer hardly causes residues such as scum in the bottom of an opening pattern and pattern deterioration such as footing profile, and is effective in forming a fine pattern.

The positive photosensitive resin composition preferably further comprises (E) a compound capable of generating an acid or a radical by heat.

The composition containing the component (E) can promote post-curing and improve properties such as mechanical strength, chemical resistance, and adhesiveness of an obtained pattern or a film.

Furthermore, the present invention provides a patterning process comprising:

(1) applying the above negative photosensitive resin composition onto a substrate to form a photosensitive material film;

(2) exposing the photosensitive material film to a high energy beam having a wavelength of 190 to 500 nm or an electron beam via a photomask after a heat treatment; and (3) performing development with a developer of an alkaline aqueous solution or an organic solvent.

The polyimide precursor polymer used as the base resin of the inventive negative photosensitive resin composition contains the structural unit shown by the general formula (6) and thus a hexafluoroisopropanol group. This hexafluoroisopropanol group can prevent concerns of swelling during development with organic solvent in the patterning process. Moreover, this patterning process is especially suitable for a negative photosensitive resin composition using a polymer having a polymerizable unsaturated bonding group as a base resin.

The patterning process preferably further comprises performing post-exposure bake between the exposing step and the development step.

In particular, when the negative photosensitive resin composition containing the polyimide precursor polymer having the structural unit shown by the general formula (7) is used, the post exposure bake (PEB) step can promote crosslinking reaction between crosslinking groups of the crosslinking agent and crosslinking reaction points of the polymer by using an acid generated from the photo acid generator during exposure as a catalyst.

Furthermore, the present invention provides a patterning process comprising:

(I) applying the above positive photosensitive resin composition onto a substrate to form a photosensitive material film;

(II) exposing the photosensitive material film to a high energy beam having a wavelength of 190 to 500 nm or an electron beam via a photomask after a heat treatment; and (III) performing development with a developer of an alkaline aqueous solution.

In this manner, the inventive positive photosensitive resin composition enables alkali development with alkaline aqueous solution.

Furthermore, the present invention provides a method for forming a cured film, comprising baking a film having a pattern formed by the above patterning process at 100 to 300° C. and post-curing the film.

The inventive polyimide precursor polymer contains a hexafluoroisopropanol group and thus is alkali-soluble. However, the polyimide precursor structural unit in this polyimide precursor polymer causes imide ring-closure reaction in the post-curing step, consequently eliminating and removing the alkali-soluble hexafluoroisopropanol group from the system. Thus, the cured film after post-curing has no alkali-soluble group, and becomes a very stable polyimide resin film. This cured film has extremely improved resistance to chemical agents, especially, a removing liquid having an extremely strong alkalinity, which is used for removing a resist pattern for plating in a step of forming a metal wiring. Such a cured film with a pattern can serve as an excellent top coat for protecting electric and electronic parts or an excellent insulating top coat.

The present invention can provide a tetracarboxylic acid diester compound that can give a polyimide precursor polymer soluble in a safe organic solvent widely used as a solvent of a composition and usable as a base resin of a photosensitive resin composition. When a photosensitive resin composition containing a polyimide precursor polymer obtained from the tetracarboxylic acid diester compound is used for a patterning process, in the case of development with organic solvent, a widely used safe organic solvent can be used for the development, and swelling can be prevented during the development. Thus, a fine pattern with a good profile can be obtained. Meanwhile in the case of development with alkaline aqueous solution, the inventive polymer having the polyimide precursor structural unit, which is soluble in an alkaline aqueous solution, can prevent residues such as scum in the bottom of an opened pattern and pattern deterioration such as footing profile. Thus, a fine pattern can be resolved.

Furthermore, the present invention can provide a cured film having excellent chemical resistance by post-curing the obtained film having a pattern to remove the alkali-solubility and the organic-solvent-solubility, which have effectively functioned in patterning, from the system by imide ring-closure reaction, providing a stable polyimide film. Moreover, the obtained film can serve as a top coat excellent in mechanical strength, substrate adhesiveness, electric characteristics, and reliability, which are characteristic of polyimide.

DETAILED DESCRIPTION OF THE PREFERRED EMBODIMENTS

As mentioned above, it is desired to develop a tetracarboxylic acid diester compound that can give a polyimide precursor polymer soluble in a safe organic solvent widely used as a solvent of a composition and usable as a base resin of a photosensitive resin composition.

The present inventors have earnestly investigated to achieve the above object and consequently found the following: the polymer (the polyimide precursor polymer) having the polyimide precursor structural unit obtained from the tetracarboxylic acid diester compound shown by the general formula (1) is useful as a base resin of a composition since this polymer can easily dissolve in a widely used safe organic solvent. This polymer is usable in any of a negative photosensitive resin composition available for development with organic solvent, a negative photosensitive resin composition available for development with alkaline aqueous solution, and a positive photosensitive resin composition available for development with alkaline aqueous solution. A fine pattern having good pattern profile is obtained by using such photosensitive resin compositions. In addition, since the polymer having the polyimide precursor structural unit obtained from the tetracarboxylic acid diester compound shown by the general formula (1) can easily dissolve in a widely used safe organic solvent, the widely used safe organic solvent can be advantageously used for development with organic solvent.

Moreover, although the polymer having the polyimide precursor structural unit obtained from the tetracarboxylic acid diester compound shown by the general formula (1) is a resin that is soluble in alkaline aqueous solution, a film obtained by patterning and baking of a photosensitive resin composition containing this polymer has excellent resistance to a plating-removing liquid with strong alkalinity.

Furthermore, a top coat obtained by patterning and baking of a photosensitive resin composition containing the polymer having the polyimide precursor structural unit as a base resin has excellent mechanical strength and adhesiveness. In other words, a cured film having a pattern formed by the photosensitive resin composition containing the polymer having the polyimide precursor structural unit as a base resin can serve as an excellent top coat for protecting electric and electronic parts or an excellent insulating top coat. The present invention was brought to completion from these findings.

That is, the present invention is a tetracarboxylic acid diester compound shown by the following general formula (1),

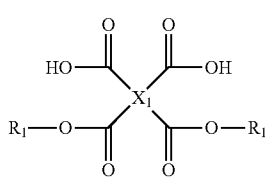

(1)

wherein $X_1$ represents a tetravalent organic group; and $R_1$ represents a group shown by the following general formula (2),

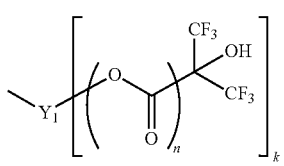

(2)

wherein the dotted line represents a bond; $Y_1$ represents an organic group with a valency of k+1; "k" represents 1 or 2; and "n" represents 0 or 1.

Hereinafter, the present invention will be described in detail, but the present invention is not limited thereto.

[Tetracarboxylic Acid Diester Compound]

The inventive tetracarboxylic acid diester compound is shown by the following general formula (1),

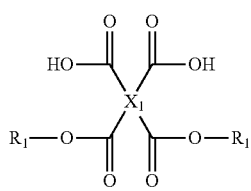

(1)

wherein $X_1$ represents a tetravalent organic group; and $R_1$ represents a group shown by the following general formula (2),

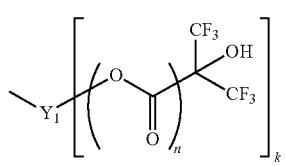

(2)

wherein the dotted line represents a bond; $Y_1$ represents an organic group with a valency of k+1; "k" represents 1 or 2; and "n" represents 0 or 1.

$X_1$ in the general formula (1) represents a tetravalent organic group and is not limited to particular tetravalent organic groups. $X_1$ is preferably a tetravalent organic group of an alicyclic aliphatic group having 4 to 40 carbon atoms or an aromatic group, more preferably a tetravalent organic group shown by the following formula (11). The structure of $X_1$ may be one kind or a combination of two or more kinds.

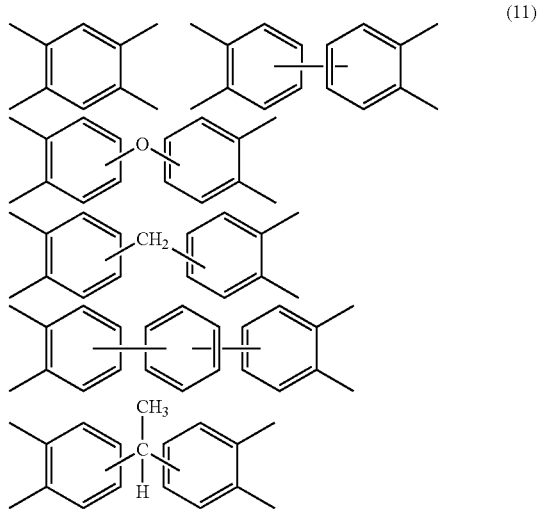

(11)

-continued

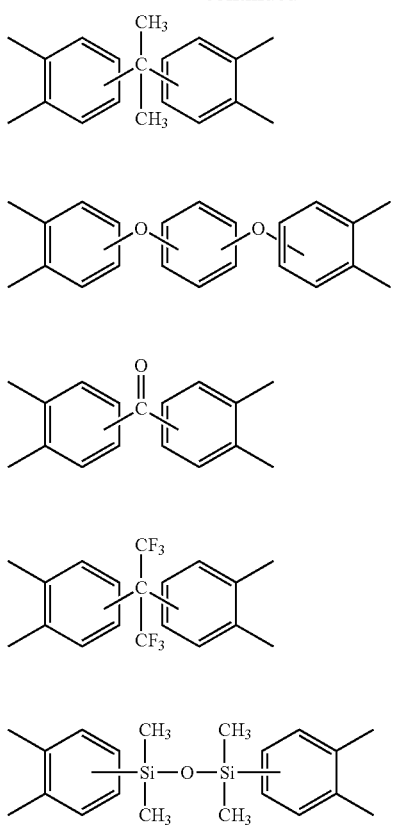

wherein the dotted line represents a bond.

Preferable examples of $R_1$ in the general formula (1) include groups shown by the following formulae (3), (4), (5), (12), (13), and (14),

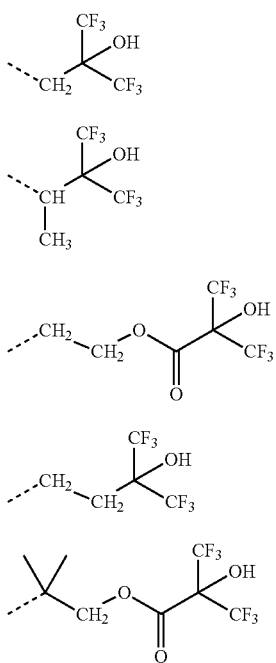

-continued

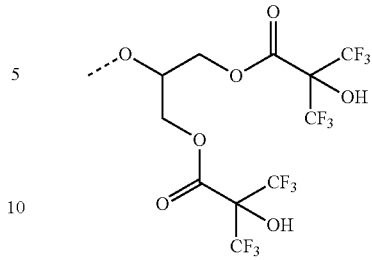

(14)

wherein the dotted line represents a bond.

Moreover, $R_1$ is preferably selected from groups shown by the formulae (3), (4), and (5) because of availability of a compound having a hydroxyl group at its terminal as shown by a later-described general formula (16).

In this regard, after patterning of a photosensitive resin composition using the inventive polymer having the polyimide precursor structural unit as a base resin, the polyimide precursor structural unit undergoes imidization ring-closure reaction by heating for post-curing. At this time, the introduced $R_1$ is eliminated and removed from the system, and thus the thickness of the formed film is reduced. Thus, $R_1$ more preferably has low molecular weight to minimize the film loss during post-curing. That is, the most preferable $R_2$ is the structure shown by the formula (3).

$Y_1$ in the general formula (2) is preferably a divalent organic group selected from linear or branched alkylene groups having 1 to 6 carbon atoms.

(Method for Producing Tetracarboxylic Acid Diester Compound)

The inventive tetracarboxylic acid diester compound can be produced, for example, by reacting a tetracarboxylic dianhydride shown by the following general formula (15) with a compound having a hydroxyl group at its terminal shown by the following general formula (16) in the presence of a basic catalyst such as pyridine to introduce $R_1$. In this method, the tetracarboxylic dianhydride shown by the general formula (15) provides $X_1$ (e.g., a tetravalent organic group shown by the formula (11)) in the general formula (1), and the compound having a hydroxyl group at the terminal shown by the general formula (16) introduces the organic group shown by the general formula (2) thereto.

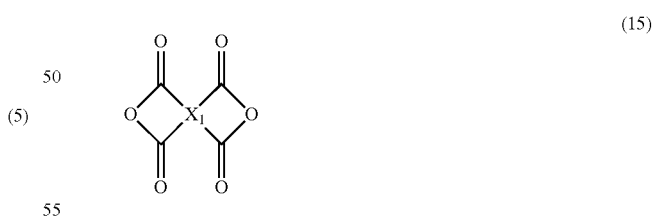

(15)

wherein $X_1$ has the same meaning as above,

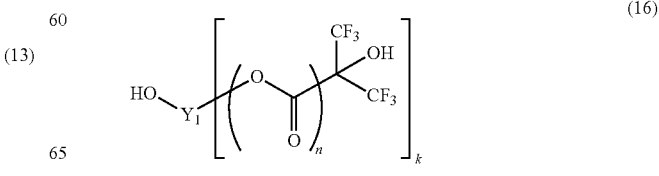

(16)

wherein $Y_1$, "k", and "n" have the same meanings as above.

Preferable examples of the tetracarboxylic dianhydride shown by the general formula (15) include aromatic dianhydrides, alicyclic dianhydrides, and aliphatic dianhydrides. Examples of the aromatic dianhydride include pyromellitic dianhydride, 3,3',4,4'-biphenyltetracarboxylic dianhydride, 2,3,3',4'-biphenyltetracarboxylic dianhydride, 2,3,2',3'-biphenyltetracarboxylic dianhydride, 3,3',4,4'-terphenyltetracarboxylic dianhydride, 3,3',4,4'-oxyphthalic dianhydride, 2,3,3',4'-oxyphthalic dianhydride, 2,3,2',3'-oxyphthalic dianhydride, diphenylsulfone-3,3',4,4'-tetracarboxylic dianhydride, benzophenone-3,3',4,4'-tetracarboxylic dianhydride, 2,2-bis(3,4-dicarboxyphenyl) propane dianhydride, 2,2-bis(2,3-dicarboxyphenyl) propane dianhydride, 1,1-bis(3,4-dicarboxypheny)ethane dianhydride, 1,1-bis(2,3-dicarboxyphenyl)ethane dianhydride, bis(3,4-dicarboxyphenyl) methane dianhydride, bis(2,3-dicarboxyphenyl)methane dianhydride, 1,4-(3,4-dicarboxyphenoxy)benzene dianhydride, p-phenylene bis (trimellitic acid monoester anhydride), bis(1,3-dioxo-1,3-dihydroisobenzofuran-5-carboxylic acid) 1, 4-phenylene, 2,2-bis(4-(4-aminophenoxy) phenyl)propane, 1,2,5,6-naphthalenetetracarboxylic dianhydride, 2,3,6,7-naphthalenetetracarboxylic dianhydride, 9,9-bis(3,4-dicarboxyphenyl)fluorene dianhydride, 2,3,5,6-pyridinetetracarboxylic dianhydride, 3,4,9,10-perylenetetracarboxylic dianhydride, 2,2-bis(3,4-dicarboxyphenyl) hexafluoropropane dianhydride, 2,2-bis(4-(3,4-dicarboxybenzoyloxy)phenyl)hexafluoropropane dianhydride, 1,6-difluoropromellitic dianhydride, 1-trifluoromethylpyromellitic dianhydride, 1,6-ditrifluoromethylpyromellitic dianhydride, 2,2'-bis(trifluoromethyl)-4,4'-bis(3,4-dicarboxyphenoxy)biphenyl dianhydride, 2,2'-bis[(dicarboxyphenoxy)phenyl]propane dianhydride, 2,2'-bis[(dicarboxyphenoxy)phenyl]hexafluoropropane dianhydride, and acid dianhydride compounds obtained by substituting the aromatic ring of the above compounds with a substituent such as an alkyl group, an alkoxy group, or a halogen atom, although not limited thereto.

Examples of the alicyclic dianhydride include 1,2,3,4-cyclobutanetetracarboxylic dianhydride, 1,2,3,4-cyclopentanetetracarboxylic dianhydride, 1,2,4,5-cyclohexanetetracarboxylic dianhydride, 1,2,4,5-cyclopentanetetracarboxylic dianhydride, 1,2,3,4-tetramethyl-1,2,3,4-cyclobutanetetracarboxylic dianhydride, 1,2-dimethyl-1,2,3,4-cyclobutanetetracarboxylic dianhydride, 1,3-dimethyl-1,2,3,4-cyclobutanetetracarboxylic dianhydride, 1,2,3,4-cycloheptanetetracarboxylic dianhydride, 2,3,4,5-tetrahydrofurantetracarboxylic dianhydride, 3,4-dicarboxy-1-cyclohexylsuccinic dianhydride, 2,3,5-tricarboxycyclopentylacetic dianhydride, 3,4-dicarboxy-1,2,3,4-tetrahydro-1-naphthalenesuccinic dianhydride, bicyclo[3.3.0]octane-2,4,6,8-tetracarboxylic dianhydride, bicyclo[4.3.0]nonane-2, 4,7,9-tetracarboxylic dianhydride, bicyclo[4.4.0]decane-2,4,7,9-tetracarboxylic dianhydride, bicyclo[4.4.4.0]decane-2, 4, 8, 10-tetracarboxylic dianhydride, tricyclo[6.3.0.0$^{2,6}$]undecane-3,5,9,11-tetracarboxylic dianhydride, bicyclo[2.2.2]octane-2, 3, 5,6-tetracarboxylic dianhydride, bicyclo[2.2.2]oct-7-ene-2,3,5,6-tetracarboxylic dianhydride, bicyclo[2.2.1]heptane tetracarboxylic dianhydride, bicyclo[2.2.1]heptane-5-carboxymethyl-2,3, 6-tricarboxylic dianhydride, 7-oxabicyclo[2.2.1]heptane-2,4,6,8-tetracarboxylic dianhydride, octahydronaphthalene-1,2,6,7-tetracarboxylic dianhydride, tetradecahydroanthracene-1,2, 8,9-tetracarboxylic dianhydride, 3,3',4,4'-dicyclohexanetetracarboxylic dianhydride, 3,3',4,4'-oxydicyclohexanetetracarboxylic dianhydride, 5-(2,5-dioxotetrahydro-3-furanyl)-3-methyl-3-cyclohexene-1, 2-dicarboxylic anhydride, and "RIKACID" (registered trade mark) BT-100 (manufactured by New Japan Chemical Co., Ltd), derivatives thereof, and acid dianhydride compounds obtained by substituting the alicyclic ring of the above compounds with a substituent such as an alkyl group, an alkoxy group, or a halogen atom, although not limited thereto.

Examples of the aliphatic dianhydride include 1,2,3,4-butanetetracarboxylic dianhydride, 1,2,3,4-pentanetetracarboxylic dianhydride, and derivative thereof, although not limited thereto.

These aromatic dianhydrides, alicyclic dianhydrides, and aliphatic dianhydrides may be used alone or in combination of two or more kinds.

For the reaction of the tetracarboxylic dianhydride shown by the general formula (15) with the compound having a hydroxyl group at the terminal shown by the general formula (16), the tetracarboxylic dianhydride shown by the general formula (15) and the compound having a hydroxyl group at the terminal shown by the general formula (16) are stirred, dissolved, and mixed in the presence of a basic catalyst such as pyridine in a reaction solvent, at a reaction temperature of 20 to 50° C., over 4 to 10 hours. In this manner, half-esterification reaction of the acid dianhydride progresses, and a solution in which an intended tetracarboxylic acid diester compound shown by the general formula (1) is dissolved in the reaction solvent can be obtained.

The obtained tetracarboxylic acid diester compound may be isolated, or the obtained solution as is may be used for a subsequent reaction with a diamine.

The reaction solvent is preferably a solvent that can favorably dissolve the above tetracarboxylic acid diester compound and a polymer having a polyimide precursor structural unit obtained by the subsequent polycondensation reaction of the tetracarboxylic acid diester compound with a diamine. Examples of the solvent include N-methyl-2-pyrrolidone, N,N-dimethylacetamide, N,N-dimethylformamide, dimethylsulfoxide, tetramethylurea, and γ-butyrolactone. In addition, ketones, esters, lactones, ethers, halogenated hydrocarbons, and hydrocarbons can also be used. Illustrative examples thereof include acetone, methyl ethyl ketone, methyl isobutyl ketone, cyclohexanone, methyl acetate, ethyl acetate, butyl acetate, diethyl oxalate, ethylene glycol dimethyl ether, diethylene glycol dimethyl ether, tetrahydrofuran, dichloromethane, 1,2-dichloroethane, 1,4-dichlorobutane, chlorobenzene, o-dichlorobenzene, hexane, heptane, benzene, toluene, and xylene. These solvents may be used alone or in combination of two or more kinds as needed. However, as mentioned above, the use of N-methyl-2-pyrrolidone is desirably avoided.

[Polyimide Precursor Polymer]

The inventive polyimide precursor polymer (a polymer having a polyimide precursor structural unit) contains the structural unit shown by the following general formula (6) (hereinafter, also referred to as a polymer having the structural unit (6)),

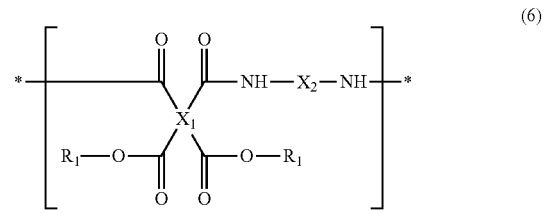

(6)

wherein X₁ represents a tetravalent organic group; X₂ represents a divalent organic group; and R₁ represents a group shown by the following general formula (2),

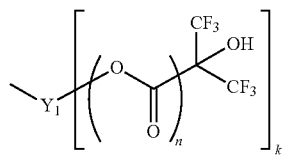
(2)

wherein the dotted line represents a bond; Y₁ represents an organic group with a valency of k+1; "k" represents 1 or 2; and "n" represents 0 or 1.

X₁ and R₁ in the general formula (6) are the same as in the general formula (1) described above. X₂ in the general formula (6), which is any divalent organic group, is preferably a divalent organic group having 6 to 40 carbon atoms, more preferably a cyclic organic group containing 1 to 4 aromatic or alicyclic rings each having a substituent, or an aliphatic group or siloxane group having no cyclic structure. X₂ is still more preferably a structure shown by the following formula (17) or (18). The structure of X₂ may be one kind or a combination of two or more kinds.

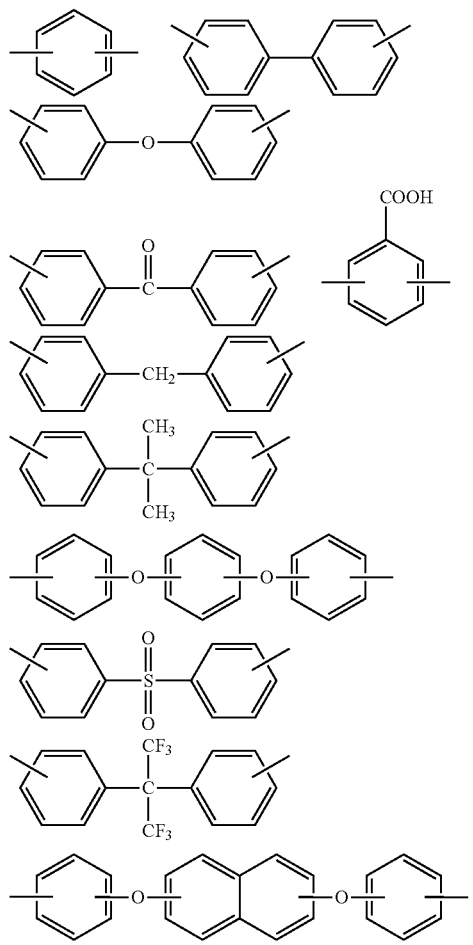
(17)

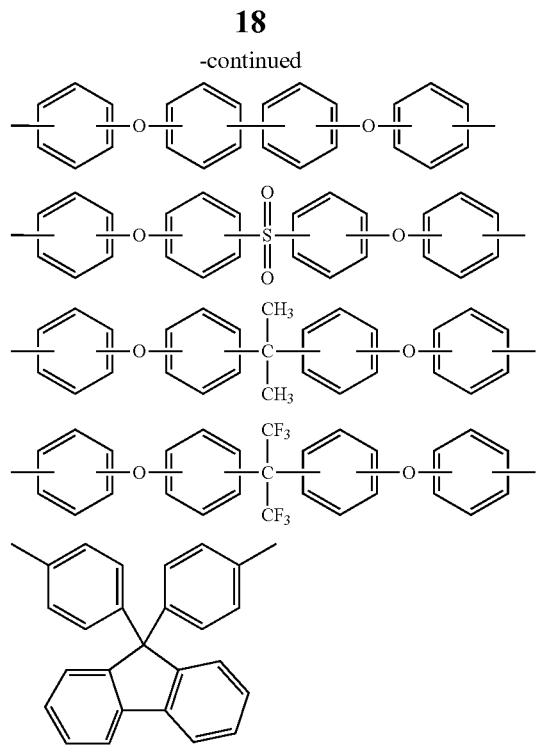

wherein the dotted line represents a bond with an amino group.

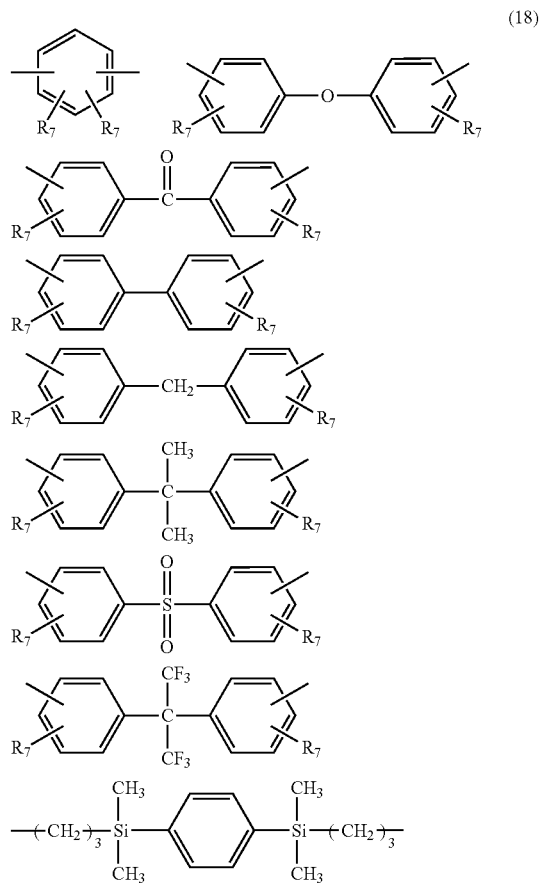
(18)

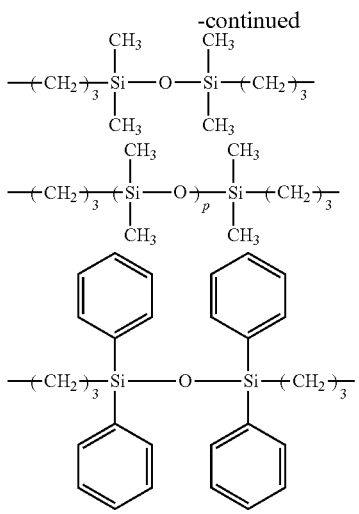

wherein the dotted line represents a bond with an amino group; $R_7$ independently represents a methyl group, an ethyl group, a propyl group, a n-butyl group, or a trifluoromethyl group; and "p" represents a positive number of 2 to 20.

The inventive polyimide precursor polymer preferably further contains the structural unit shown by the following general formula (7) (hereinafter, also referred to as a polymer having the structural units (6) and (7)),

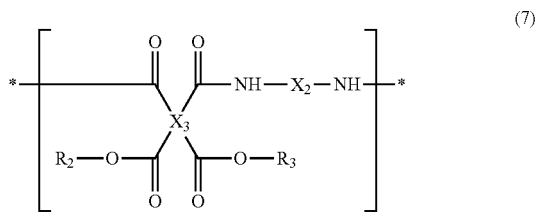

wherein $X_2$ has the same meaning as above; $X_3$ represents a tetravalent organic group that is the same as or different from $X_1$; and $R_2$ and $R_3$ independently represent a hydrogen atom, a linear, branched, or cyclic alkyl group having 1 to 6 carbon atoms, or an organic group shown by the following general formula (8), provided that at least one of $R_2$ and $R_3$ is an organic group shown by the general formula (8),

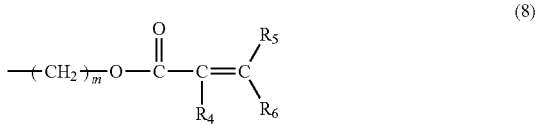

wherein the dotted line represents a bond; $R_4$ represents a hydrogen atom or an organic group having 1 to 3 carbon atoms; $R_5$ and $R_6$ independently represent a hydrogen atom or an organic group having 1 to 3 carbon atoms; and "m" represents an integer of 2 to 0.0.

In the general formula (7), $X_3$ represents a tetravalent organic group that is the same as or different from $X_1$ and is not limited to particular tetravalent organic groups. $X_3$ is preferably a tetravalent organic group of an alicyclic aliphatic group having 4 to 40 carbon atoms or an aromatic group, more preferably selected from tetravalent organic groups shown by the formula (11). The structure of $X_3$ may be one kind or a combination of two or more kinds.

$R_4$ in the general formula (8), which is a hydrogen atom or any organic group having 1 to 3 carbon atoms, is preferably a hydrogen atom or a methyl group, in view of photosensitive property of a photosensitive resin composition.

$R_5$ and $R_6$ in the general formula (8), which independently represent a hydrogen atom or any organic group having 1 to 3 carbon atoms, are preferably a hydrogen atom, in view of photosensitive property of a photosensitive resin composition.

"m" in the general formula (8), which represents an integer of 2 to 10, is preferably an integer of 2 to 4, in view of photosensitive property. "m" is more preferably 2.

$R_2$ and $R_3$ in the general formula (7) independently represent a hydrogen atom, a linear, branched, or cyclic alkyl group having 1 to 6 carbon atoms, or an organic group shown by the general formula (8), provided that at least one of $R_2$ and $R_3$ is an organic group shown by the general formula (8).

(Method for Producing Polyimide Precursor Polymer)

Furthermore, the present invention provides a method for producing the inventive polyimide precursor polymer. The polyimide precursor polymer having the structural unit (6) can be obtained by reacting a tetracarboxylic acid diester compound shown by the following general formula (1) with a diamine shown by the following general formula (9),

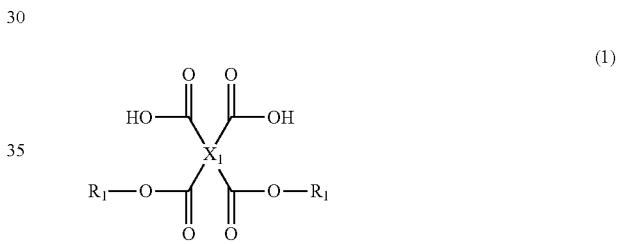

wherein $X_1$ and $R_1$ have the same meanings as above,

wherein $X_2$ has the same meaning as above.

Examples of the diamine shown by the general formula (9) include aromatic diamines, alicyclic diamines, and aliphatic diamines. Preferable examples of the aromatic diamine include 3,4'-diaminodiphenyl ether, 4,4'-diaminodiphenyl ether, 3,4'-diaminodiphenylmethane, 4,4'-diaminodiphenylmethane, 3,3'-diaminodiphenylsulfone, 3,4'-diaminodiphenylsulfone, 4,4'-diaminodiphenylsulfone, 3,4'-diaminodiphenylsulfide, 4,4'-diaminodiphenylsulfide, 1,4-bis(4-aminophenoxy)benzene, benzidine, 2,2'-bis(trifluoromethyl)benzidine, 3,3'-bis(trifluoromethyl)benzidine, 2,2'-dimethylbenzidine, 3,3'-dimethylbenzidine, 2,2'3,3'-tetramethylbenzidine, 2,2'-dichlorobenzidine, 3,3'-dichlorobenzidine, 2,2'3,3'-tetrachlorobenzidine, m-phenylenediamine, p-phenylenediamine, 1,5-naphthalenediamine, 2,6-naphthalenediamine, bis(4-aminophenoxyphenyl)sulfone, bis(3-aminophenoxyphenyl)sulfone, bis[4-(3-aminophenoxy)phenyl]sulfone, bis(4-aminophenoxy) biphenyl, bis{4-(4-aminophenoxy)phenyl}ether, 1,4-bis(4-aminophenoxy)benzene, 9,9-bis(4-aminophenyl) fluorene, 2,2'-bis[3-(3-aminobenzamido)-4-hydroxyphenyl]hexafluoropropane, 4-aminophenyl-4'-aminobenzoate, 4,4'-diaminobenzanilide, and diamine compounds obtained by substituting the aromatic ring of the above compounds with a substituent such as an alkyl group, an alkoxy group, or a halogen atom, although not limited thereto.

Examples of the alicyclic diamine include cyclobutanediamine, isophoronediamine, bicyclo[2.2.1]heptanebismethylamine, tricyclo[3.3.1.1³,⁷]decane-1,3-diamine, 1,2-cyclohexyldiamine, 1,3-cyclohexyldiamine, 1,4-diaminocyclohexane, trans-1,4-diaminocyclohexane, cis-1,4-diaminocyclohexane, 4,4'-diaminodicyclohexylmethane, 3,3'-dimethyl-4,4'-diaminodicyclohexylmethane, 3,3'-diethyl-4,4'-diaminodicyclohexylmethane, 3,3',5,5'-tetramethyl-4,4'-diaminodicyclohexylmethane, 3,3',5,5'-tetraethyl-4,4'-diaminodicyclohexylmethane, 3,5-diethyl-3',5'-dimethyl-4,4'-diaminodicyclohexylmethane, 4,4'-diaminodicyclohexyl ether, 3,3'-dimethyl-4,4'-diaminodicyclohexyl ether, 3,3'-diethyl-4,4'-diaminodicyclohexyl ether, 3, 3',5,5'-tetramethyl-4, 4'-diaminodicyclohexyl ether, 3,3',5,5'-tetraethyl-4,4'-diaminodicyclohexyl ether, 3,5-diethyl-3',5'-dimethyl-4,4'-diaminodicyclohexyl ether, 2,2-bis(4-aminocyclohexyl)propane, 2,2-bis(3-methyl-4-aminocyclohexyl) propane, 2,2-bis(3-ethyl-4-aminocyclohexyl)propane, 2,2-bis(3,5-dimethyl-4-aminocyclohexyl) propane, 2,2-bis(3,5-diethyl-4-aminocyclohexyl) propane, 2,2-(3,5-diethyl-3',5'-dimethyl-4,4'-diaminodicyclohexyl)propane, and diamine compounds obtained by substituting the alicyclic ring of the above compounds with a substituent such as an alkyl group, an alkoxy group, or a halogen atom, although not limited thereto.

Examples of the aliphatic diamine include alkylene diamines such as ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, and 1,10-diaminodecane; ethylene glycol diamines such as bis(aminomethyl)ether, bis(2-aminoethyl) ether, and bis(3-aminopropyl)ether; and siloxane diamines such as 1,3-bis(3-aminopropyl)tetramethyldisiloxane, 1,3-bis(4-aminobutyl)tetramethyldisiloxane, and α,ω-bis(3-aminopropyl)polydimethylsiloxane, although not limited thereto.

These aromatic diamines, alicyclic diamines, or aliphatic diamines may be used alone or in combination of two or more kinds.

In addition, siloxane diamines can also be suitably used.

The polyimide precursor polymer having the structural unit shown by the general formula (6) can be obtained, for example, by reacting the tetracarboxylic acid diester compound shown by the general formula (1) with the diamine shown by the general formula (9) in the presence of a dehydration condensation agent. More specifically, the tetracarboxylic acid diester compound shown by the general formula (1) is used with a reaction solvent dissolving it. To this reaction solvent, a known dehydration condensation agent (for example, dicyclohexylcarbodiimide, 1-ethoxycarbonyl-2-ethoxy-1,2,-dihydroquinoline, 1,1-carbonyldioxy-di-1,2,3-benzotriazole, or N,N'-disuccinimidylcarbonate) is added and mixed under ice-cooling to obtain a polyacid anhydride of the tetracarboxylic acid diester compound shown by the general formula (1). Then, the diamine shown by the general formula (9) is separately dissolved or dispersed in a solvent, and this solution or dispersion is added dropwise to the anhydride to perform polycondensation. The polyimide precursor polymer having the structural unit shown by the general formula (6) can be thus obtained.

As an alternative method for reacting the tetracarboxylic acid diester compound shown by the general formula (1) with the diamine shown by the general formula (9) to obtain the polyimide precursor polymer having the structural unit shown by the general formula (6), the tetracarboxylic acid diester compound shown by the general formula (1) may be converted to an acid chloride by a chlorinating agent such as thionyl chloride or dichlorooxalic acid and then undergo reaction with the diamine shown by the general formula (9) to synthesize the polymer.

In the reaction of the tetracarboxylic acid diester compound by a chlorinating agent to convert to an acid chloride, a basic compound may be used. Examples of the basic compound include pyridine, 4-dimethylaminopyridine, and triethylamine.

Then, the resulting acid chloride of the tetracarboxylic acid diester compound is reacted with the diamine shown by the general formula (9) in the presence of a basic catalyst to obtain an intended polyimide precursor polymer having the structural unit shown by the general formula (6). Examples of the basic catalyst include pyridine, dimethylaminopyridine, 1,8-diazabicyclo[5.4.0]undec-7-ene, and 1,5-diazabicyclo[4.3.0]non-5-ene.

The solvent used in the method for producing the inventive polyimide precursor polymer via an acid chloride is preferably a solvent that can favorably dissolve the tetracarboxylic acid diester compound, the acid chloride thereof, and the polyimide precursor polymer obtained by polycondensation reaction with a diamine, and the same solvent as described above may be used. Illustrative examples thereof include N-methyl-2-pyrrolidone, N,N-dimethylacetamide, N,N-dimethylformamide, dimethylsulfoxide, tetramethylurea, hexamethylphosphoric triamide, and γ-butyrolactone. In addition to polar solvents, ketones, esters, lactones, ethers, halogenated hydrocarbons, and hydrocarbons can also be used. Illustrative examples thereof include acetone, diethyl ketone, methyl ethyl ketone, methyl isobutyl ketone, cyclohexanone, methyl acetate, ethyl acetate, butyl acetate, diethyl oxalate, diethyl malonate, diethyl ether, ethylene glycol dimethyl ether, diethylene glycol dimethyl ether, tetrahydrofuran, dichloromethane, 1,2-dichloroethane, 1,4-dichlorobutane, trichloroethane, chlorobenzene, o-dichlorobenzene, hexane, heptane, octane, benzene, toluene, and xylene. These solvents may be used alone or in combination of two or more kinds. However, as mentioned above, the use of N-methyl-2-pyrrolidone is desirably avoided.

The molecular weight of the intended polyimide precursor polymer having the structural unit shown by the general formula (6) is preferably 5,000 to 100,000, more preferably 7,000 to 30,000. When the molecular weight is 5,000 or more, a photosensitive resin composition using the polyimide precursor polymer as a base resin can be easily applied to form a film with a desired thickness on a substrate. When the molecular weight is 100,000 or less, viscosity of the photosensitive resin composition is not so high that a film can be formed.

In addition, the polyimide precursor polymer having the structural unit shown by the general formula (6) and the structural unit shown by the general formula (7) can be produced by reacting a tetracarboxylic acid diester compound shown by the following general formula (1) with a diamine shown by the following general formula (9) and a tetracarboxylic acid diester compound shown by the following general formula (10),

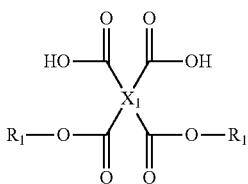

wherein $X_3$ and $R_1$ have the same meanings as above, $$H_2N—X_2—NH_2 \quad (9)$$

wherein $X_2$ has the same meaning as above,

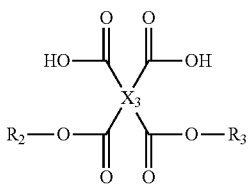

wherein $X_3$, $R_2$, and $R_3$ have the same meanings as above.

In the general formula (10), $X_3$ represents a tetravalent organic group that is the same as or different from $X_1$ and is not limited to particular tetravalent organic groups. $X_3$ is preferably a tetravalent organic group of an alicyclic aliphatic group having 4 to 40 carbon atoms or an aromatic group, more preferably selected from tetravalent organic groups shown by the formula (11). The structure of $X_3$ may be one kind or a combination of two or more kinds.

$R_2$ and $R_3$ in the general formula (10) independently represent a hydrogen atom, a linear, branched, or cyclic alkyl group having 1 to 6 carbon atoms, or an organic group shown by the general formula (8), provided that at least one of $R_2$ and $R_3$ is an organic group shown by the general formula (8). Here, the tetracarboxylic acid diester compound shown by the general formula (10) can be obtained by reaction of a tetracarboxylic dianhydride that provides $X_3$ (e.g., a tetravalent organic group shown by the formula (11)) with a compound having a hydroxyl group at the terminal shown by the following general formula (19) in the presence of a basic catalyst such as pyridine to introduce the organic group shown by the general formula (8) into at least one of $R_2$ and $R_3$,

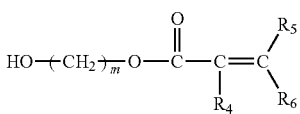

wherein $R_4$, $R_5$, $R_6$, and "m" have the same meanings as above.

The reaction of the tetracarboxylic dianhydride with the compound having a hydroxyl group at the terminal shown by the general formula (19) can be performed, specifically, in the same manner as the above-described reaction of the tetracarboxylic dianhydride with the compound having a hydroxyl group at the terminal shown by the general formula (16).

$R_4$ in the general formula (19), which is a hydrogen atom or any organic group having 1 to 3 carbon atoms, is preferably a hydrogen atom or a methyl group, in view of photosensitive property of a photosensitive resin composition.

$R_5$ and $R_6$ in the general formula (19), which independently represent a hydrogen atom or any organic group having 1 to 3 carbon atoms, are preferably a hydrogen atom, in view of photosensitive property of a photosensitive resin composition.

"m" in the general formula (19), which represents an integer of 2 to 10, is preferably an integer of 2 to 4, in view of photosensitive property. "m" is more preferably 2.

Preferable examples of the compound having a hydroxyl group at the terminal shown by the general formula (19) include 2-acryloyloxyethyl alcohol, 1-acryloyloxy-3-propyl alcohol, 2-methacryloyloxyethyl alcohol, and 1-methacryloyloxy-3-propyl alcohol.

In addition, $R_2$ and $R_3$ in the general formula (10) may be a linear, branched, or cyclic alkyl group having 1 to 6 carbon atoms. As a method for introducing a linear, branched, or cyclic alkyl group having 1 to 6 carbon atoms into the compounds of formulae (7) and (10) (i.e., a method for making $R_2$ and $R_3$ a linear, branched, or cyclic alkyl group having 1 to 6 carbon atoms), there may be mentioned a method in which a linear, branched, or cyclic alcohol having 1 to 6 carbon atoms is added simultaneously with the reaction of the compound having a hydroxyl group at the terminal shown by the general formula (19) and the tetracarboxylic dianhydride in the presence of a basic catalyst such as pyridine.

Examples of alcohol suited for the reaction include methanol, ethanol, 1-propanol, 2-propanol, i-butanol, 2-butanol, 1-pentanol, 2-pentanol, 3-pentanol, neopentyl alcohol, 1-hexanol, 2-hexanol, 3-hexanol, cyclopentanol, and cyclohexanol.

The reaction of the tetracarboxylic acid diester compound shown by the general formula (1), the tetracarboxylic acid diester compound shown by the general formula (10), and the diamine shown by the general formula (9) can be performed in the same manner as the above-described reaction of the tetracarboxylic acid diester compound shown by the general formula (1) with the diamine shown by the general formula (9).

The molecular weight of the polymer having the structural units (6) and (7) is the same as that of the above-described polymer having the structural unit (6), namely, preferably 5,000 to 100,000, more preferably 7,000 to 30,000.

Both terminals of the polymer having the structural unit (6) and the polymer having the structural units (6) and (7) may be sealed with a terminal sealing agent to control the molecular weight at polycondensation reaction and to inhibit time-dependent change of the molecular weight of the obtained polymer, i.e., to inhibit gelation. A terminal sealing agent for the acid dianhydride may be a monoamine or a monohydric alcohol. A terminal sealing agent for the diamine compound may be an acid anhydride, a monocarboxylic acid, a monoacid chloride compound, a mono-active ester compound, a dicarbonic acid ester, or a vinyl ether. In addition, reaction of the terminal sealing agent allows various organic groups to be introduced into the terminal.

Examples of the monoamine used as the sealing agent for the acid anhydride terminal include aniline, 5-amino-8-hydroxyquinoline, 4-amino-8-hydroxyquinoline, 1-hydroxy-8-aminonaphthalene, 1-hydroxy-7-aminonaphthalene, 1-hydroxy-6-aminonaphthalene, 1-hydroxy-5-aminonaphthalene, 1-hydroxy-4-aminonaphthalene, 1-hydroxy-3-aminonaphthalene, 1-hydroxy-2-aminonaphthalene, 1-amino-7-hydroxynaphthalene, 2-hydroxy-7- aminonaphthalene, 2-hydroxy-6-aminonaphthalene, 2-hydroxy-5-aminonaphthalene, 2-hydroxy-4-aminonaphthalene, 2-hydroxy-3-aminonaphthalene, 1-amino-2-hydroxynaphthalene, 1-carboxy-8-aminonaphthalene, 1-carboxy-7-aminonaphthalene, 1-carboxy-6-aminonaphthalene, 1-carboxy-5-aminonaphthalene, 1-carboxy-4-aminonaphthalene, 1-carboxy-3-aminonaphthalene, 1-carboxy-2-aminonaphthalene, 1-amino-7-carboxynaphthalene, 2-carboxy-7-aminonaphthalene, 2-carboxy-6-aminonaphthalene, 2-carboxy-5-aminonaphthalene, 2-carboxy-4-aminonaphthalene, 2-carboxy-3-aminonaphthalene, 1-amino-2-carboxynaphthalene, 2-aminonicotinic acid, 4-aminonicotinic acid, 5-aminonicotinic acid, 6-aminonicotinic acid, 4-aminosalicylic acid, 5-aminosalicylic acid, 6-aminosalicylic acid, ameride, 2-aminobenzoic acid, 3-aminobenzoic acid, 4-aminobenzoic acid, 2-aminobenzenesulfonic acid, 3-aminobenzenesulfonic acid, 4-aminobenzenesulfonic acid, 3-amino-4, 6-dihydroxypyrimidine, 2-aminophenol, 3-aminophenol, 4-aminophenol, 5-amino-8-mercaptoquinoline, 4-amino-8-mercaptoquinoline, 1-mercapto-8-aminonaphthalene, 1-mercapto-7-aminonaphthalene, 1-mercapto-6-aminonaphthalene, 1-mercapto-5-aminonaphthalene, 1-mercapto-4-aminonaphthalene, 1-mercapto-3-aminonaphthalene, 1-mercapto-2-aminonaphthalene, 1-amino-7-mercaptonaphthalene, 2-mercapto-7-aminonaphthalene, 2-mercapto-6-aminonaphthalene, 2-mercapto-5-aminonaphthalene, 2-mercapto-4-aminonaphthalene, 2-mercapto-3-aminonaphthalene, 1-amino-2-mercaptonaphthalene, 3-amino-4, 6-dimercaptopyrimidine, 2-aminothiophenol, 3-aminothiophenol, 4-aminothiophenol, 2-ethyntylaniline, 3-ethynylaniline, 4-ethynylaniline, 2,4-diethynylaniline, 2, 5-diethynylaniline, 2,6-diethynylaniline, 3,4-diethynylaniline, 3, 5-diethynylaniline, 1-ethynyl-2-aminonaphthalene, 1-ethynyl-3-aminonaphthalene, 1-ethynyl-4-aminonaphthalene, 1-ethynyl-5-aminonaphthalene, 1-ethynyl-6-aminonaphthalene, 1-ethynyl-7-aminonaphthalene, 1-ethynyl-8-aminonaphthalene, 2-ethynyl-1-aminonaphthalene, 2-ethynyl-3-aminonaphthalene, 2-ethynyl-4-aminonaphthalene, 2-ethynyl-5-aminonaphthalene, 2-ethynyl-6-aminonaphthalene, 2-ethynyl-7-aminonaphthalene, 2-ethynyl-8-aminonaphthalene, 3,5-diethynyl-1-aminonaphthalene, 3,5-diethynyl-2-aminonaphthalene, 3, 6-diethynyl-1-aminonaphthalene, 3, 6-diethynyl-2-aminonaphthalene, 3, 7-diethynyl-1-aminonaphthalene, 3, 7-diethynyl-2-aminonaphthalene, 4, 8-diethynyl-1-aminonaphthalene, and 4, 8-diethynyl-2-aminonaphthalene, although not limited thereto. These compounds may be used alone or in combination or two or more kinds.

Examples of the monohydric alcohol used as the sealing agent for the acid anhydride terminal include methanol, ethanol, 1-propanol, 2-propanol, 1-butanol, 2-butanol, 1-pentanol, 2-pentanol, 3-pentanol, 1-hexanol, 2-hexanol, 3-hexanol, 1-heptanol, 2-heptanol, 3-heptanol, 1-octanol, 2-octanol, 3-octanol, 1-nonanol, 2-nonanol, 1-decanol, 2-decanol, 1-undecanol, 2-undecanol, 1-dodecanol, 2-dodecanol, 1-tridecanol, 2-tridecanol, 1-tetradecanol, 2-tetradecanol, 1-pentadecanol, 2-pentadecanol, 1-hexadecanol, 2-hexadecanol, 1-heptadecanol, 2-heptadecanol, 1-octadecanol, 2-octadecanol, 1-nonadecanol, 2-nonadecanol, 1-icosanol, 2-methyl-1-propanol, 2-methyl-2-propanol, 2-methyl-1-butanol, 3-methyl-1-butanol, 2-methyl-2-butanol, 3-methyl-2-butanol, 2-propyl-1-pentanol, 2-ethyl-1-hexanol, 4-methyl-3-heptanol, 6-methyl-2-heptanol, 2,4,4-trimethyl-1-hexanol, 2,6-dimethyl-4-heptanol, isononyl alcohol, 3,7-dimethyl-3-octanol, 2, 4-dimethyl-1-heptanol, 2-heptylundecanol, ethylene glycol monoethyl ether, ethylene glycol monomethyl ether, ethylene glycol monobutyl ether, propylene glycol 1-methyl ether, diethylene glycol monoethyl ether, diethylene glycol monomethyl ether, diethylene glycol monobutyl ether, cyclopentanol, cyclohexanol, cyclopentane monomethylol, dicyclopentane monomethylol, tricyclodecane monomethylol, norborneol, and terpineol, although not limited thereto. These compounds may be used alone or in combination or two or more kinds.

Examples of the acid anhydride, the monocarboxylic acid, the monoacid chloride compound, and the mono-active ester compound used as the sealing agent for terminal amino groups include acid anhydrides such as phthalic anhydride, maleic anhydride, nadic anhydride, cyclohexanedicarboxylic anhydride, and 3-hydroxyphthalic anhydride; monocarboxylic acids such as 2-carboxyphenol, 3-carboxyphenol, 4-carboxyphenol, 2-carboxythiophenol, 3-carboxythiophenol, 4-carboxythiophenol, 1-hydroxy-6-carboxynaphthalene, 1-hydroxy-7-carboxynaphthalene, 1-hydroxy-6-carboxynaphthalene, 1-hydroxy-5-carboxynaphthalene, 1-hydroxy-4-carboxynaphthalene, 1-hydroxy-3-carboxynaphthalene, 1-hydroxy-2-carboxynaphthalene, 1-mercapto-8-carboxynaphthalene, 1-mercapto-7-carboxynaphthalene, 1-mercapto-6-carboxynaphthalene, 1-mercapto-5-carboxynaphthalene, 1-mercapto-4-carboxynaphthalene, 1-mercapto-3-carboxynaphthalene, 1-mercapto-2-carboxynaphthalene, 2-carboxybenzenesulfonic acid, 3-carboxybenzenesulfonic acid, 4-carboxybenzenesulfonic acid, 2-ethynylbenzoic acid, 3-ethynylbenzoic acid, 4-ethynylbenzoic acid, 2, 4-diethynylbenzoic acid, 2,5-diethynylbenzoic acid, 2,6-diethynylbenzoic acid, 3,4-diethynylbenzoic acid, 3,5-diethynylbenzoic acid, 2-ethynyl-1-naphthoic acid, 3-ethynyl-1-naphthoic acid, 4-ethynyl-1-naphthoic acid, 5-ethynyl-1-naphthoic acid, 6-ethynyl-1-naphthoic acid, 7-ethynyl-1-naphthoic acid, 8-ethynyl-1-naphthoic acid, 2-ethynyl-2-naphthoic acid, 3-ethynyl-2-naphthoic acid, 4-ethynyl-2-naphthoic acid, 5-ethynyl-2-naphthoic acid, 6-ethynyl-2-naphthoic acid, 7-ethynyl-2-naphthoic acid, and 8-ethynyl-2-naphthoic acid and monoacid chloride compounds obtained by acid-chloridizing carboxyl groups of the above monocarboxylic acids; monoacid chloride compounds obtained by acid-chloridizing only a monocarboxyl group of dicarboxylic acids such as terephthalic acid, phthalic acid, maleic acid, cyclohexanedicarboxylic acid, 3-hydroxyphthalic acid, 5-norbornene-2,3-dicarboxylic acid, 1,2-dicarboxynaphthalene, 1,3-dicarboxynaphthalene, 1,4-dicarboxynaphthalene, 1,5-dicarboxynaphthalene, 1,6-dicarboxynaphthalene, 1,7-dicarboxynaphthalene, 1,8-dicarboxynaphthalene, 2,3-dicarboxynaphthalene, 2,6-dicarboxynaphthalene, and 2,7-dicarboxynaphthalene; and active ester compounds obtained by reaction of a monoacid chloride compound with N-hydroxybenzotriazole or N-hydroxy-5-norbornene-2,3-dicarboxyimide.

Examples of the dicarbonic acid ester used as the sealing agent for terminal amino groups include di-tert-butyl dicarbonate, dibenzyl dicarbonate, dimethyl dicarbonate, and diethyl dicarbonate.

Examples of the vinyl ether compound used as the sealing agent for terminal amino groups include chloroformic acid esters such as tert-butyl chloroformate, n-butyl chloroformate, isobutyl chloroformate, benzyl chloroformate, allyl chloroformate, ethyl chloroformate, and isopropyl chloroformate; isocyanate compounds such as butyl isocyanate, 1-naphthyl isocyanate, octadecyl isocyanate, and phenyl isocyanate; butyl vinyl ether, cyclohexyl vinyl ether, ethyl vinyl ether, 2-ethyhexyl vinyl ether, isobutyl vinyl, ether, isopropyl vinyl ether, n-propyl vinyl ether, tert-butyl vinyl ether, and benzyl vinyl ether.

Examples of other compounds used as the sealing agent for terminal amino groups include benzoyl chloride, fluorenylmethyl chloroformate, 2,2,2-trichloroethyl chloroformate, methanesulfonyl chloride, p-toluenesulfonyl chloride, and phenyl isocyanate.

The introduction rate of the sealing agent for acid anhydride terminal is preferably 0.1 to 60 mol %, more preferably 5 to 50 mol %, much more preferably 5 to 20 mol %, with respect to tetracarboxylic dianhydride components corresponding to the general formula (15), which are a raw material of the inventive polyimide precursor polymer. Additionally, the introduction rate of the sealing agent for terminal amino groups is preferably 0.1 to 100 mol %, particularly preferably 5 to 90 mol %, with respect to diamine components. Moreover, multiple different terminal groups may be introduced by reaction with multiple terminal sealing agents.

The inventive polyimide precursor polymer may contain, in addition to the structural unit shown by the general formula (6) and the structural unit shown by the general formula (7), other polyimide precursor structural units, polyimide structural units, polybenzoxazole structural units, and polybenzoxazole precursor structural units.

[Photosensitive Resin Composition]

Then, a photosensitive resin composition using the inventive polyimide precursor polymer as a base resin will be described. In the present invention, a negative photosensitive resin composition and a positive photosensitive resin composition can be obtained by using the inventive polyimide precursor polymer as their base resin.

[Negative Photosensitive Resin Composition]

First, explanation will be given for the negative photosensitive resin composition, using the inventive polyimide precursor polymer as a base resin, which is capable of forming a negative pattern and available for organic solvent development or alkali development. The negative photosensitive resin composition of the present invention can have the following three embodiments, although the composition is not limited thereto.

A negative photosensitive resin composition according to a first embodiment of the present invention contains:
(A) the polyimide precursor polymer having the structural unit shown by the general formula (7);
(B) a photo-radical initiator; and
(D) a solvent.

The component (A) in the negative photosensitive resin composition according to the first embodiment is the polyimide precursor polymer having the structural unit shown by the general formula (7) (i.e., the polymer having the structural units (6) and (7)). This polymer has a polymerizable unsaturated bonding group in its molecule. Thus, the negative photosensitive resin composition can be obtained by combining this polymer with a photo-radical initiator.

The component (A), the polymer having the structural units (6) and (7), contains a hexafluoroisopropanol group. In other words, this polymer contains an organic group corresponding to the general formula (2) (an organic group $R_1$ in the general formula (6)). Introduction of the hexafluoroisopropanol group into the polymer allows the polymer to dissolve in a widely used organic solvent and to form a composition with a widely used organic solvent (D) described later. Moreover, introduction of the hexafluoroisopropanol group into the polymer enables organic solvent development with a widely used organic solvent and prevents concerns of swelling during the organic solvent development.

Preferable rate of the hexafluoroisopropanol group introduced into the component (A) can be expressed by mole number of hexafluoroisopropanol groups contained in 100 g of the component (A). Specifically, the introduction rate of the hexafluoroisopropanol group which allows the polymer to easily dissolve in a widely used organic solvent is preferably 0.02 mol or more, more preferably 0.05 mol or more, with respect to 100 g of the component (A). The introduction amount of the hexafluoroisopropanol group is much more preferably 0.1 mol or more with respect to 100 g of the component (A); this range prevents swelling during organic solvent development.

In the case of alkali development, the introduction amount of the hexafluoroisopropanol group in the component (A) is preferably 0.15 mol to 0.58 mol, more preferably 0.20 mol to 0.30 mol, most preferably 0.25 mol to 0.30 mol, with respect to 100 g of the component (A). When the introduction rate of the hexafluoroisopropanol group is 0.15 mol or more with respect to 100 g of the component (A), a desired alkali dissolution rate can be obtained with respect to an alkaline developer, and failure at pattern opening and scum in pattern bottom are not caused in patterning, thus preventing reduction in resolution. On the other hand, possible amount of the hexafluoroisopropanol group that can be introduced into 100 g of the component (A) is 0.58 mol in design of the inventive polyimide precursor polymer. This amount enables the highest solubility in an alkaline developer. However, after patterning of the inventive photosensitive resin composition, the polyimide precursor structural unit of the inventive polyimide precursor polymer undergoes imidization ring-closure reaction by heating for post-curing. At this time, an organic group having the introduced hexafluoroisopropanol group is eliminated and removed from the system, and thus the thickness of the formed film is reduced. Thus, the introduction amount of the hexafluoroisopropanol group is preferably 0.30 mol or less.

The component (B) in the negative photosensitive resin composition according to the first embodiment is a photo-radical initiator. The photo-radical initiator may be appropriately selected from compounds conventionally used as a photo-polymerization initiator for UV curing. Examples of the photo-radical initiator include benzophenone derivatives such as benzophenone, methyl o-benzoylbenzoate, 4-benzoyl-4'-methyl diphenyl ketone, dibenzyl ketone, and fluorenone; acetophenone derivatives such as 2,2'-diethoxyacetophenone, 2-hydroxy-2-methylpropiophenone, 1-hydroxycyclohexyl phenyl ketone; thioxanthone derivatives such as thioxanthone, 2-methylthioxanthone, 2-isopropylthioxanthone, and diethylthioxanthone; benzyl derivatives such as benzyl, benzyl dimethyl ketal and benzyl-β-methoxyethyl acetal; benzoin derivatives such as benzoin and benzoin methyl ether; oximes such as 1-phenyl-1,2-butanedione-2-(O-methoxycarbonyl) oxime, 1-phenyl-1,2-propanedione-2-(O-methoxycarbonyl) oxime, 1-phenyl-1,2-propanedione-2-(O-ethoxycarbonyl) oxime, 1-phenyl-1,2-propanedione-2-(O-benzoyl) oxime, 1,3-diphenylpropanetrione-2-(O-ethoxycarbonyl) oxime, and 1-phenyl-3-ethoxypropanetrione-2-(O-benzoyl) oxime; N-arylglycines such as N-phenylglycine; peroxides such as benzoyl perchloride; and aromatic biimidazoles, although not limited thereto. These compounds may be used alone or in combination or two or more kinds. Among the above photo-radical initiators, oximes are particularly preferable in view of photosensitivity.

The formulation amount of the component (B) is preferably 0.1 part by mass to 20 parts by mass, more preferably 2 parts by mass to 15 parts by mass, with respect to 100 parts by mass of the component (A), the inventive polyamide precursor polymer, in view of photosensitivity. A negative photosensitive resin composition obtained by blending 0.1 part by mass or more of the component (B) to 100 parts by mass of the component (A) has excellent photosensitivity; a negative photosensitive resin composition obtained by blending 20 parts by mass or less of the component (B) to 100 parts by mass of the component (A) has excellent thick film curability.

The component (D) in the negative photosensitive resin composition according to the first embodiment is a solvent. The solvent of component (D) is not limited as long as it can dissolve the component (A) and the component (B). Examples of the solvent include ketones such as cyclohexanone, cyclopentanone, and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, and γ-butyrolactone; and these may be used one or more kinds. Among them, ethyl lactate, cyclohexanone, cyclopentanone, propylene glycol monomethyl ether acetate, and γ-butyrolactone, or a mixture of them are particularly preferable.

The formulation amount of the component (D) is preferably 50 to 2,000 parts by mass, more preferably 100 to 1,000 parts by mass, with respect to 100 parts by mass of the total amount of the component (A) and the component (B).

The negative photosensitive resin composition according to the first embodiment may further contain other components besides the components (A), (B), and (D). Examples of the other components include (F) a sensitizer, an adhesion assistant, a polymerization inhibitor for enhancing storage stability, and (G) a surfactant conventionally used for improving coating property.

Examples of (F) the sensitizer include 7-N,N-diethylaminocoumarin, 7-di ethylamino-3-thenonylcoumarin, 3,3'-carbonylbis(7-N,N-diethylamino) coumarin, 3,3'-carbonylbis (7-N,N-dimethoxy) coumarin, 3-thienylcarbonyl-7-N,N-diethylaminocoumarin, 3-benzoylcoumarin, 3-benzoyl-7-N,N-methoxycoumarin, 3-(4'-methoxybenzoyl)coumarin, 3,3'-carbonylbis-5,7-(dimethoxy)coumarin, benzalacetophenone, 4'-N,N-dimethylaminobenzalacetophenone, 4'-acetaminobenzal-4-methoxyacetophenone, dimethylaminobenzophenone, diethylaminobenzophenone, and 4,4'-bis(N-ethyl,N-methyl)benzophenone. The amount thereof is preferably 0.05 to 20 parts by mass, more preferably 0.1 to 10 parts by mass, with respect to 100 parts by mass of the inventive polyimide precursor polymer.

(G) the surfactant is preferably a nonionic surfactant such as a fluorinated surfactant. Illustrative examples thereof include perfluoroalkyl polyoxyethylene ethanol, fluorinated alkyl ester, perfluoroalkylamine oxide, and a fluorine-containing organosiloxane compound.

The surfactant may be commercially available products, and illustrative examples thereof include Flolade "FC-4430" (available from Sumitomo 3M Ltd.), Surfion "S-141" and "S-145" (both are available from Asahi Glass Co., Ltd.), Unidyne "DS-401", "DS-4031", and "DS-451" (all are available from Daikin Industries, Ltd.), Megafac "F-8151" (available from DIC Co.), and "X-70-093" (available from Shin-Etsu Chemical Co., Ltd.). Among them, Flolade "FC-4430" (available from Sumitomo 3M Ltd.) and "X-70-093" (available from Shin-Etsu Chemical Co., Ltd.) are preferable.

A negative photosensitive resin composition according to a second embodiment of the present invention contains:

(A') the polymer having the structural unit (6) or the polymer having the structural units (6) and (7);

(B) a photo-radical initiator;

(C) a crosslinking agent having two or more photopolymerizable unsaturated bonding groups per molecule; and (D) a solvent.

The component (A') in the negative photosensitive resin composition according to the second embodiment is the polymer having the structural unit (6) or the polymer having the structural units (6) and (7). The polymer having the structural unit (6) can have no polymerizable or crosslinkable structure in its polymer molecule. Thus, the negative photosensitive resin composition according to the second embodiment can be formed by adding a crosslinking agent having polymerizable unsaturated bonding groups of component (C). On the other hand, the polymer having the structural units (6) and (7) already has a polymerizable unsaturated bonding group in its polymer molecule, but an additional crosslinking agent may be added.

The polymer of component (A') contains a hexafluoroisopropanol group. In other words, this polymer contains an organic group corresponding to the general formula (2) (an organic group $R_1$ in the general formula (6)). Introduction of the hexafluoroisopropanol group into the polymer allows the polymer to dissolve in a widely used organic solvent and to form a composition with a widely used organic solvent (D) described later. Moreover, introduction of the hexafluoroisopropanol group into the polymer enables organic solvent development with a widely used organic solvent and prevents concerns of swelling during the organic solvent development.

Preferable rate of the hexafluoroisopropanol group introduced into the component (A') can be expressed by mole number of hexafluoroisopropanol groups contained in 100 g of the component (A'). Specifically, the introduction rate of the hexafluoroisopropanol group which allows the polymer to easily dissolve in a widely used organic solvent is preferably 0.02 mol or more, more preferably 0.05 mol or more, with respect to 100 g of the component (A'). The introduction amount of the hexafluoroisopropanol group is much more preferably 0.1 mol or more with respect to 100 g of the component (A'); this range prevents swelling during organic solvent development.

In the case of alkali development, the introduction amount of the hexafluoroisopropanol group in the component (A') is preferably 0.15 mol to 0.58 mol, more preferably 0.20 mol to 0.30 mol, most preferably 0.25 mol to 0.30 mol, with respect to 100 g of the component (A'). When the introduction rate of the hexafluoroisopropanol group is 0.15 mol or more with respect to 100 g of the component (A'), a desired alkali dissolution rate can be obtained with respect to an alkaline developer, and failure at pattern opening and scum in pattern bottom are not caused in patterning, thus preventing reduction in resolution. On the other hand, possible amount of the hexafluoroisopropanol group that can be introduced into 100 g of the component (A') is 0.58 mol in design of the inventive polyimide precursor polymer. This amount enables the highest solubility in an alkaline developer. However, after patterning of the inventive photosensitive resin composition, the polyimide precursor structural unit of the inventive polyimide precursor polymer undergoes imidization ring-closure reaction by heating for post-curing. At this time, an organic group having the introduced hexafluoroisopropanol group is eliminated and removed from the system, and thus the thickness of the formed film is reduced. Thus, the introduction amount of the hexafluoroisopropanol group is preferably 0.30 mol or less.

The component (B) in the negative photosensitive resin composition according to the second embodiment is a photo-radical initiator. As the photo-radical initiator of component (B), the same compounds as described in the first embodiment can be used.

The formulation amount of the component (B) is preferably 0.1 part by mass to 20 parts by mass, more preferably 2 parts by mass to 15 parts by mass, with respect to 100 parts by mass of the component (A'), the inventive polyimide precursor polymer, in view of photosensitivity. A negative photosensitive resin composition obtained by blending 0.1 part by mass or more of the component (B) to 100 parts by mass of the component (A') has excellent photosensitivity; a negative photosensitive resin composition obtained by blending 20 parts by mass or less of the component (B) to 100 parts by mass of the component (A') has excellent thick film curability.

The component (C) in the negative photosensitive resin composition according to the second embodiment is a crosslinking agent having two or more photo-polymerizable unsaturated bonding groups per molecule. The crosslinking agent having two or more photo-polymerizable unsaturated bonding groups per molecule is preferably a (meth)acrylic compound. Examples thereof include ethylene glycol diacrylate, ethylene glycol dimethacrylate, polyethylene glycol diacrylate (the number of ethylene glycol units is 2 to 20), polyethylene glycol dimethacrylate (the number of ethylene glycol units is 2 to 20), poly(1,2-propylene glycol) diacrylate, poly(1,2-propylene glycol) dimethacrylate, 1,6-hexanediol diacrylate, neopentyl glycol diacrylate, pentaerythritol diacrylate, trimethylolpropane triacrylate, pentaerythritol triacrylate, dipentaerythritol hexaacrylate, tetramethylolpropane tetraacrylate, tetraethylene glycol diacrylate, 1,6-hexanediol dimethacrylate, neopentyl glycol dimethacrylate, pentaerythritol dimethacrylate, trimethylolpropane trimethacrylate, pentaerythritol trimethacrylate, dipentaerythritol hexamethacrylate, tetramethylolpropane tetramethacrylate, glycerol diacrylate, glycerol dimethacrylate, methylene bisacrylamide, N-methylol acrylamide, a methacrylic acid adduct of ethylene glycol diglycidyl ether, an acrylic acid adduct of glycerol diglycidyl ether, an acrylic acid adduct of bisphenol A diglycidyl ether, a methacrylic acid adduct of bisphenol A diglycidyl ether, and N,N'-bis (2-methacryloyloxyethyl) urea, although not limited thereto.

The formulation amount of the component (C) is preferably 1 to 100 parts by mass, more preferably 3 to 50 parts by mass, with respect to 100 parts by mass of the component (A'). When the amount is in the range of 1 to 100 parts by mass, an intended effect can be sufficiently obtained, and the development ability is not adversely affected. In addition, as a copolymerization monomer, one compound may be used, or a mixture of several compounds may be used.

The component (D) in the negative photosensitive resin composition according to the second embodiment is a solvent. The solvent of component (D) is not limited as long as it can dissolve the components (A'), (B), and (C). As the solvent of component (D), the same solvent as described in the first embodiment can be used.

The formulation amount of the component (D) is preferably 50 to 2,000 parts by mass, particularly preferably 100 to 1,000 parts by mass, with respect to 100 parts by mass of the total amount of the components (A'), (B), and (C).

The negative photosensitive resin composition according to the second embodiment may further contain other components besides the components (A'), (B), (C), and (D). Examples of the other components include the same materials as described in the first embodiment.

A negative photosensitive resin composition according to a third embodiment of the present invention contains:

(A') the polymer having the structural unit (6) or the polymer having the structural units (6) and (7);

(B') a photo acid generator;

(C') one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

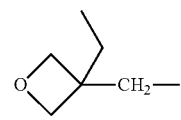

(C-1)

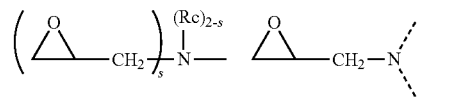

(C-2)

wherein the dotted line represents a bond, Rc represents a linear, branched, or cyclic alkyl group having 1 to 6 carbon atoms, and "s" represents 1 or 2; and (D) a solvent.

The component (A') in the negative photosensitive resin composition according to the third embodiment is the polymer having the structural unit (6) or the structural units (6) and (7), and the same polymer as described in the negative photosensitive resin composition according to the second embodiment can be suitably used.

The component (B') in the negative photosensitive resin composition according to the third embodiment is a photo acid generator. The photo acid generator may be a compound capable of generating an acid by exposure to light having a wavelength of 190 to 500 nm for serving as a curing catalyst. Examples thereof include onium salts, diazomethane derivatives, glyoxime derivatives, β-ketosulfone derivatives, disulfone derivatives, nitrobenzylsulfonate derivatives, sulfonate ester derivatives, imide-yl-sulfonate derivatives, oximesulfonate derivatives, iminesulfonate derivatives, and triazine derivatives.

Examples of the onium salt include a compound shown by the following general formula (20),

(20)

wherein $R_8$ represents an optionally substituted linear, branched, or cyclic alkyl group having 1 to 12 carbon atoms, an aryl group having 6 to 12 carbon atoms, or an aralkyl group having 7 to 12 carbon atoms; $M^+$ represents an iodonium ion or a sulfonium ion; K⁻ represents a non-nucleophilic counter ion; and "j" is 2 or 3.

As to $R_8$, examples of the alkyl group include a methyl group, an ethyl group, a propyl group, a butyl group, a cyclohexyl group, a 2-oxocyclohexyl group, a norbornyl group, and an adamantyl group. Examples of the aryl group include a phenyl group; alkoxyphenyl groups such as an o-, m-, or p-methoxyphenyl group, an o-, m-, or p-ethoxyphenyl group, and a m- or p-tert-butoxyphenyl group; and alkylphenyl groups such as a 2-, 3-, or 4-methylphenyl group, a 2-, 3-, or 4-ethylphenyl group, a 4-tert-butylphenyl group, a 4-butylphenyl group, and a dimethylphenyl group. Examples of the aralkyl group include a benzyl group and a phenethyl group.

Examples of the non-nucleophilic counter ion K⁻ include halide ions such as a chloride ion and a bromide ion; fluoroalkyl sulfonates such as triflate, 1,1,1-trifluoroethane sulfonate, and nonafluorobutanesulfonate; aryl sulfonates such as tosylate, benzenesulfonate, 4-fluorobenzenesulfonate, and 1,2,3,4,5-pentafluorobenzenesulfonate; and alkyl sulfonates such as mesylate and butanesulfonate.

Examples of the diazomethane derivative include a compound shown by the general formula (21),

(21)

wherein $R_9$ is the same or different and represents a linear, branched, or cyclic alkyl group or halogenated alkyl group having 1 to 12 carbon atoms, an aryl group or halogenated aryl group having 6 to 12 carbon atoms, or an aralkyl group having 7 to 12 carbon atoms.

As to $R_9$, examples of the alkyl group include a methyl group, an ethyl group, a propyl group, a butyl group, an amyl group, a cyclopentyl group, a cyclohexyl group, a norbornyl group, and an adamantyl group. Examples of the halogenated alkyl group include a trifluoromethyl group, a 1,1,1-trifluoroethyl group, a 1,1, 1-trichloroethyl group, and a nonafluorobutyl group. Examples of the aryl group include a phenyl group; alkoxyphenyl groups such as an o-, m-, or p-methoxyphenyl group, an o-, m-, or p-ethoxyphenyl group, and a m- or p-tert-butoxyphenyl group; and alkylphenyl groups such as a 2-, 3-, or 4-methylphenyl group, a 2-, 3-, or 4-ethylphenyl group, a 4-tert-butylphenyl group, a 4-butylphenyl group, and a dimethylphenyl group. Examples of the halogenated aryl group include a fluorophenyl group, a chlorophenyl group, and a 1,2,3,4,5-pentafluorophenyl group. Examples of the aralkyl group include a benzyl group and a phenethyl group.

Illustrative examples of the photo acid generator include onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl) diphenylsulfonium p-toluenesulfonate, bis(p-tert-butoxyphenyl)phenylsulfonium p-toluenesulfonate, tris(p-tert-butoxyphenyl) sulfonium p-toluenesulfonate, triphenylsulfonium nonafluolobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl) sulfonium trifluoromethanesulfonate, cyclohexylmethyl(2-oxocyclohexyl) sulfonium p-toluenesulfonate, dimethylphenylsulfonium trifuoromethanesulfonate, dimethylphenylsulfonium p-toluenesulfonate, dicyclohexylphenylsulfonium trifluoromethanesulfonate, dicyclohexylphenylsulfonium p-toluenesulfonate, and diphenyl(4-thiophenoxyphenyl) sulfonium hexafluoroantimonate; diazomethane derivatives such as bis(benzenesufonyl) diazomethane, bis(p-toluenesulfonyl) diazomethane, his (xylenesulfonyl) diazomethane, bis(cyclohexylsulfonyl) diazomethane, bis(cyclopentylsulfonyl) diazomethane, bis(n-butylsulfonyl) diazomethane, bis(isobutylsulfonyl) diazomethane, bis(sec-butylsulfonyl) diazomethane, bis(n-propylsulfonyl) diazomethane, bis(isopropylsulfonyl) diazomethane, bis(tert-butylsulfonyl) diazomethane, bis(n-amylsulfonyl) diazomethane, bis(isoamylsulfonyl) diazomethane, bis(sec-amylsulfonyl) diazomethane, bis (tert-amylsulfonyl) diazomethane, 1-cyclohexylsulfonyl-1-(tert-butylsulfonyl) diazomethane, 1-cyclohexylsulfonyl-1-(tert-amylsulfonyl) diazomethane, and 1-tert-amylsulfonyl-1-(tert-butylsulfonyl) diazomethane; glyoxime derivatives such as bis-o-(p-toluenesulfonyl)-α-dimethyl glyoxime, bis-o-(p-toluenesulfonyl)-α-diphenyl glyoxime, bis-o-(p-toluenesulfonyl)-α-dicyclohexyl, glyoxime, bis-o-(p-toluenesulfonyl)-2,3-pentanedione glyoxime, bis-(p-toluenesulfonyl)-2-methyl-3, 4-pentanedione glyoxime, bis-o-(n-butanesulfonyl)-α-dimethyl glyoxime, bis-o-(n-butanesulfonyl)-α-diphenyl glyoxime, bis-o-(n-butanesulfonyl)-α-dicyclohexyl glyoxime, bis-o-(n-butanesulfonyl)-2,3-pentanedione glyoxime, bis-o-(n-butanesulfonyl)-2-methyl-3, 4-pentanedione glyoxime, bis-o-(methanesulfonyl)-α-dimethyl glyoxime, bis-o-(trifluoromethanesufonyl)-α-dimethyl glyoxime, bis-o-(1,1, 1-trifluoroethanesulfonyl)-α-dimethylglyoxime, bis-o-(tert-butanesulfonyl)-α-di methyl glyoxime, bis-o-(perfluorooctanesulfonyl)-α-dimethyl glyoxime, bis-o-(cyclohexanesulfonyl)-α-dimethyl glyoxime, bis-o-(benzenesulfonyl)-α-dimethyl glyoxime, bis-o-(p-fluorobenzenesulfonyl)-α-dimethyl glyoxime, bis-o-(p-tert-butylbenzenesulfonyl)-α-dimethyl glyoxime, bis-o-(xylenesulfonyl)-α-dimethyl glyoxime, and bis-o-(camphersulfonyl)-α-dimethyl glyoxime; oxime sulfonate derivatives such as α-(benzenesulfoniumoxyimino)-4-methylphenylacetonitrile; β-keto sulfone derivatives such as 2-cyclohexylcarbonyl 2-(p-toluenesulfonyl) propane and 2-isopropylearbonyl-2-(p-toluenesulfonyl) propane; disulfone derivatives such as diphenyl disulfone and dicyclohexyl disulfone; nitrobenzyl sulfonate derivatives such as 2,6-dinitrobenzyl p-toluenesulfonate and 2,4-dinitrobenzyl p-toluenesulfonate; sulfonate ester derivatives such as 1,2, 3-tris(methanesulfonyloxy)benzene, 1,2,3-tris(trifluoromethanesulfonyloxy)benzene, and 1,2,3-tris(p-toluenesulfonyloxy)benzene; imide-yl-sulfonate derivatives such as phthalimide-yl-triflate, phthalimide-yl-tosylate, 5-norbornene 2,3-dicarboxyimide-yl-triflate, 5-norbornene 2,3-dicarboxyimide-yl-tosylate, 5-norbornene 2,3-dicarboxyimide-yl-n-butylsulfonate, and n-trifluoromethylsulfonyloxy naphthylimide; iminosulfonates such as (5-(4-methylphenyl) sulfonyloxyimino-5H-thiophene-2-ylidene)-(2-methylphenyl)acetonitrile and (5-(4-(4-methylphenylsulfonyloxy) phenylsulfonyloxyimino)-5H-thiophene-2-ylidene)-(2-methylphenyl)acetonitrile; and 2-methyl-2 [(4-methylphenyl) sulfonyl]-1-[(4-methylthio)phenyl]-1-propane. Among them, imide-yl-sulfonates, iminosulfonates, and oxime sulfonates are preferably used.

These photo acid generators may be used alone or in combination of two or more kinds.

The formulation amount of the photo acid generator is preferably 0.05 to 20 parts by mass, particularly preferably 0.2 to 5 parts by mass, with respect to 100 parts by mass of the component (A') in the negative photosensitive resin composition according to the third embodiment of the present invention in view of light absorption of the photo acid generator itself and photo-curability of a thick film.

The component (C') in the negative photosensitive resin composition according to the third embodiment is one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

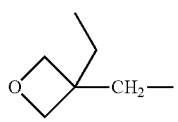
(C-1)

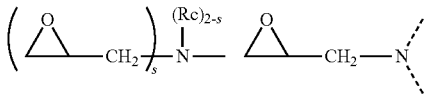
(C-2)

wherein the dotted line represents a bond, Rc represents a linear, branched, or cyclic alkyl group having 1 to 6 carbon atoms, and "s" represents 1 or 2.

Examples of the amino condensate modified with formaldehyde or formaldehyde-alcohol include melamine condensates modified with formaldehyde or formaldehyde-alcohol and urea condensates modified with formaldehyde or formaldehyde-alcohol.

The melamine condensate modified with formaldehyde or formaldehyde-alcohol can be prepared by the following procedure, for example. First, a melamine monomer is modified with formalin into a methylol form, and optionally, the resultant compound is further modified with alcohol into an alkoxy form, according to a known method, to obtain a modified melamine shown by the following general formula (22). The alcohol is preferably a lower alcohol, for example, an alcohol having 1 to 4 carbon atoms.

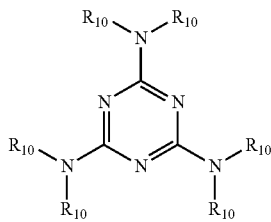
(22)

wherein each $R_{10}$ is the same or different and represents a methylol group, an alkoxymethyl group containing an alkoxy group having 1 to 4 carbon atoms, or a hydrogen atom, provided that one or more of $R_{10}$ is a methylol group or an alkoxymethyl group.

Examples of $R_{10}$ include a methylol group, and alkoxymethyl groups such as a methoxymethyl group and an ethoxymethyl group, and a hydrogen atom.

Illustrative examples of the modified melamine shown by the general formula (22) include trimethoxymethyl monomethylol melamine, dimethoxymethyl monomethylol melamine, trimethylol melamine, hexamethylol melamine, and hexamethoxymethylol melamine.

Then, the modified melamine shown by the formula (22) or a multimeric compound thereof (e.g. an oligomer such as a dimer and a trimer) is polymerized by addition condensation with formaldehyde until a desired molecular weight is achieved according to a known method, to obtain the melamine condensate modified with formaldehyde or formaldehyde-alcohol.

The urea condensate modified with formaldehyde or formaldehyde-alcohol can be prepared by modifying a urea condensate having a desired molecular weight with formaldehyde into a methylol form, and optionally, further modifying the resultant compound with alcohol into an alkoxy form, according to a known method.

Illustrative examples of the urea condensate modified with formaldehyde or formaldehyde-alcohol include a methoxymethylated urea condensate, an ethoxymethylated urea condensate, and a propoxymethylated urea condensate.

These modified melamine condensates and modified urea condensates may be used alone or in combination of two or more kinds.

Examples of the phenol compound having on average two or more methylol groups or alkoxymethylol groups per molecule include (2-hydroxy-5-methyl)-1,3-benzenedimethanol, 2,2',6,6'-tetramethoxymethyl bisphenol A, and compounds shown by the formulae (C-3) to (C-7).

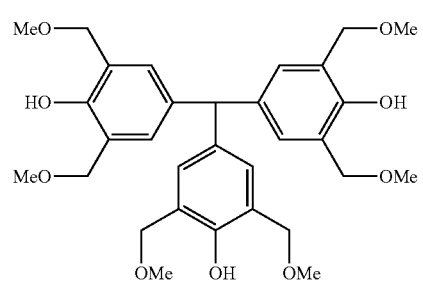
C-3

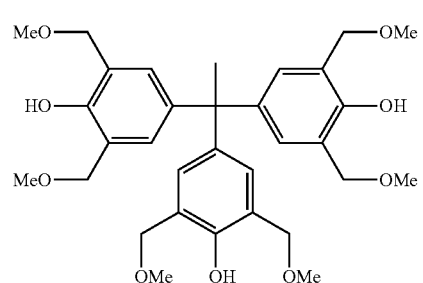
C-4

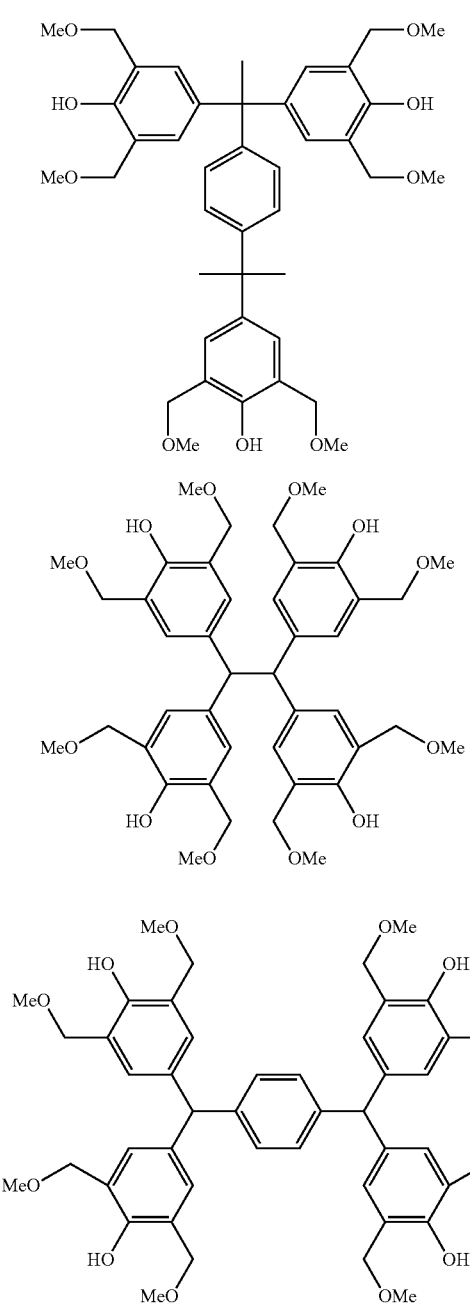

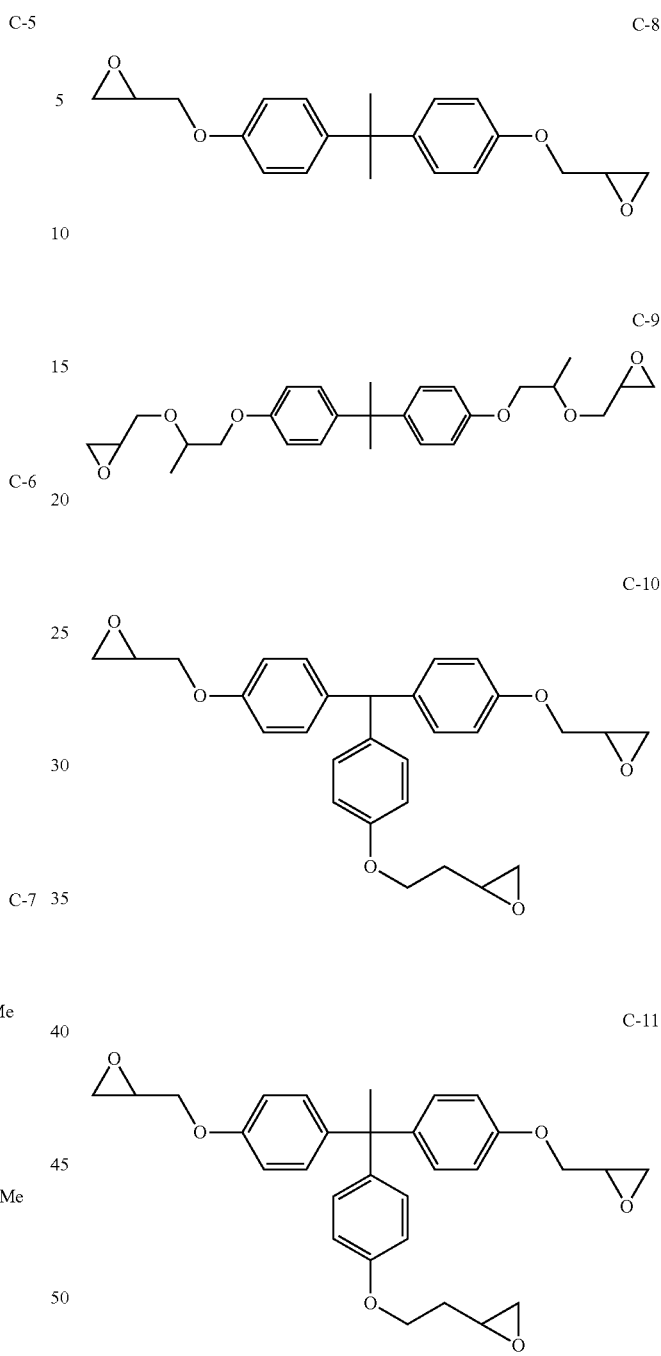

The above crosslinking agents may be used alone or in combination of two or more kinds.

Examples of the polyhydric phenol compound in which a hydrogen atom of a phenolic hydroxyl group is substituted with a glycidyl group include compounds obtained by reacting a hydroxyl group of bisphenol A, tris(4-hydroxyphenyl)methane, or 1,1,1-tris(4-hydroxyphenyl)ethane with epichlorohydrin in the presence of a base catalyst. More specifically, the polyhydric phenol compound in which a hydrogen atom of a phenolic hydroxyl group is substituted with a glycidyl group is preferably, for example, a compounds shown by the formulae (C-8) to (C-14).

-continued

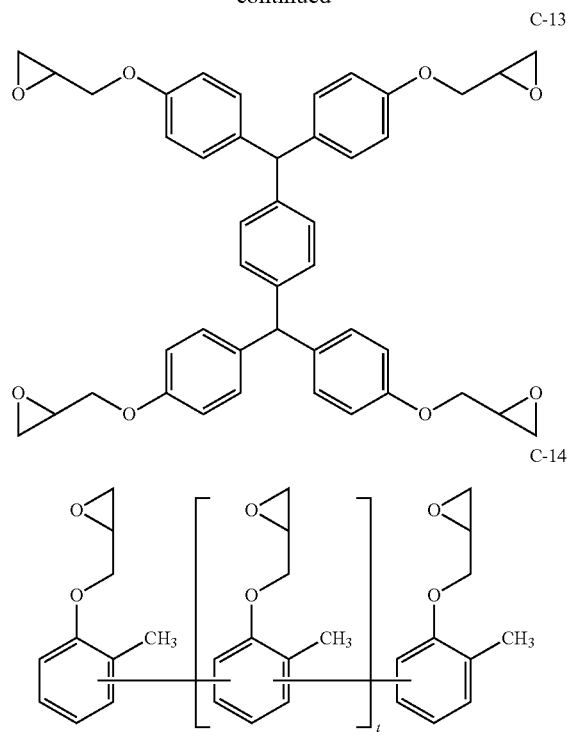
C-13

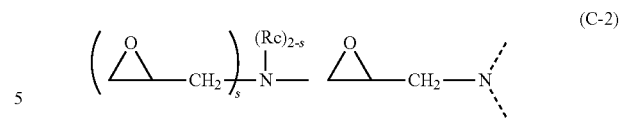
(C-2)

wherein the dotted line represents a bond; Rc represents a linear, branched, or cyclic alkyl group having 1 to 6 carbon atoms; and "s" represents 1 or 2,

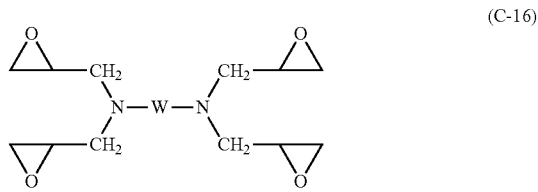
(C-16)

wherein W represents a linear, branched, or cyclic alkylene group having 2 to 12 carbon atoms or a divalent aromatic group.

Examples of the compound shown by the formula (C-16) include compounds shown by the formulae (C-17) to (C-20).

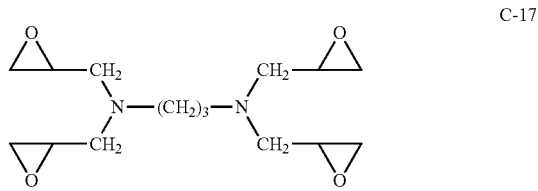
C-17

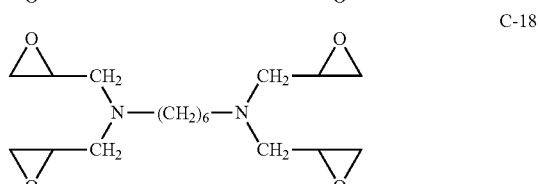
C-18

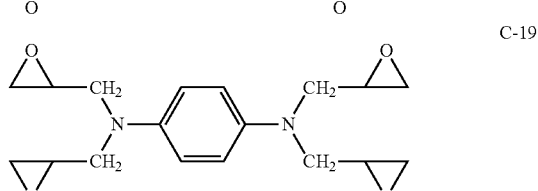
C-19

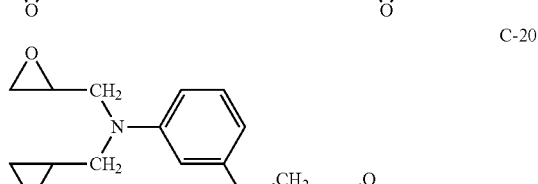
C-20

C-14 wherein 2≤t≤3.

The polyhydric phenol compound in which a hydrogen atom of a phenolic hydroxyl group is substituted with a glycidyl group to be used as the crosslinking agent may be one kind or two kinds.

Examples of the polyhydric phenol compound in which a hydrogen atom of a phenolic hydroxyl group is substituted with a substituent shown by the formula (C-1) include a compound having two substituents as shown by the formula (C-15),

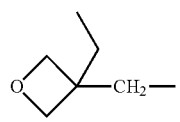
(C-1)

wherein the dotted line represents a bond,

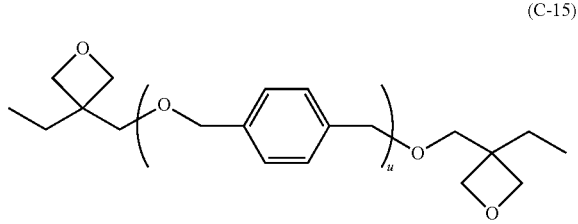
(C-15)

wherein 1≤u≤3.

Examples of the compound containing two or more nitrogen atoms bonded to a glycidyl group as shown by the formula (C-2) include compounds shown by the following formula (C-16), Alternatively, a compound shown by the following formula (C-21) may be suitably used as the compound containing two or more nitrogen atoms bonded to a glycidyl group as shown by the formula (C-2).

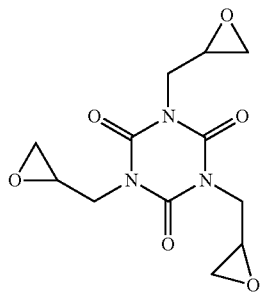

C-21

The compound containing two or more nitrogen atoms bonded to a glycidyl group as shown by the formula (C-2) to be used as the crosslinking agent may be one kind or two kinds.

The component (C'), which serves to initiate curing reaction with the inventive polyimide precursor polymer, not only facilitates pattern formation but also improves the strength of a cured product. The weight average molecular weight of the component (C') is preferably 150 to 10,000, particularly preferably 200 to 3,000, in view of photo-curability and heat resistance.

The formulation amount of the component (C') is preferably 0.5 to 50 parts by mass, particularly preferably 1 to 30 parts by mass, with respect to 100 parts by mass of the component (A') in the negative photosensitive resin composition according to the third embodiment of the present invention.

Preferable examples of the solvent of component (D) in the negative photosensitive resin composition according to the third embodiment are the same as in the negative photosensitive resin composition according to the first and second embodiments.

The negative photosensitive resin composition according to the third embodiment also may further contain other components besides the components (A'), (B'), (C'), and (D). Examples of the other components include (F) a sensitizer, an adhesion assistant, a polymerization inhibitor for enhancing storage stability, and (G) a surfactant for improving coating property. As (F) the sensitizer and (G) the surfactant, the above-described compounds can be suitably used.

Moreover, the negative photosensitive resin composition according to the third embodiment also may further contain (H) a basic compound, if necessary. For the basic compound is suited a compound that can reduce diffusion rate at which acids generated from the photo acid generator are diffused into a resist film. Blending the basic compound enhances resolution, reduces the change of sensitivity after exposure, decreases dependence on a substrate and an environment, and thus improves exposure margin, pattern profile, and the like.

Examples of the basic compound include primary, secondary, and tertiary aliphatic amines, mixed amines, aromatic amines, heterocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, nitrogen-containing alcoholic compounds, amide derivatives, imide derivatives, and compounds shown by the following general formula (23), $$N(\alpha)_q(\beta)_{3-q} \quad (23)$$

In the formula, "q" represents 1, 2, or 3; the side chain α is the same or different and represents any of substituents shown by the following general formulae (24) to (26); and the side chain β is the same or different and represents a hydrogen atom or a linear, branched, or cyclic alkyl group having 1 to 20 carbon atoms and optionally containing an ether bond or a hydroxyl group. The side chains α may be bonded with each other to form a ring.

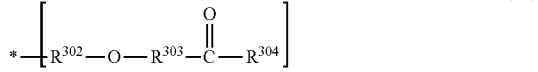

wherein $R^{300}$, $R^{302}$, and $R^{305}$ represent a linear or branched alkylene group having 1 to 4 carbon atoms; $R^{301}$ and $R^{304}$ represent a hydrogen atom, or a linear, branched, or cyclic alkyl group having 1 to 20 carbon atoms and optionally containing one or more groups selected from a hydroxyl group, an ether bond, an ester bond, and a lactone ring; $R^{303}$ represents a single bond or a linear or branched alkylene group having 1 to 4 carbon atoms; and $R^{306}$ represents a linear, branched, or cyclic alkyl group having 1 to 20 carbon atoms and optionally containing one or more groups selected from a hydroxyl group, an ether bond, an ester bond, and a lactone ring. * represents a bond terminal.

Examples of the primary aliphatic amine include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of the secondary aliphatic amine include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylene diamine, N,N-dimethylethylene diamine, and N,N-dimethyltetraethylene pentamine.

Examples of the tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylene diamine, N,N,N',N'-tetramethylethylene diamine, and N,N,N',N'-tetramethyltetraethylene pentamine.

Examples of the mixed amines include dimethylethylamine, methylethylpropylamine, benzylamine, phenethylamine, and benzyldimethylamine.

Examples of the aromatic amines and the heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl) amine, metnyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(i-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of the nitrogen-containing compound having a carboxyl group include amino benzoic acid, indole carboxylic acid, and amino acid derivatives (e.g., nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, and methoxy alanine).

Examples of the nitrogen-containing compound having a sulfonyl group include 3-pyridinesulfonic acid and pyridinium p-toluenesulfonate.

Examples of the nitrogen-containing compound having a hydroxyl group, the nitrogen-containing compound having a hydroxyphenyl group, and the nitrogen-containing alcoholic compound include 2-hydroxy pyridine, amino cresol, 2,4-quinoline diol, 3-indole methanol hydrate, monoethanol amine, diethanol amine, triethanol amine, N-ethyl diethanol amine, N,N-diethyl ethanol amine, triisopropanol amine, 2,2'-imino diethanol, 2-amino ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy) ethyl]piperazine, piperidine ethanol, 1-(2-hydroxyethyl)pyrrolidine, 1-(2-hydroxyethyl)-2-pyrrolidinone, 3-piperidino-1,2-propane diol, 3-pyrrolidino-1,2-propane diol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl) isonicotine amide.

Examples of the amide derivative include formamide, N-methyl formamide, N,N-dimethyl formamide, acetamide, N-methyl acetamide, N,N-dimethyl acetamide, propione amide, and benzamide.

Examples of the imide derivative include phthalimide, succinimide, and maleimide.

Examples of the compound shown by the general formula (23) include tris[2-(methoxymethoxy)ethyl] amine, tris[2-(2-methoxyethoxy)ethyl] amine, tris[2-(2-methoxyethoxymethoxy)ethyl] amine, tris[2-(1-methoxyethoxy)ethyl] amine, tris[2-(1-ethoxyethoxy)ethyl]amine, tris[2-(1-ethoxypropoxy)ethyl] amine, tris[2-(2-(2-hydroxyethoxy)ethoxy)ethyl] amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl) amine, tris(2-acetoxyethyl) amine, tris(2-propionyloxyethyl) amine, tris(2-butyryloxyethyl) amine, tris(2-isobutyryloxyethyl) amine, tris(2-valeryloxyethyl) amine, tris(2-pivaloyloxyethyl) amine, N,N-bis(2-acetoxyethyl) 2-(acetoxyacetoxy)ethyl amine, tris(2-methoxycarbonyloxyethyl) amine, tris(2-tert-butoxycarbonyloxyethyl) amine, tris[2-(2-oxopropoxy)ethyl]amine, tris[2-(methoxycarbonylmethyl)oxyethyl] amine, tris[2-(tert-butoxycarbonylmethyloxy)ethyl] amine, tris[2-(cyclohexyloxycarbonylmethyloxy)ethyl] amine, tris(2-methoxycarbonylethyl) amine, tris(2-ethoxycarbonylethyl) amine, N,N-bis(2-hydroxyethyl) 2-(methoxycarbonyl)ethyl amine, N,N-bis(2-acetoxyethyl) 2-(methoxycarbonyl)ethyl amine, N,N-bis(2-hydroxyethyl) 2-(ethoxycarbonyl)ethyl amine, N,N-bis(2-acetoxyethyl) 2-(ethoxycarbonyl)ethyl amine, N,N-bis(2-hydroxyethyl) 2-(2-methoxyethoxycarbonyl)ethyl, amine, N,N-bis(2-acetoxyethyl) 2-(2-methoxyethoxycarbonyl)ethyl amine, N,N-bis(2-hydroxyethyl) 2-(2-hydroxyethoxycarbonyl)ethyl amine, N,N-bis (2-acetoxyethyl) 2-(2-acetoxyethoxycarbonyl)ethyl amine, N,N-bis(2-hydroxyethyl) 2-[(methoxycarbonyl) methoxycarbonyl]ethyl amine, N,N-bis(2-acetoxyethyl) 2-[(methoxycarbonyl) methoxycarbonyl]ethyl amine, N,N-bis(2-hydroxyethyl) 2-(2-oxopropoxycarbonyl)ethyl amine, N,N-bis(2-acetoxyethyl) 2-(2-oxopropoxycarbonyl)ethyl amine, N,N-bis(2-hydroxyethyl) 2-(tetrahydrofurfuryloxycarbonyl)ethyl amine, N,N-bis(2-acetoxyethyl) 2-(tetrahydrofurfuryloxycarbonyl)ethyl amine, N,N-bis(2-hydroxyethyl) 2-[(2-oxotetrahydrofuran-3-yl)oxycarbonyl] ethyl amine, N,N-bis(2-acetoxyethyl) 2-[(2-oxotetrahydrofuran-3-yl) oxycarbonyl]ethyl amine, N,N-bis (2-hydroxyethyl) 2-(4-hydroxybutoxycarbonyl)ethyl amine, N,N-bis(2-formyloxyethyl) 2-(4-formyloxybutoxycarbonyl) ethyl amine, N,N-bis(2-formyloxyethyl) 2-(2-formyloxyethoxycarbonyl)ethyl amine, N,N-bis(2-methoxyethyl) 2-(methoxycarbonyl)ethyl amine, N-(2-hydroxyethyl) bis [2-(methoxycarbonyl)ethyl] amine, N-(2-acetoxyethyl) bis [2-(methoxycarbonyl)ethyl] amine, N-(2-hydroxyethyl) bis [2-(ethoxycarbonyl)ethyl] amine, N-(2-acetoxyethyl) bis[2-(ethoxycarbonyl)ethyl] amine, N-(3-hydroxy-1-propyl) bis [2-(methoxycarbonyl)ethyl] amine, N-(3-acetoxy-1-propyl) bis[2-(methoxycarbonyl)ethyl] amine, N-(2-methoxyethyl) bis[2-(methoxycarbonyl)ethyl] amine, N-butyl bis[2-(methoxycarbonyl)ethyl] amine, N-butyl bis[2-(2-methoxyethoxycarbonyl)ethyl] amine, N-methyl bis(2-acetoxyethyl) amine, N-ethyl bis(2-acetoxyethyl) amine, N-methyl bis(2-pivaloyloxyethyl) amine, N-ethyl bis[2-(methoxycarbonyloxy)ethyl] amine, N-ethyl bis[2-(tert-butoxycarbonyloxy) ethyl] amine, tris(methoxycarbonylmethyl) amine, tris (ethoxycarbonylmethyl) amine, N-butyl bis (methoxycarbonylmethyl) amine, N-hexyl bis (methoxycarbonylmethyl) amine, and β-(diethylamino)-δ-valerolactone; however, the compound is not limited thereto. These basic compounds may be used alone or in combination of two or more kinds.

The formulation amount of the basic compound is preferably 0 to 3 parts by mass, particularly preferably 0.01 to 1 part by mass, with respect to 100 parts by mass of the component (A') in the negative photosensitive resin composition according to the third embodiment of the present invention, in view of sensitivity.

[Positive Photosensitive Resin Composition]

Next, explanation will be given for the positive photosensitive resin composition, using the inventive polyimide precursor polymer as a base resin, which is capable of forming a pattern by development with alkaline aqueous solution.

The inventive positive photosensitive resin composition contains:

(A') the polymer having the structural unit (6) or the polymer having the structural units (6) and (7);

(B") a compound having a quinonediazide structure for serving as a photosensitive agent capable of generating an acid by light and increasing a dissolution rate in an alkaline aqueous solution;

(C") one or two or more crosslinking agents selected from a crosslinking agent having two or more photo-polymerizable unsaturated bonding groups per molecule, an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

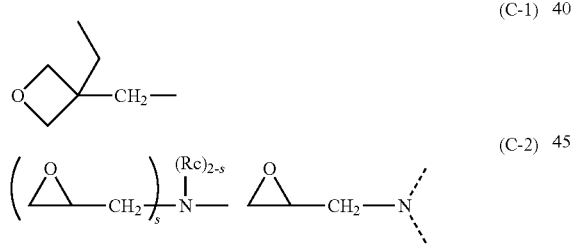

wherein the dotted line represents a bond, Rc represents a linear, branched, or cyclic alkyl group having 1 to 6 carbon atoms, and "s" represents 1 or 2; and (D) a solvent.

The polymer used as the component (A') in the inventive positive photosensitive resin composition contains a hexafluoroisopropanol group. In other words, this polymer contains an organic group corresponding to the general formula (2) (an organic group $R_1$ in the general formula (6)). Introduction of the hexafluoroisopropanol group into the polymer allows the polymer to dissolve in a widely used organic solvent and to form a composition with a widely used organic solvent (D). The same explanation is applied to the negative photosensitive resin composition, as described above.

In view of alkali-solubility, the rate of the hexafluoroisopropanol group to be introduced into the component (A') is preferably 0.15 mol to 0.58 mol, more preferably 0.20 mol to 0.30 mol, most preferably 0.25 mol to 0.30 mol, with respect to 100 g of the component (A'). When the introduction rate of the hexafluoroisopropanol group is 0.15 mol or more with respect to 100 g of the component (A'), a desired alkali dissolution rate can be obtained with respect to an alkaline developer, and failure at pattern opening and scum in pattern bottom are not caused in patterning, thus preventing reduction in resolution. On the other hand, possible amount of the hexafluoroisopropanol group that can be introduced into 100 g of the component (A') is 0.58 mol in design of the inventive polyimide precursor polymer. This amount enables the highest solubility in an alkaline developer. However, after patterning of the inventive photosensitive resin composition, the polyimide precursor structural unit of the inventive polyimide precursor polymer undergoes imidization ring-closure reaction by heating for post-curing. At this time, an organic group having the introduced hexafluoroisopropanol group is eliminated and removed from the system, and thus the thickness of the formed film is reduced. Thus, the introduction amount of the hexafluoroisopropanol group is preferably 0.30 mol or less. The same explanation is applied to the negative photosensitive resin composition, as described above.

The component (B") in the inventive positive photosensitive resin composition, which is a photosensitive agent capable of generating an acid by light and increasing a dissolution rate in an alkaline aqueous solution, is a compound having a quinonediazide structure. The component (B") may be a compound having a 1,2-naphthoquinone diazide sulfonyl group in its molecule.

Examples of the compound having a 1,2-naphthoquinone diazide sulfonyl group in its molecule include compounds having a 1,2-naphthoquinone diazide sulfonyl group shown by the following general formula (30) or (31).

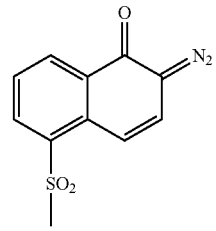

(30)

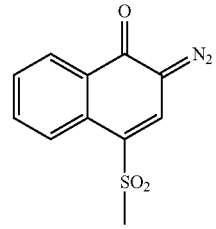

(31)

Illustrative examples of a preferable parent compound into which the 1,2-naphthoquinone diazide sulfonyl group is introduced include trihydroxybenzophenone, tetrahydroxybenzophenone, a ballast molecule having a phenolic hydroxyl group as shown by the following general formula (32), and a novolac resin having a repeating unit shown by the following formula (37) with a weight average molecular weight of 2,000 to 20,000, preferably 3,000 to 10,000. That is, a compound obtained by substituting a hydrogen atom of a hydroxyl group of the following resin or compound having the phenolic hydroxyl group with a 1,2-naphthoquinone diazide sulfonyl group is preferably used as the component (B").

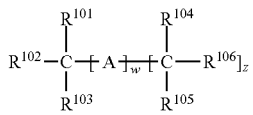
(32)

In the above formula, $R^{101}$ to $R^{106}$ independently represent a hydrogen atom, a methyl group, a group shown by the following formula (33), or a group shown by the following formula (34). "w" represents an integer of 0 to 2 and "z" represents an integer of 0 to 2, provided that when "z" is 0, "w" is 1 or 2. When "z" is 0 and "w" is 1, A is a hydrogen atom, a methyl group, or a group shown by the formula (33). When "z" is 0 and "w" is 2, one A is a methylene group or a group shown by the formula (35) and the other A is a hydrogen atom, a methyl group, or a group shown by the formula (33). When "z" is 1, A is a methylene group or a group shown by the following formula (35). When "z" is 2 and "w" is 1, A is a methine group or a group shown by the following formula (36). When "z" is 2 and "w" is 2, one A is a methylene group or a group shown by the formula (35) and the other A is a methine group or a group shown by the formula (36).

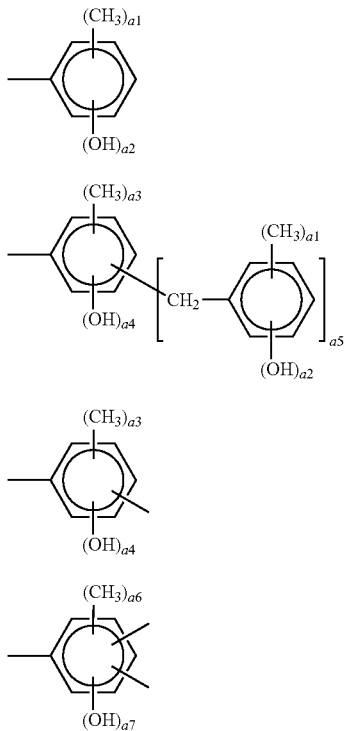

wherein a1, a2, a3, a4, a5, a6, a7 each represent an integer of 0 to 3 and satisfy a1+a2≤5, a3+a4≤4, a6+a7≤3.

In this case, the low nuclear compound (ballast molecule) shown by the formula (32) is preferably designed such that the number of benzene rings is 2 to 20, more preferably 2 to 10, much more preferably 3 to 6, and a ratio of the number of benzene rings to the number of phenolic hydroxyl groups ranges from 0.5 to 2.5, more preferably from 0.7 to 2.0, much more preferably from 0.8 to 1.5.

Examples of the low nuclear compound (ballast molecule) include the following compounds.

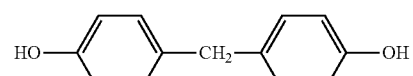
(B-1)

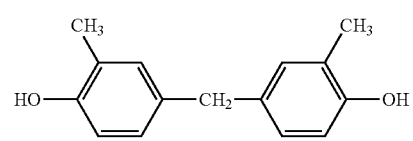
(B-2)

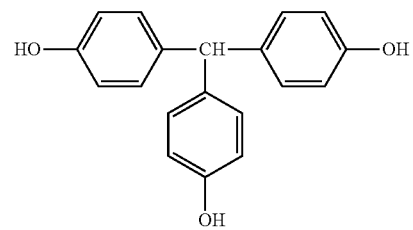
(B-3)

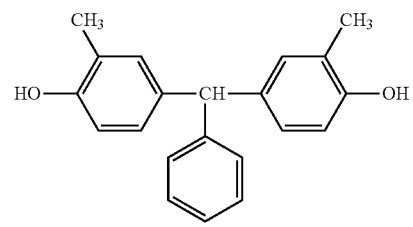
(B-4)

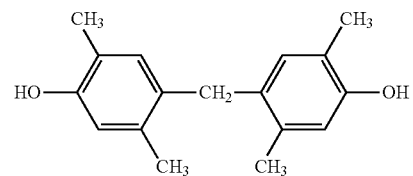
(B-5)

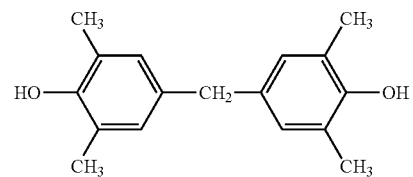
(B-6)

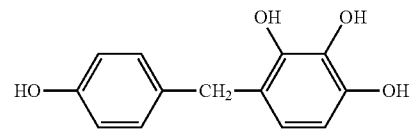
(B-7)

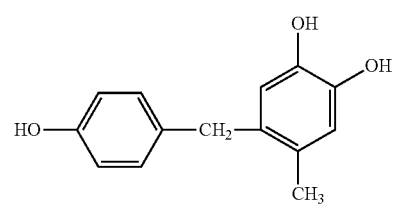
(B-8)

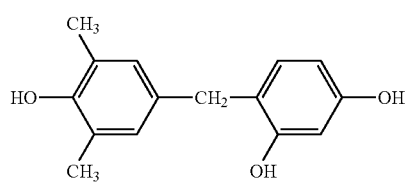
(B-9)
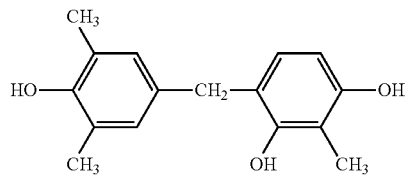
(B-10)
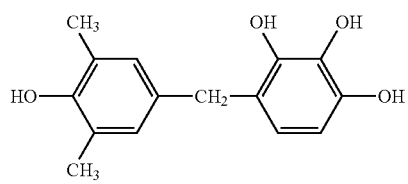
(B-11)
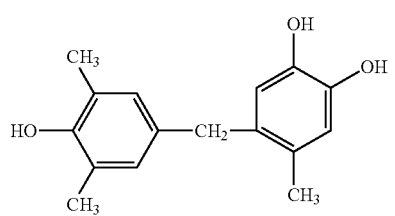
(B-12)
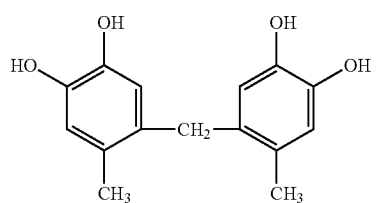
(B-13)
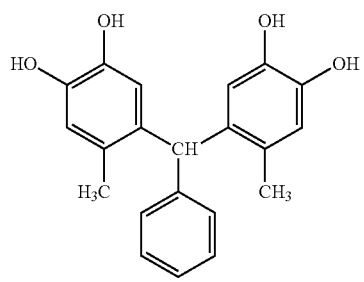
(B-14)
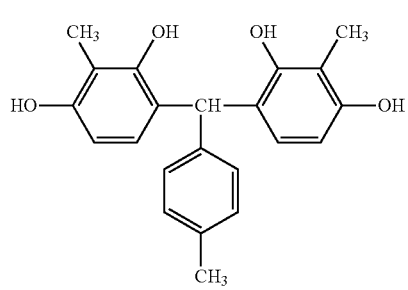
(B-15)
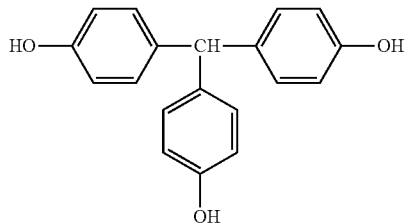
(B-16)
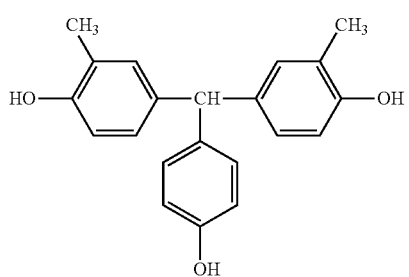
(B-17)
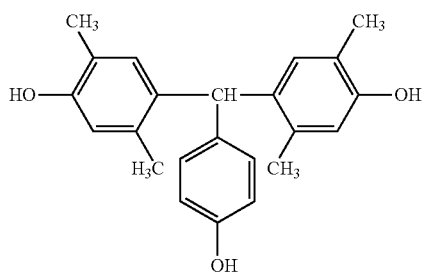
(B-18)
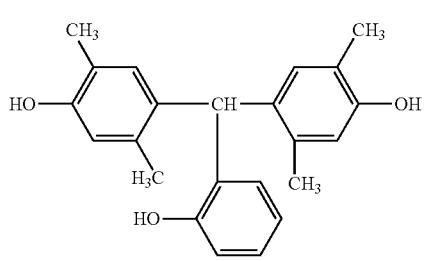
(B-19)
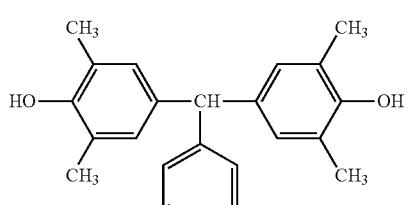
(B-20)
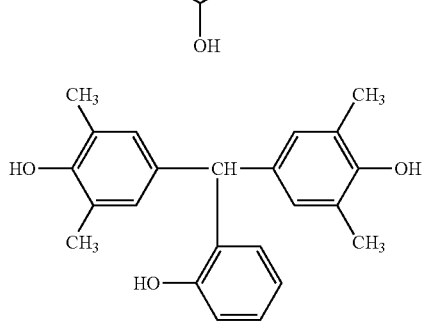
(B-21)

(B-22) 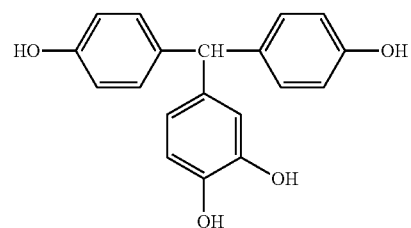
(B-23) 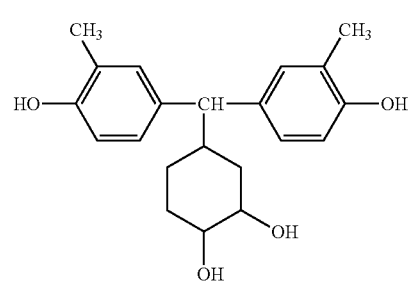
(B-24) 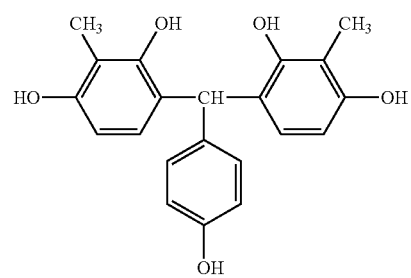
(B-25) 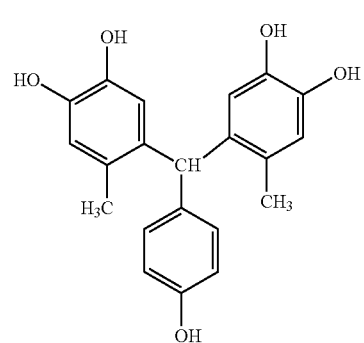
(B-26) 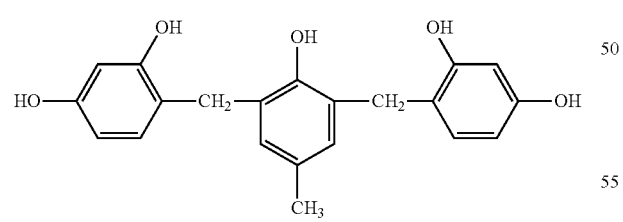
(B-27) 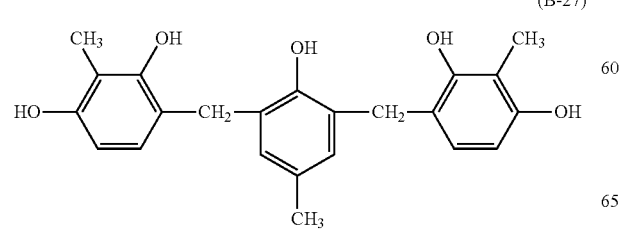
(B-28) 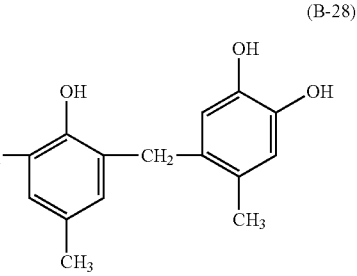
(B-29) 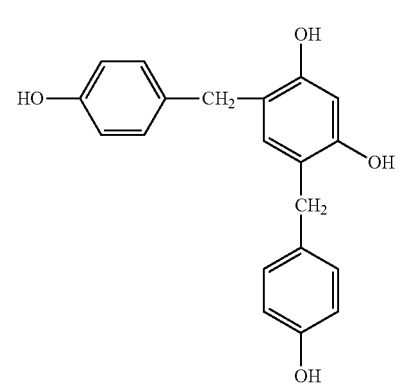
(B-30) 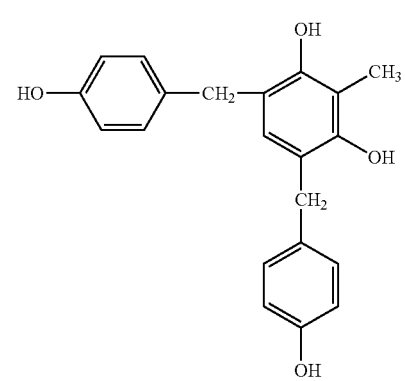
(B-31) 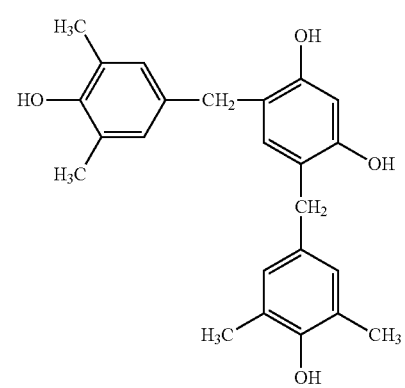

(B-32)
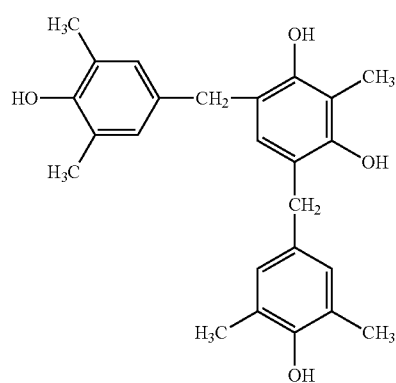
(B-33)
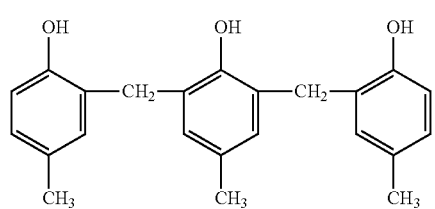
(B-34)
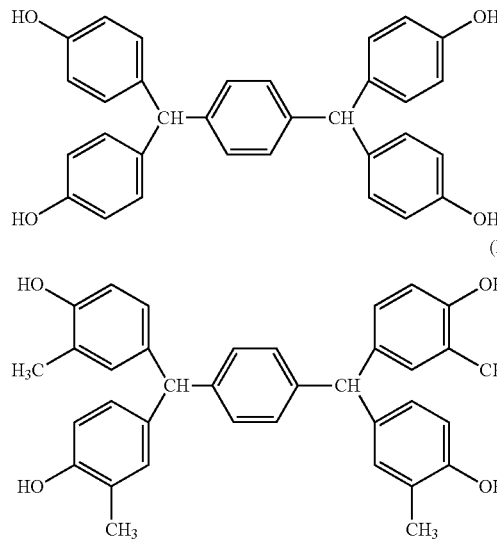
(B-35)
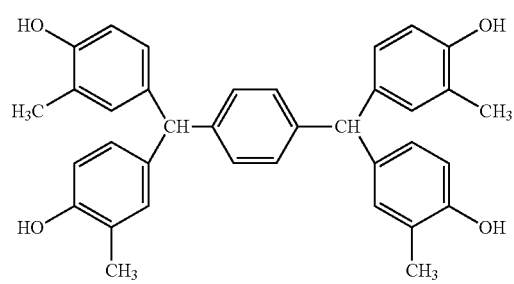
(B-36)
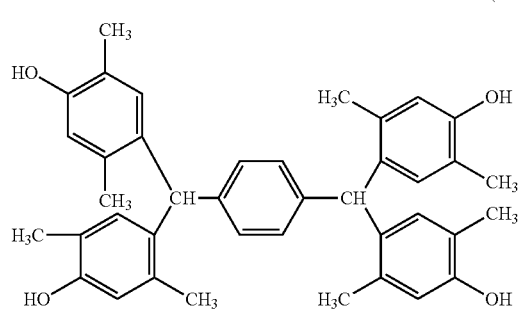
(B-37)
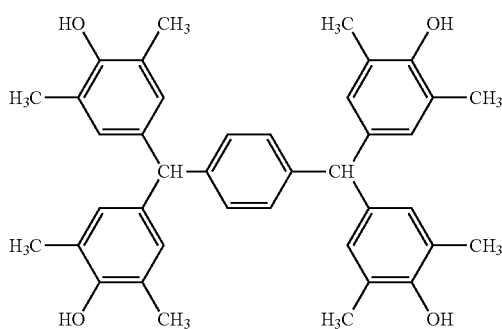
(B-38)
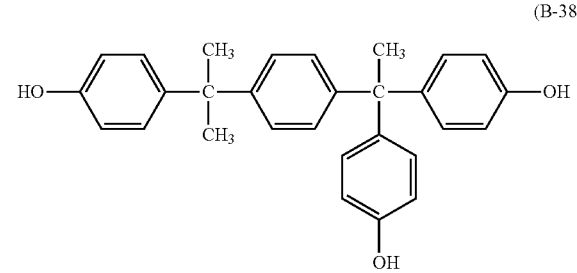
(B-39)
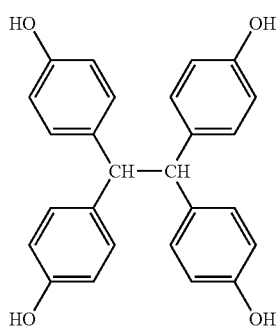
(B-40)
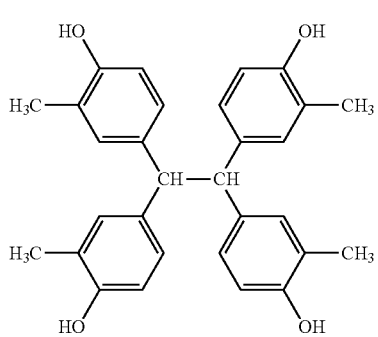
(B-41)
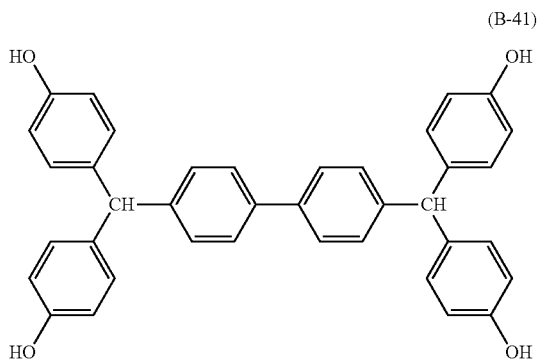

(B-42)

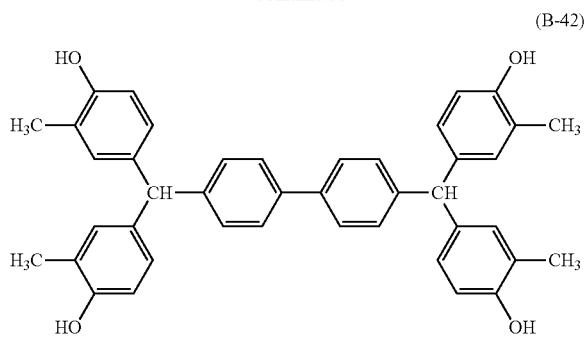

(B-43)

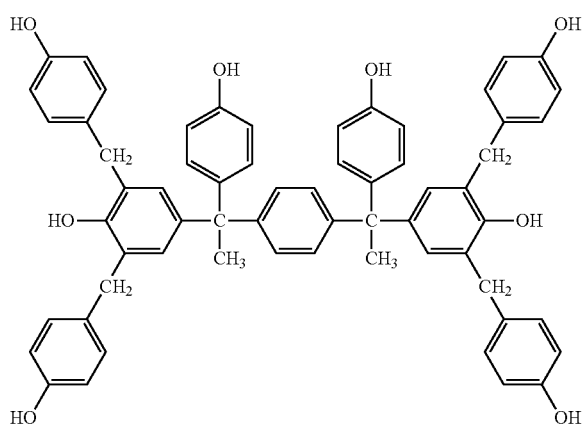

(B-44)

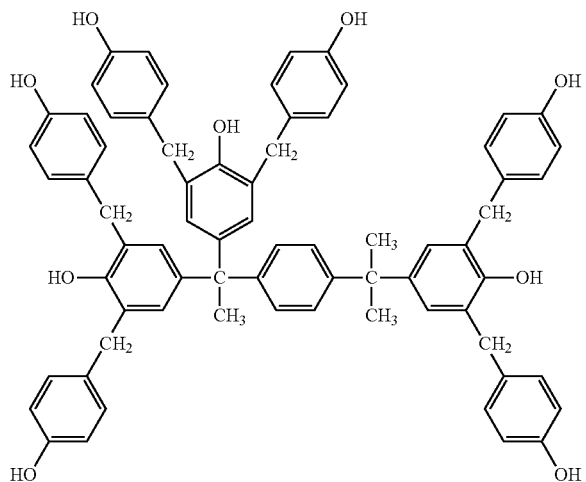

Among the low nuclear compounds (ballast molecules) shown above, (B-3), (B-29), (B-33), and (B-38) are preferable, and a compound obtained by substituting a hydrogen atom of a phenolic hydroxyl group of these ballast molecules with a 1,2-naphthoquinone diazide sulfonyl group is preferably used for the component (B″) in the inventive positive photosensitive resin composition.

(37)

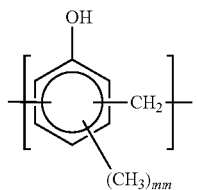

wherein mm represents an integer of 0 to 3.

The novolac resin having the repeating unit shown by the formula (37) can be synthesized by condensation of a phenol shown by the following formula (38), specifically, at least one phenol compound selected from o-cresol, m-cresol, p-cresol, and 3,5-xylenol, with an aldehyde according to a usual method.

(38)

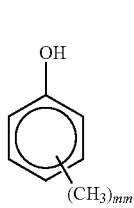

wherein mm represents an integer of 0 to 3.

Examples of the aldehyde used in this reaction include formaldehyde, paraformaldehyde, acetaldehyde, and benzaldehyde, and formaldehyde is preferable.

The mole ratio of the aldehyde to the phenol shown by the formula (38) preferably ranges from 0.2 to 2, more preferably from 0.3 to 2.

A preferable method for introducing a 1,2-naphthoquinone diazide sulfonyl group into the parent compound is dehydrochlorination condensation reaction of 1,2-naphthoquinone diazide sulfonyl chloride with phenolic hydroxyl groups in the presence of a base catalyst. In the case that the ballast molecule shown by the formula (32), trihydroxy benzophenone, or tetrahydroxy benzophenone is used, a hydrogen atom of its phenolic hydroxyl group is preferably substituted with a 1,2-naphthoquinone diazide sulfonyl group in a proportion of 1.0 to 100 mol %, more preferably 50 to 100 mol %. In the case that the novolac resin shown by the formula (37) is used, a hydrogen atom of its phenolic hydroxyl group is preferably substituted with 1,2-naphthoquinone diazide sulfonyl group in a proportion of 2 to 50 mol %, more preferably 3 to 27 mol %.

The adding amount of the component (B″) is preferably 1 to 50 parts by mass, more preferably 10 to 40 parts by mass, with respect to 100 parts by bass of the component (A′). The component (B″) to be used may be one kind or a combination of two or more kinds.

When such component (B″) is blended, the solubility in an aqueous alkaline solution before exposure is decreased due to the effect of dissolution inhibition by the component (B″), and thus the system becomes alkali-insoluble. On the other hand, once exposure is carried out, the component (B″) generates an acid by light and increases the dissolution rate in an aqueous alkaline solution, and thus the system becomes alkali-soluble.

That is, when an aqueous alkaline solution is used as a developer, an exposed part dissolves in the developer, while an unexposed part does not dissolve therein. This allows a positive pattern to be formed.

The component (C") in the inventive positive photosensitive resin composition is one or two or more crosslinking agents selected from a crosslinking agent having two or more photo-polymerizable unsaturated bonding groups per molecule, an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the formula (C-1), and a compound containing two or more nitrogen atoms bonded to a glycidyl group as shown by the formula (C-2).

Preferable examples of the crosslinking agent having two or more photo-polymerizable unsaturated bonding groups per molecule include the same compounds as in the component (C) in the negative photosensitive resin composition according to the second embodiment, described above. The formulation amount of the crosslinking agent having two or more photo-polymerizable unsaturated bonding groups per molecule is preferably 1 to 100 parts by mass, more preferably 3 to 50 parts by mass, with respect to 100 parts by mass of the inventive polyimide precursor polymer. When the amount is in the range of 1 to 100 parts by mass, an intended effect can be sufficiently obtained, and the development ability is not adversely affected. In addition, as a copolymerization monomer, one compound may be used, or a mixture of several compounds may be used.

Preferable examples of the amino condensate modified with formaldehyde or formaldehyde-alcohol, the phenol compound having on average two or more methylol groups or alkoxymethylol groups per molecule, the polyhydric phenol compound in which a hydrogen atom of a phenolic hydroxyl group is substituted with a glycidyl group, the polyhydric phenol compound in which a hydrogen atom of a phenolic hydroxyl group is substituted with a substituent shown by the formula (C-1), and the compound containing two or more nitrogen atoms bonded to a glycidyl group as shown by the formula (C-2) also include the same as the component (C') in the negative photosensitive resin composition according to the third embodiment, described above. These crosslinking agents, which serve to initiate curing reaction with the inventive polyimide precursor polymer, not only facilitate pattern formation but also improve the strength of a cured product. The weight average molecular weight of the crosslinking agents is preferably 150 to 10,000, particularly preferably 200 to 3,000, in view of photo-curability and heat resistance.

The component (C") is blended in order to make thermal crosslinking reaction with the component (A') progress in a step of baking and post-curing a film at 100 to 300° C. after patterning, thereby improving mechanical strength, chemical resistance, and adhesiveness of the pattern or the film.

Preferable examples of the solvent of component (D) in the inventive positive photosensitive resin composition are the same as in the negative photosensitive resin composition described above.

The inventive positive photosensitive resin composition may further contain (E) a compound capable of generating an acid or a radical by heat. The component (E), a compound capable of generating an acid or a radical by heat, can be blended in order to promote the thermal crosslinking reaction with the component (A') in the step of baking and post-curing a film at 100 to 300° C. after patterning.

In particular, the component (E) is preferably a compound that does not promote curing of a film and not prevent pattern formation until a pattern is formed by development. To this end, the component (E) preferably does not generate an acid or a radical at temperature in the step of removing and drying the solvent after applying the photosensitive resin composition, but generates an acid or a radical only by heat treatment after patterning, thereby promoting curing of the film or the pattern of the positive photosensitive resin composition. More specifically, the component (E) is preferably a compound that is decomposed by heat treatment at 100° C. to 300° C., preferably 150° C. to 300° C. and thereby generates an acid or a radical. By containing such component (E), crosslinking and curing reaction of the pattern or the film of the positive photosensitive resin composition can be further promoted in the step of baking and post-curing at 100 to 300° C. after patterning. Thus, the component (E) can further promote the crosslinking and curing reaction, thereby improving properties such as mechanical strength, chemical resistance, and adhesiveness of the obtained pattern or the film.

Preferable examples of the compound capable of generating an acid by heat include compounds described in paragraphs (0061) to (0085) of Japanese Patent Laid-Open Publication No. 2007-199653.

The formulation amount of the compound capable of generating an acid by heat is preferably 0.1 part by mass or more, more preferably 0.5 part by mass or more and preferably 30 parts by mass or less, more preferably 10 parts by mass or less, with respect to 100 parts by mass of the component (A') in the inventive positive photosensitive resin composition.

Preferable examples of the compound capable of generating a radical by heat include organic peroxides such as diisopropylbenzene hydroperoxide, 1,1,3,3-tetramethylbutyl hydroperoxide, cumene hydroperoxide, t-butyl hydroperoxide, and t-butyltrimethylsilyl peroxide; and radical initiators consisting of only carbon and hydrogen such as 2,3-dimethyl-2,3-diphenylbutane. Among them, radical initiators consisting of only carbon and hydrogen are preferable because they have high activation energy and are difficult to decompose by heat for drying.

The formulation amount of the compound capable of generating a radical by heat is preferably 0.5 to 4 parts by mass, more preferably 1 to 3 parts by mass, with respect to 100 parts by mass of the component (A') in the inventive positive photosensitive resin composition.

The inventive positive photosensitive resin composition may further contain other components besides the components (A'), (B"), (C"), (D), and (E). Examples of the other components include an adhesion assistant and (G) a surfactant. As (G) the surfactant, above-described compounds can be suitably used.

The negative photosensitive resin composition and the positive photosensitive resin composition of the present invention can be prepared by a usual method. The photosensitive resin compositions can be prepared by stirring and mixing the respective components and then filtering the mixture through a filter.

(Patterning Process)

Then, the patterning processes using the negative photosensitive resin composition and the positive photosensitive resin composition of the present invention will be described.

In either case of the negative photosensitive resin composition and the positive photosensitive resin composition of the present invention, a pattern can be formed by a well-known lithography technology. For example, the photosensitive resin composition may be applied by a spin coating method on a silicon wafer, a SiO$_2$ substrate, a SiN substrate, or a substrate having a formed pattern such as copper wiring, and pre-baked at about 80 to 130° C. for 50 to 600 seconds to form a photosensitive material film with a thickness of 1 to 50 μm, preferably 1 to 30 μm, more preferably 5 to 20 μm.

The spin coating method may be to dispense about 5 mL of the photosensitive resin composition on a silicon substrate and then rotate the substrate, thereby applying the photosensitive resin composition on the substrate. By adjusting the rotational speed during this operation, the thickness of the photosensitive material film on the substrate can be easily controlled.

Then, a mask for forming an intended pattern is put over the photosensitive material film, and the film is irradiated with a high energy beam having a wavelength of 190 to 500 nm such as i-line beam and g-line beam or an electron beam with an exposure dose of about 1 to 5,000 mJ/cm$^2$, preferably about 100 to 2,000 mJ/cm$^2$.

Then, if necessary, post exposure bake (PEB) may be carried out on a hot plate at 60 to 150° C. for 1 to 10 minutes, preferably at 80 to 120° C. for 1 to 5 minutes.

Then, development is performed. All of the negative photosensitive resin compositions according to the first, second, and third embodiments of the present invention are available for organic solvent development and alkali development with alkaline aqueous solution. On the other hand, the positive photosensitive resin composition according the present invention is available for alkali development with alkaline aqueous solution.

Examples of the organic solvent usable for organic solvent development include the above-described solvents used for preparing the photosensitive resin composition of the present invention. For example, ketones such as cyclohexanone and cyclopentanone, and glycols such as propylene glycol monomethyl ether are preferable. The development can be performed by a usual method such as spraying, puddling, or soaking in a developer. Then, if necessary, washing, rinsing, drying, and so forth may be performed to obtain a resist film having an intended pattern.

On the other hand, preferable alkaline aqueous solution usable for alkali development is a 2.38% tetramethylammonium hydroxide (TMAH) aqueous solution. The development can be performed by a usual method such as spraying, puddling, or soaking in a developer. Then, if necessary, washing, rinsing, drying, and so forth may be performed to obtain a resist film having an intended pattern.

Moreover, the film having a pattern obtained by the patterning process may be baked and post-cured with an oven or a hot plate at 100 to 300° C., preferably 150 to 300° C., more preferably 180 to 250° C. to form a cured film. In this post-curing step, the polyimide precursor structural unit in the inventive polyimide precursor polymer undergoes imidization ring-closure reaction, and the alkali-soluble hexafluoroisopropanol group is eliminated and removed from the system. When the post-curing temperature is 100 to 300° C., the crosslinking density of the film of the photosensitive resin composition can be increased, and remaining volatile components can be removed. Thus, this temperature range is preferable in view of adhesiveness to a substrate, heat resistance, strength, and electronic characteristics. The time for the post-curing can be 10 minutes to 10 hours.

The formed pattern can be used for a top coat coating a wiring, a circuit, and a substrate, etc. Such formed pattern and top coat have excellent insulating property and excellent adhesiveness to a metal layer of, for example, Cu of a wiring and a circuit to be coated, a metal electrode on a substrate, and an insulating substrate such as SiN substrate with a wiring and a circuit to be coated, and can significantly improve resolution capacity for forming a fine pattern with an appropriate mechanical strength as a top coat.

The cured film thus obtained has excellent adhesiveness to a substrate, heat resistance, electric characteristics, mechanical strength, and chemical resistance to an alkaline removing liquid. A semiconductor device using this cured film as a top coat has excellent reliability, and especially, generation of cracks during a thermal cycle test can be prevented. Therefore, this cured film is useful for a top coat to protect electric and electronic parts, semiconductor devices, etc.

The above top coat is useful for an insulator film for a semiconductor device including rewiring use, an insulator film for a multilayer printed substrate, a solder mask, and a cover lay film, because of its heat resistance, chemical resistance, and insulating property.

EXAMPLES

Hereinafter, the present invention will be specifically described with reference to synthesis examples, comparative synthesis examples, examples, and comparative examples, but the present invention is not limited to the following examples.

I. Synthesis of Polyimide Precursor Polymer Having Hexafluoroisopropanol Group

Chemical structural formulae of compounds used in the following synthesis examples are shown below.

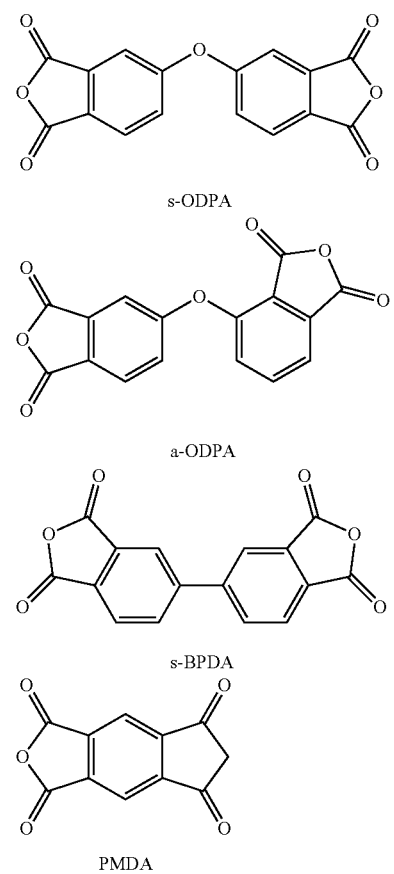

-continued

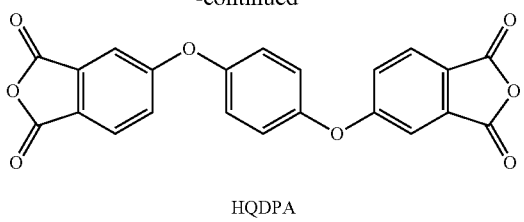

HQDPA

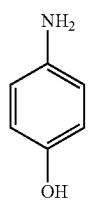
AP

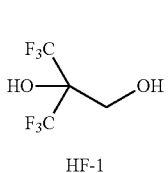
HF-1

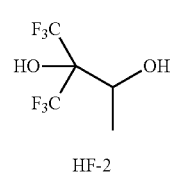
HF-2

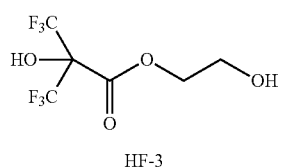
HF-3

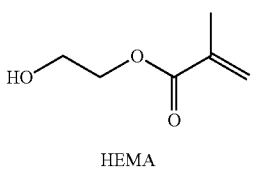
HEMA

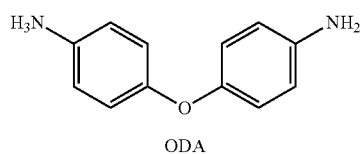
ODA

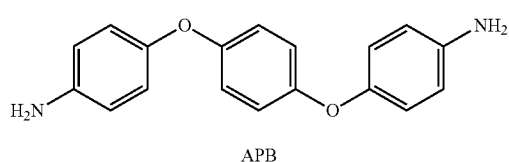
APB

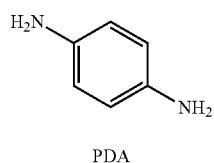
PDA

[Synthesis Example 1] Synthesis of Tetracarboxylic Acid Diester Compound

A 3 L flask equipped with a stirrer and a thermometer was charged with 100 g (322 mmol) of 3,3',4,4'-oxydiphthalic dianhydride (s-ODPA), 127.6 g (644 mmol) of a compound having a hexafluoroisopropanol, group (HF-1), and 400 g of γ-butyrolactone. To this solution was added 2.5 g (16 mmol) of 1,8-diazabicycloundecene under stirring at room temperature, and the solution was further stirred at room temperature for 24 hours. Then, 5.8 g of 10% hydrochloric acid aqueous solution was added dropwise under ice-cooling to terminate the reaction. To the reaction solution, 400 g of water and 600 g of 4-methyl-2-pentanone were added, and the organic layer was collected and washed with 400 g of water 6 times. The solvent of the obtained organic layer was distilled off to obtain 220 g of a tetracarboxylic acid diester compound having a hexafluoroisopropanol group with the following structure.

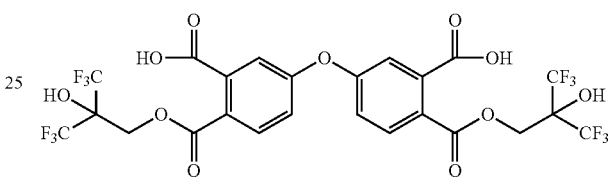

$^1$H-NMR analysis showed the following result and confirmed that the product was a tetracarboxylic acid diester compound having a hexafluoroisopropanol group with the above structure.

13.45 ppm (2H), 8.53 ppm (2H), 7.20-8.20 ppm (6H), 4.62 ppm (4H)

[Synthesis Example 2] Synthesis of Polyimide Precursor Polymer (A-1)

In a similar manner, a 3 L flask equipped with a stirrer and a thermometer was charged with 100 g (322 mmol) of 3,3',4,4'-oxydiphthalic dianhydride (s-ODPA), 127.6 g (644 mmol) of a compound having a hexafluoroisopropanol group (IF-1), and 400 g of γ-butyrolactone. To this solution was added 2.5 g (16 mmol) of 1,8-diazabicycloundecene under stirring at room temperature, and the solution was further stirred at room temperature for 24 hours. Then, 78.5 g (660 mmol) of thionyl chloride was added dropwise to the resulting solution under ice-cooling while maintaining the reaction solution temperature at 10° C. or less. After dropwise addition, the solution was stirred for 2 hours under ice-cooling. Then, a solution in which 58 g (290 mmol) of 4,4'-diaminodiphenyl ether (ODA), 1.8 g (16 mol) of 4-aminophenol (AP), and 104.4 g (1,320 mmol) of pyridine have been dissolved in 239 g of γ-butyrolactone was added dropwise thereto under ice-cooling while maintaining the reaction solution temperature at 10° C. or less. After dropwise addition, this reaction solution was added dropwise to 9 L of water under stirring at room temperature. The precipitate was then collected by filtration, washed with water as needed, and dried under reduced pressure at 40° C. for 48 hours to obtain the following polyimide precursor polymer (A-1). When the molecular weight of this polymer was measured by GPC, the weight average molecular weight was 15,000 in terms of polystyrene.

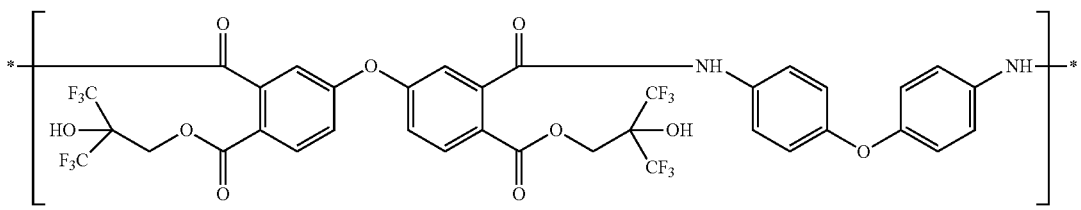

In the obtained polymer (A-1), the introduction amount of the hexafluoroisopropanol group was 0.23 mol with respect to 100 g of the polymer.

[Synthesis Example 3] Synthesis of Polyimide Precursor Polymer (A-2)

The following polyimide precursor polymer (A-2) was obtained in the same manner as in Synthesis Example 2 except that 3,3',4,4'-oxydiphthalic dianhydride (s-ODPA) was changed to 100 g (322 mol) of 2,3,3',4'-oxydiphthalic dianhydride (a-ODPA). When the molecular weight of this polymer was measured by GPC, the weight average molecular weight was 16,200 in terms of polystyrene.

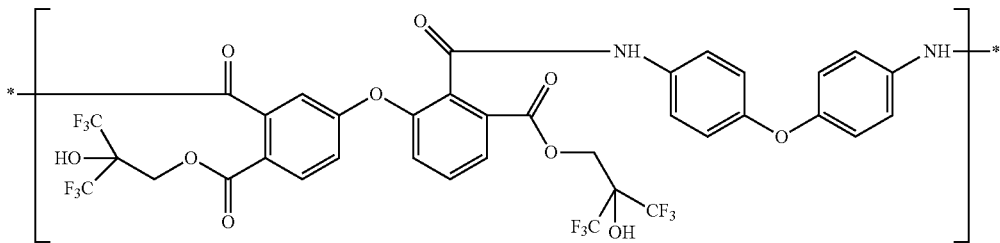

In the obtained polymer (A-2), the introduction amount of the hexafluoroisopropanol group was 0.23 mol with respect to 1.00 g of the polymer.

[Synthesis Example 4] Synthesis of Polyimide Precursor Polymer (A-3)

The following polyimide precursor polymer (A-3) was obtained in the same manner as in Synthesis Example 2 except that 3,3',4,4'-oxydiphthalic dianhydride (s-ODPA) was changed to 94.8 g (322 mmol) of 3,3',4,4'-biphenyltetracarboxylic dianhydride (s-BPDA). When the molecular weight of this polymer was measured by GPC, the weight average molecular weight was 14,300 in terms of polystyrene.

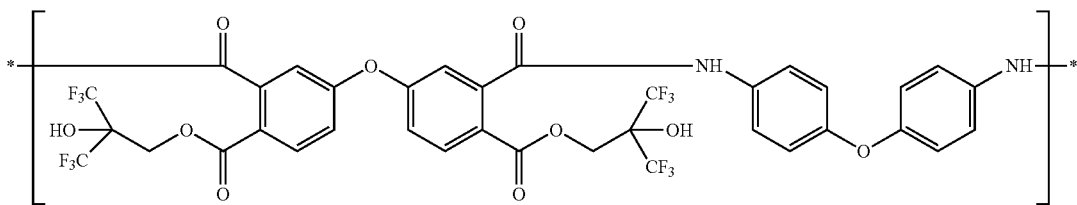

In the obtained polymer (A-3), the introduction amount of the hexafluoroisopropanol group was 0.23 mol with respect to 100 g of the polymer.

[Synthesis Example 5] Synthesis of Polyimide Precursor Polymer (A-4)

The following polyimide precursor polymer (A-4) was obtained in the same manner as in Synthesis Example 2 except that 3,3',4,4'-oxydiphthalic dianhydride (s-ODPA) was changed to 70.3 g (322 mmol) of pyromellitic dianhydride (PMDA). When the molecular weight of this polymer was measured by GPC, the weight average molecular weight was 12,800 in terms of polystyrene.

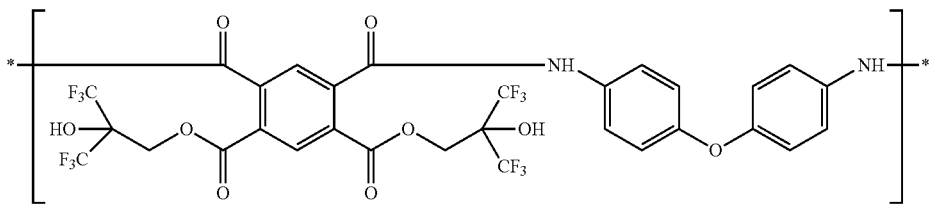

In the obtained polymer (A-4), the introduction amount of the hexafluoroisopropanol group was 0.26 mol with respect to 100 g of the polymer.

[Synthesis Example 6] Synthesis of Polyimide Precursor Polymer (A-5)

The following polyimide precursor polymer (A-5) was obtained in the same manner as in Synthesis Example 2 except that 3,3',4,4'-oxydiphthalic dianhydride (s-ODPA) was changed to 129.7 g (322 mmol) of 1,4-bis(3,4-dicarboxyphenoxy)benzene (HQDPA). When the molecular weight of this polymer was measured by GPC, the weight average molecular weight was 16,400 in terms of polystyrene.

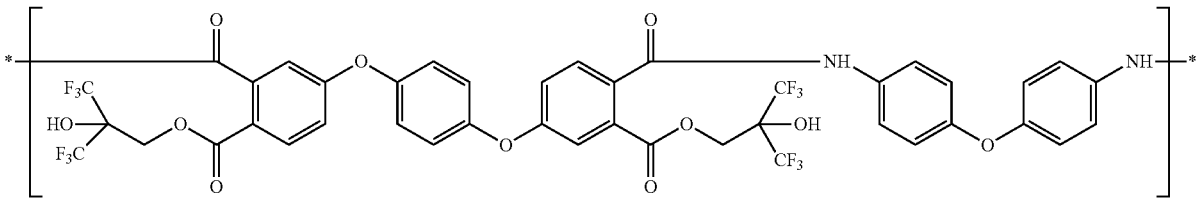

In the obtained polymer (A-5), the introduction amount of the hexafluoroisopropanol group was 0.21 mol with respect to 100 g of the polymer.

[Synthesis Example 7] Synthesis of Polyimide Precursor Polymer (A-6)

The following polyimide precursor polymer (A-6) was obtained in the same manner as in Synthesis Example 2 except that 58 g (290 mmol) of 4,4'-diaminodiphenyl ether (ODA) was changed to 84.7 g (290 mmol) of 1,4-bis(4-aminophenoxy)benzene (APB). When the molecular weight of this polymer was measured by GPC, the weight average molecular weight was 15,800 in terms of polystyrene.

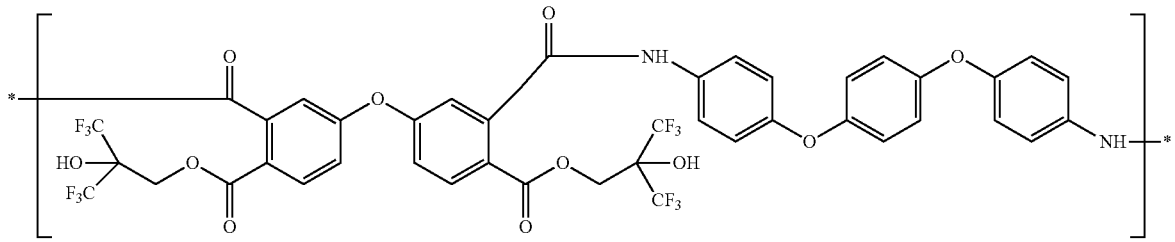

In the obtained polymer (A-6), the introduction amount of the hexafluoroisopropanol group was 0.21 mol with respect to 100 g of the polymer.

[Synthesis Example 8] Synthesis of Polyimide Precursor Polymer (A-7)

The following polyimide precursor polymer (A-7) was obtained in the same manner as in Synthesis Example 4 except that 58 g (290 mmol) of 4,4'-diaminodiphenyl ether (ODA) was changed to 84.7 g (290 mmol) of 1,4-bis(4-aminophenoxy)benzene (APB). When the molecular weight of this polymer was measured by GPC, the weight average molecular weight was 15,200 in terms of polystyrene.

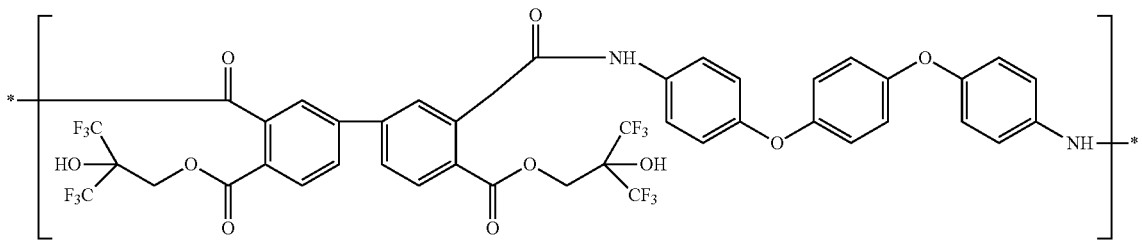

In the obtained polymer (A-7), the introduction amount of the hexafluoroisopropanol group was 0.21 mol with respect to 100 g of the polymer.

[Synthesis Example 9] Synthesis of Polyimide Precursor Polymer (A-8)

The following polyimide precursor polymer (A-8) was obtained in the same manner as in Synthesis Example 4 except that 58 g (290 mmol) of 4,4'-diaminodiphenyl ether (ODA) was changed to 31.4 g (290 mmol) of diaminobenzene (PDA). When the molecular weight of this polymer was measured by GPC, the weight average molecular weight was 10,200 in terms of polystyrene.

In the obtained polymer (A-8), the introduction amount of the hexafluoroisopropanol group was 0.26 mol with respect to 100 g of the polymer.

[Synthesis Example 10] Synthesis of Polyimide Precursor Polymer (A-9)

A 1 L flask equipped with a stirrer and a thermometer was charged with 50 g (161 mmol) of 3,3',4,4'-oxydiphthalic dianhydride (s-ODPA), 63.8 g (322 mmol) of a compound having a hexafluoroisopropanol group (HF-1), and 200 g of γ-butyrolactone. To this solution was added 1.25 g (8 mmol) of 1,8-diazabicycloundecene under stirring at room temperature, and the solution was further stirred at room temperature for 24 hours to obtain a solution of a tetracarboxylic acid diester compound having a hexafluoroisopropanol group.

Then, a 1 L flask equipped with a stirrer and a thermometer was likewise charged with 50 g (161 mmol) of 3,3',4,4'-oxydiphthalic dianhydride (s-ODPA), 41.9 g (322 mmol) of hydroxyethyl methacrylate (HEMA), and 200 g of γ-butyrolactone. To this solution was added 1.25 g (8 mmol) of 1,8-diazabicycloundecene under stirring at room temperature, and the solution was further stirred at room temperature for 24 hours to obtain a solution of a tetracarboxylic acid diester compound having a methacryloyloxy group.

These two tetracarboxylic acid diester compound solutions were then mixed in a 3 L flask equipped with a stirrer and a thermometer. Thereafter, as in Synthesis Example 2,

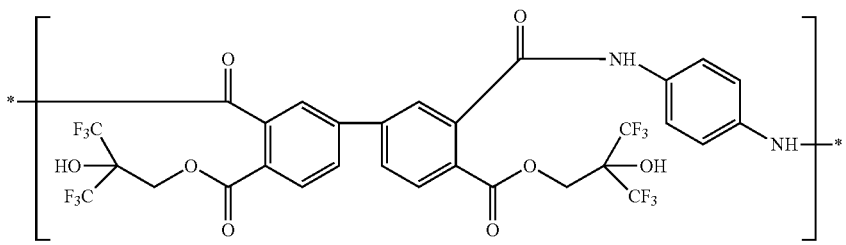

78.5 g (660 mmol) of thionyl chloride was added dropwise to the mixture under ice-cooling while maintaining the reaction solution temperature at 10° C. or less. After dropwise addition, the mixture was stirred for 2 hours under ice-cooling. Then, a solution in which 58 g (290 mmol) of 4,4'-diaminodiphenyl ether (ODA), 1.8 g (16 mmol) of 4-aminophenol (AP), and 104.4 g (1,320 mmol) of pyridine have been dissolved in 239 g of γ-butyrolactone was added dropwise thereto under ice-cooling while maintaining the reaction solution temperature at 10° C. or less. After dropwise addition, this reaction solution was added dropwise to 9 L of water under stirring at room temperature. The precipitate was then collected by filtration, washed with water as needed, and dried under reduced pressure at 40° C. for 48 hours to obtain the following polyimide precursor polymer (A-9). When the molecular weight of this polymer was measured by GPC, the weight average molecular weight was 16,200 in terms of polystyrene.

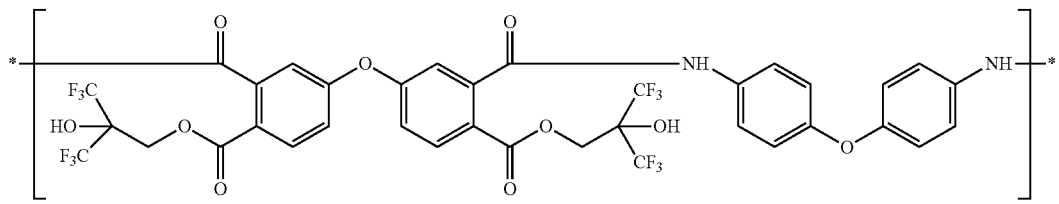

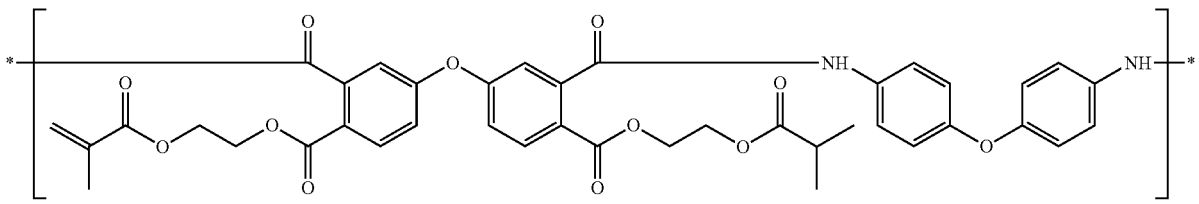

In the obtained polymer (A-9), the ratio of the polyimide precursor structural unit containing a hexafluoroisopropanol group to the polyimide precursor structural unit containing a methacryloyloxyethyl group was 50:50. In addition, the introduction amount of the hexafluoroisopropanol group was 0.12 mol with respect to 100 g of the polymer.

[Synthesis Example 11] Synthesis of Polyimide Precursor Polymer (A-10)

The following polyimide precursor polymer (A-10) was obtained in the same manner as in Synthesis Example 10 except that 3,3',4,4'-oxydiphthalic dianhydride (s-ODPA) used twice was both changed to 47.4 g (161 mmol) of 3,3',4,4'-biphenyltetracarboxylic dianhydride (s-BPDA). When the molecular weight of this polymer was measured by GPC, the weight average molecular weight was 14,100 in terms of polystyrene.

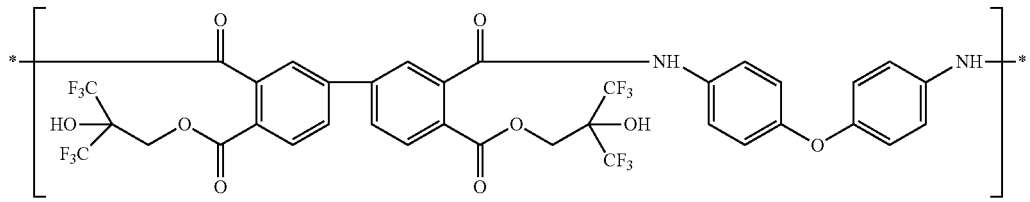

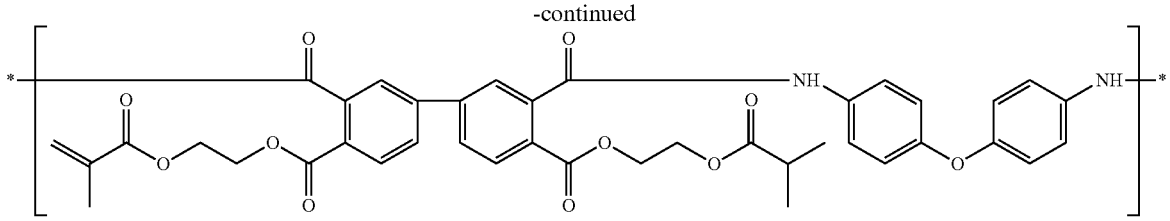

In the obtained polymer (A-10), the ratio of the polyimide precursor structural unit containing a hexafluoroisopropanol group to the polyimide precursor structural unit containing a methacryloyloxyethyl group was 50:50. In addition, the introduction amount of the hexafluoroisopropanol group was 0.13 mol with respect to 100 g of the polymer.

[Synthesis Example 12] Synthesis of Polyimide Precursor Polymer (A-11)

The following polyimide precursor polymer (A-11) was obtained in the same manner as in Synthesis Example 11 except that 58 g (290 mmol) of 4,4'-diaminodiphenyl ether (ODA) was changed to 84.7 g (290 mmol) of 1,4-bis(4-aminophenoxy)benzene (APB). When the molecular weight of this polymer was measured by GPC, the weight average molecular weight was 16,000 in terms of polystyrene.

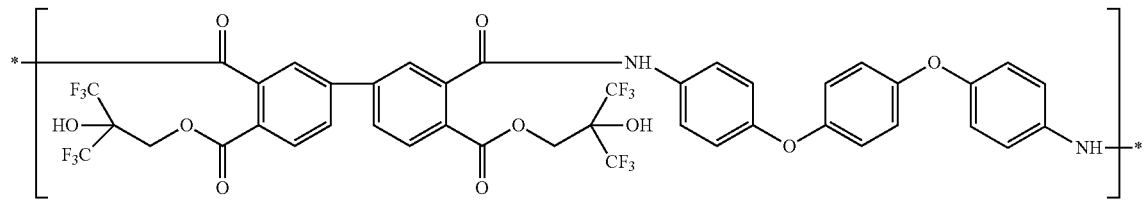

In the obtained polymer (A-11), the ratio of the polyimide precursor structural unit containing a hexafluoroisopropanol group to the polyimide precursor structural unit containing a methacryloyloxyethyl group was 50:50. In addition, the introduction amount of the hexafluoroisopropanol group in the obtained polymer (A-11) was 0.11 mol with respect to 100 g of the polymer.

[Synthesis Example 13] Synthesis of Polyimide Precursor Polymer (A-12)

The following polyimide precursor polymer (A-12) was obtained in the same manner as in Synthesis Example 11 except that 58 g (290 mmol) of 4,4'-diaminodiphenyl ether (ODA) was changed to 31.4 g (290 mmol) of diaminobenzene (PDA). When the molecular weight of this polymer was measured by GPC, the weight average molecular weight was 9,800 in terms of polystyrene.

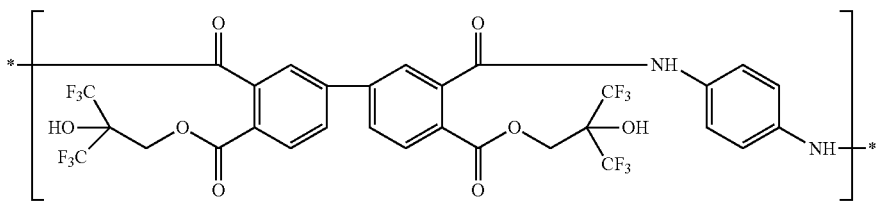

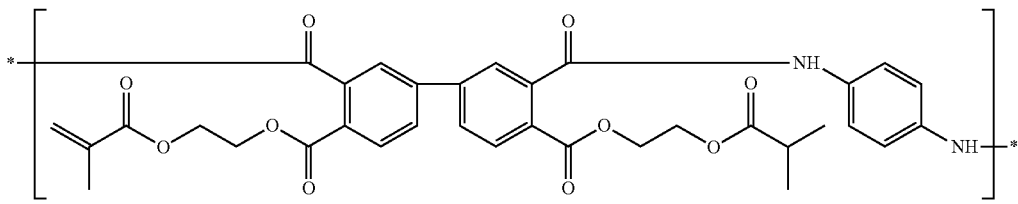

In the obtained polymer (A-12), the ratio of the polyimide precursor structural unit containing a hexafluoroisopropanol group to the polyimide precursor structural unit containing a methacryloyloxyethyl group was 50:50. In addition, the introduction amount of the hexafluoroisopropanol group was 0.14 mol with respect to 100 g of the polymer.

[Synthesis Example 14] Synthesis of Polyimide Precursor Polymer (A-13)

The following polyimide precursor polymer (A-13) was obtained in the same manner as in Synthesis Example 11 except that reaction of 66.4 g (226 mmol) of 3,3',4,4'-biphenyltetracarboxylic dianhydride (s-BPDA) with 89.3 g (451 mmol) of the compound having a hexafluoroisopropanol group (HF-1), and reaction of 28.5 g (97 mmol) of 3,3',4,4'-biphenyltetracarboxylic dianhydride (s-BPDA) with 25.2 g (193 mmol) of hydroxyethyl methacrylate (HEMA) were performed. When the molecular weight of this polymer was measured by GPC, the weight average molecular weight was 16,100 in terms of polystyrene.

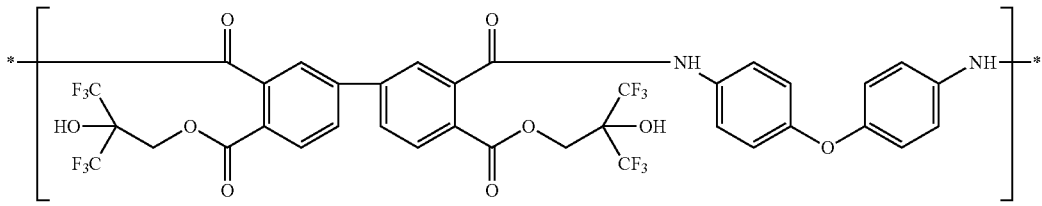

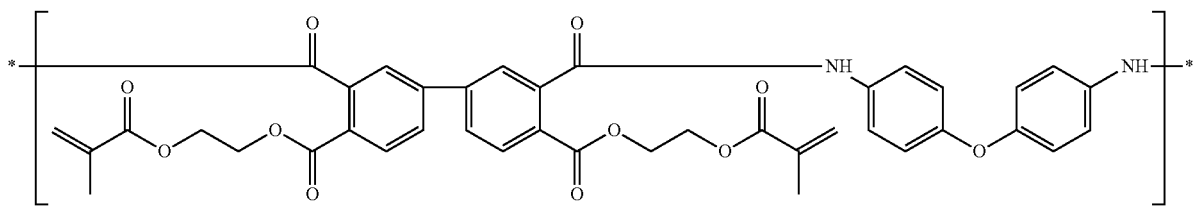

In the obtained polymer (A-13), the ratio of the polyimide precursor structural unit containing a hexafluoroisopropanol group to the polyimide precursor structural unit containing a methacryloyloxyethyl group was 70:30. In addition, the introduction amount of the hexafluoroisopropanol group was 0.17 mol with respect to 100 g of the polymer.

[Synthesis Example 15] Synthesis of Polyimide Precursor Polymer (A-14)

The following polyimide precursor polymer (A-14) was obtained in the same manner as in Synthesis Example 11 except that reaction of 28.5 g (97 mmol) of 3,3',4,4'-biphenyltetracarboxylic dianhydride (s-BPDA) with 38.3 g (193 mmol) of the compound having a hexafluoroisopropanol group (HF-1), and reaction of 66.4 g (226 mmol) of 3,3',4,4'-biphenyltetracarboxylic dianhydride (s-BPDA) with 58.7 g (451 mmol) of hydroxyethyl methacrylate (HEMA) were performed. When the molecular weight of this polymer was measured by GPC, the weight average molecular weight was 16,500 in terms of polystyrene.

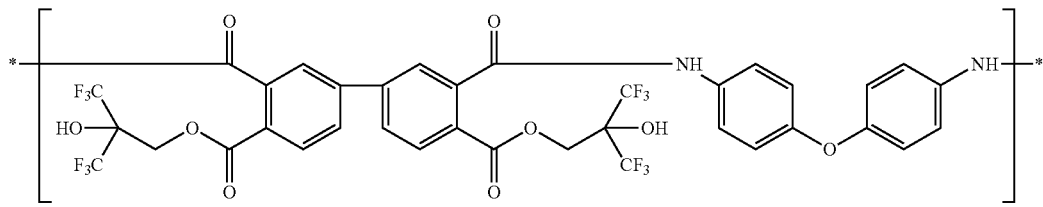

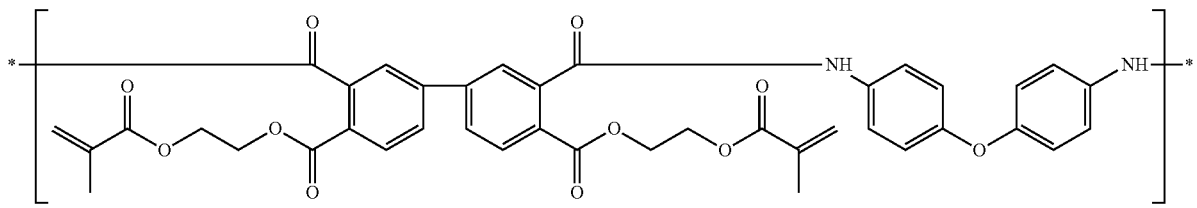

In the obtained polymer (A-14), the ratio of the polyimide precursor structural unit containing a hexafluoroisopropanol group to the polyimide precursor structural unit containing a methacryloyloxyethyl group was 30:70. In addition, the introduction amount of the hexafluoroisopropanol group was 0.08 mol with respect to 100 g of the polymer.

[Synthesis Example 16] Synthesis of Polyimide Precursor Polymer (A-15)

The following polyimide precursor polymer (A-15) was obtained in the same manner as in Synthesis Example 4 except that the compound having a hexafluoroisopropanol group (HF-1) was changed to 136.6 g (644 mmol) of a compound having a hexafluoroisopropanol group (HF-2). When the molecular weight of this polymer was measured by GPC, the weight average molecular weight was 15,800 in terms of polystyrene.

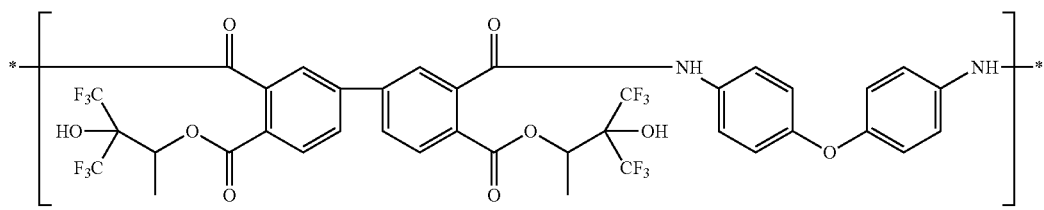

In the obtained polymer (A-15), the introduction amount of the hexafluoroisopropanol group was 0.23 mol with respect to 100 g of the polymer.

[Synthesis Example 17] Synthesis of Polyimide Precursor Polymer (A-16)

The following polyimide precursor polymer (A-16) was obtained in the same manner as in Synthesis Example 4 except that the compound having a hexafluoroisopropanol group (HF-1) was changed to 165.0 g (644 mmol) of a compound having a hexafluoroisopropanol group (HF-3). When the molecular weight of this polymer was measured by GPC, the weight average molecular weight was 15,900 in terms of polystyrene.

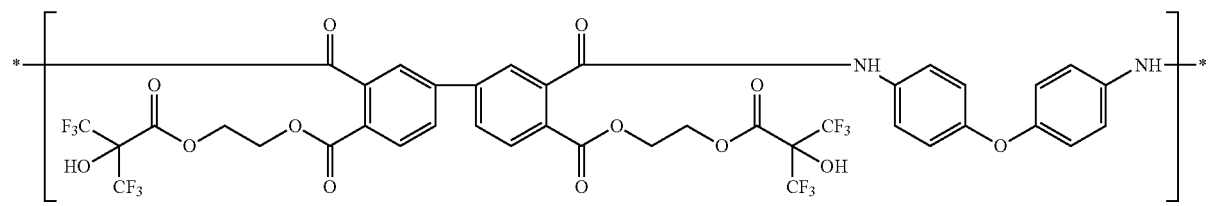

In the obtained polymer (A-16), the introduction amount of the hexafluoroisopropanol group was 0.21 mol with respect to 100 g of the polymer.

[Synthesis Example 18] Synthesis of Polyimide Precursor Polymer (A-17)

The following polyimide precursor polymer (A-17) was obtained in the same manner as in Synthesis Example 11 except that the compound having a hexafluoroisopropanol group (HF-1) was changed to 58.0 g (322 mmol) of a compound having a hexafluoroisopropanol group (HF-2). When the molecular weight of this polymer was measured by GPC, the weight average molecular weight was 16,300 in terms of polystyrene.

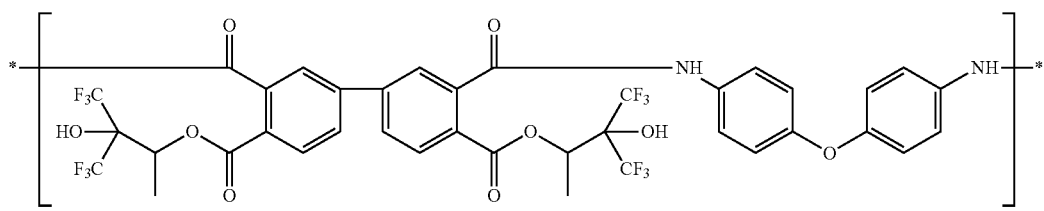

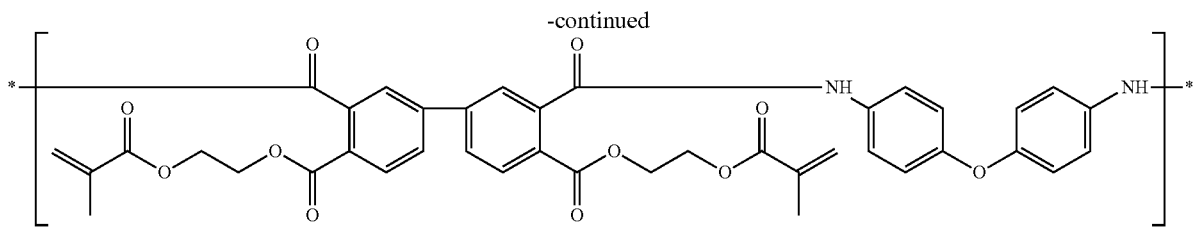

In the obtained polymer (A-17), the ratio of the polyimide precursor structural unit containing a hexafluoroisopropanol group to the polyimide precursor structural unit containing a methacryloyloxyethyl group was 50:50. In addition, the introduction amount of the hexafluoroisopropanol group was 0.12 mol with respect to 100 g of the polymer.

[Synthesis Example 19] Synthesis of Polyimide Precursor Polymer (A-18)

The following polyimide precursor polymer (A-18) was obtained in the same manner as in Synthesis Example 11 except that the compound having a hexafluoroisopropanol group (HF-1) was changed to 68.3 g (322 mmol) of a compound having a hexafluoroisopropanol group (HF-3). When the molecular weight of this polymer was measured by GPC, the weight average molecular weight was 16,700 in terms of polystyrene.

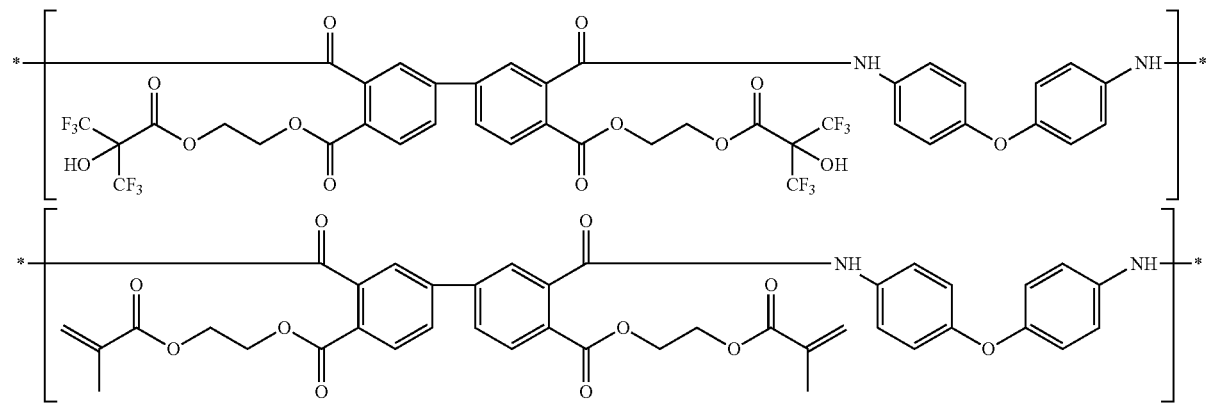

In the obtained polymer (A-18), the ratio of the polyimide precursor structural unit containing a hexafluoroisopropanol group to the polyimide precursor structural unit containing a methacryloyloxyethyl group was 50:50. In addition, the introduction amount of the hexafluoroisopropanol group was 0.12 mol with respect to 100 g of the polymer.

[Comparative Synthesis Example 1] Synthesis of Polyimide Precursor Polymer (A-19)

The following polyimide precursor polymer (A-19) containing no hexafluoroisopropanol group was obtained in the same manner as in Synthesis Example 2 except that the compound having a hexafluoroisopropanol group (HF-1) was changed to 83.8 g (644 mmol) of hydroxyethyl methacrylate (HEMA). When the molecular weight of this polymer was measured by GPC, the weight average molecular weight was 15,400 in terms of polystyrene.

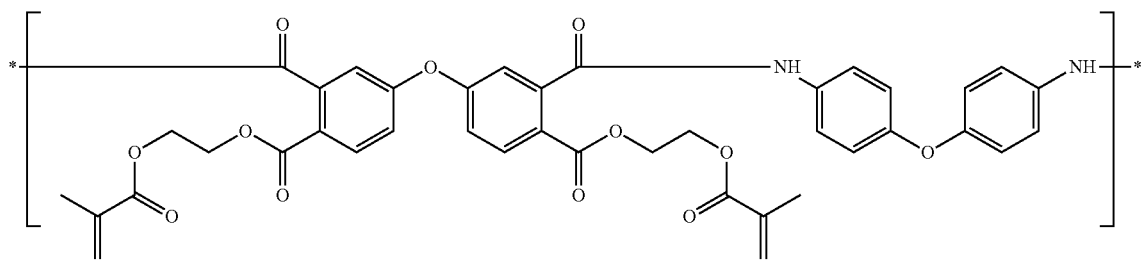

[Comparative Synthesis Example 2] Synthesis of Polyimide Precursor Polymer (A-20)

The following polyimide precursor polymer (A-20) containing no hexafluoroisopropanol group was obtained in the same manner as in Synthesis Example 3 except that the compound having a hexafluoroisopropanol group (HF-1) was changed to 83.8 g (644 mmol) of hydroxyethyl methacrylate (HEMA). When the molecular weight of this polymer was measured by GPC, the weight average molecular weight was 14,900 in terms of polystyrene.

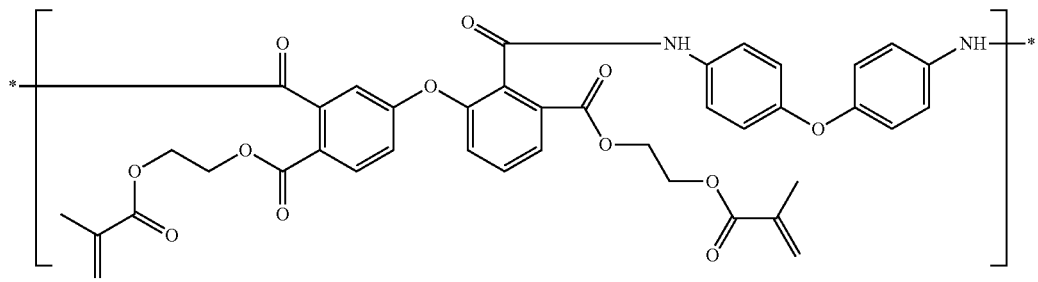

[Comparative Synthesis Example 3] Synthesis of Polyimide Precursor Polymer (A-21)

The following polyimide precursor polymer (A-21) containing no hexafluoroisopropanol group was obtained in the same manner as in Synthesis Example 4 except that the compound having a hexafluoroisopropanol group (HF-1) was changed to 83.8 g (644 mmol) of hydroxyethyl methacrylate (HEMA). When the molecular weight of this polymer was measured by GPC, the weight average molecular weight was 13,800 in terms of polystyrene.

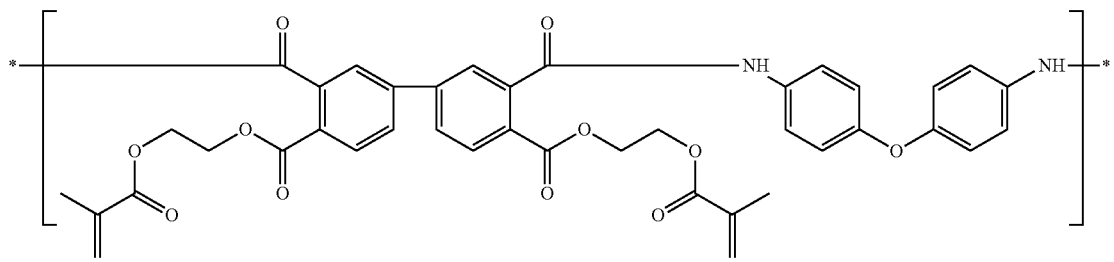

[Comparative Synthesis Example 4] Synthesis of Polyimide Precursor Polymer (A-22)

The following polyimide precursor polymer (A-22) containing no hexafluoroisopropanol group was obtained in the same manner as in Synthesis Example 8 except that the compound having a hexafluoroisopropanol group (HF-1) was changed to 83.8 g (644 mmol) of hydroxyethyl methacrylate (HEMA). When the molecular weight of this polymer was measured by GPC, the weight average molecular weight was 14,700 in terms of polystyrene.

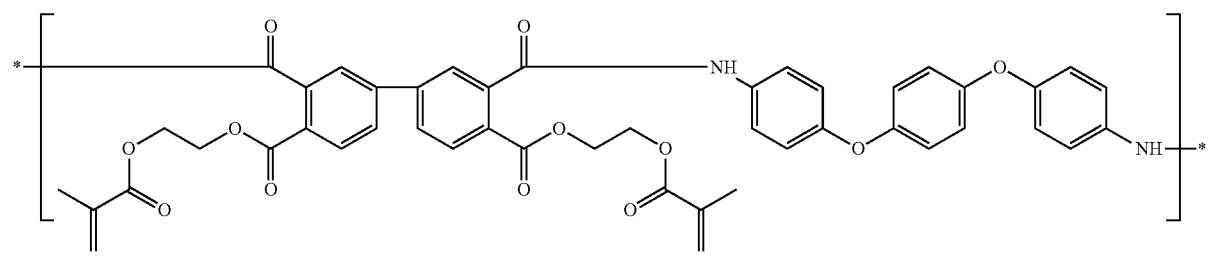

II. Preparation of Photosensitive Resin Composition

The polymers synthesized in Synthesis Examples 2 to 19 and Comparative Synthesis Examples 1 to 4 were used to prepare resin compositions each containing 40 mass % of the resin, with the composition and the formulation amount shown in Tables 1 to 12. The resin compositions were each stirred, mixed, dissolved, and filtered through a 0.5-μm filter made of Teflon (registered trade mark) for microfiltration to obtain photosensitive resin compositions.

TABLE 1

|  | Photosensitive resin composition 1 | Photosensitive resin composition 2 | Photosensitive resin composition 3 | Photosensitive resin composition 4 |
|---|---|---|---|---|
| Polyimide precursor polymer | A-9 100 parts by mass | A-10 100 parts by mass | A-11 100 parts by mass | A-14 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Cross-linking agent | — | — | — | — |
| Solvent | Cyclopentanone 150 parts by mass | Cyclopentanone 150 parts by mass | Cyclopentanone 150 parts by mass | Cyclopentanone 150 parts by mass |

Photosensitive resin compositions 1 to 4 shown in Table 1 relate to the negative photosensitive resin composition according to the first embodiment of the present invention.

TABLE 2

|  | Photosensitive resin composition 5 | Photosensitive resin composition 6 | Photosensitive resin composition 7 | Photosensitive resin composition 8 | Photosensitive resin composition 9 | Photosensitive resin composition 10 |
|---|---|---|---|---|---|---|
| Polyimide precursor polymer | A-10 100 parts by mass | A-12 100 parts by mass | A-13 100 parts by mass | A-14 100 parts by mass | A-17 100 parts by mass | A-18 100 parts by mass |
| Photo-radical | Photo-radical | Photo-radical | Photo-radical | Photo-radical | Photo-radical | Photo-radical |

TABLE 2-continued

|  | Photosensitive resin composition 5 | Photosensitive resin composition 6 | Photosensitive resin composition 7 | Photosensitive resin composition 8 | Photosensitive resin composition 9 | Photosensitive resin compostion 10 |
|---|---|---|---|---|---|---|
| initiator | initiator 1 2 parts by mass | initiator 1 2 parts by mass | initiator 1 2 parts by mass | initiator 1 2 parts by mass | initiator 1 2 parts by mass | initiator 1 2 parts by mass |
| Crosslinking agent | CL-1 15 parts by mass | CL-1 15 parts by mass | CL-1 15 parts by mass | CL-1 15 parts by mass | CL-1 15 parts by mass | CL-1 15 parts by mass |
| Solvent | Cyclopentanone 150 parts by mass | Cyclopentanone 150 parts by mass | Cyclopentanone 150 parts by mass | Cyclopentanone 150 parts by mass | Cyclopentanone 150 parts by mass | Cyclopentanone 150 parts by mass |

Photosensitive resin compositions 5 to 0.10 shown in Table 2 relate to the negative photosensitive resin composition according to the second embodiment of the present invention.

TABLE 3

|  | Comparative photosensitive resin composition 1 | Comparative photosensitive resin composition 2 | Comparative photosensitive resin composition 3 | Comparative photosensitive resin composition 4 |
|---|---|---|---|---|
| Polyimide precursor polymer | A-19 100 parts by mass | A-20 100 parts by mass | A-21 100 parts by mass | A-22 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Cross-linking agent | CL-1 15 parts by mass | CL-1 15 parts by mass | CL-1 15 parts by mass | CL-1 15 parts by mass |
| Solvent | Cyclopentanone 150 parts by mass | Cyclopentanone 150 parts by mass | Cyclopentanone 150 parts by mass | Cyclopentanone 150 parts by mass |
| Base resin solubility | insoluble | insoluble | insoluble | insoluble |

Comparative photosensitive resin compositions 1 to 4 shown in Table 3 use the polyimide precursor polymers synthesized in Comparative Synthesis Examples 1 to 4 as the base resin, in place of the inventive polyimide precursor polymer in the negative photosensitive resin compositions according to the second embodiment of the present invention. Since the polyimide precursor polymers synthesized in Comparative Synthesis Examples 1 to 4 are not inventive polyimide precursor polymer containing a hexafluoroisopropanol group, these polymers could not completely dissolve in the solvent of cyclopentanone.

TABLE 4

|  | Comparative photosensitive resin composition 5 | Comparative photosensitive resin composition 6 | Comparative photosensitive resin composition 7 | Comparative photosensitive resin composition 8 |
|---|---|---|---|---|
| Polyimide precursor polymer | A-19 100 parts by mass | A-20 100 parts by mass | A-21 100 parts by mass | A-22 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Cross-linking agent | CL-1 15 parts by mass | CL-1 15 parts by mass | CL-1 15 parts by mass | CL-1 15 parts by mass |
| Solvent | NMP 150 parts by mass | NMP 150 parts by mass | NMP 150 parts by mass | NMP 150 parts by mass |

Since the polyimide precursor polymers synthesized in Comparative Synthesis Examples 1 to 4 could not dissolve in cyclopentanone, a solvent of N-methyl-2-pyrrolidone (NMP) was used as shown in Table 4 to prepare Comparative photosensitive resin compositions 5 to 8.

TABLE 5

|  | Photosensitive resin composition 11 | Photosensitive resin composition 12 | Photosensitive resin composition 13 | Photosensitive resin composition 14 | Photosensitive resin composition 15 | Photosensitive resin composition 16 |
|---|---|---|---|---|---|---|
| Polyimide precursor polymer | A-1 100 parts by mass | A-5 100 parts by mass | A-6 100 parts by mass | A-7 100 parts by mass | A-10 100 parts by mass | A-12 100 parts by mass |
| Photo acid generator | Photo acid generator 1 2 parts by mass | Photo acid generator 1 2 parts by mass | Photo acid generator 1 2 parts by mass | Photo acid generator 1 2 parts by mass | Photo acid generator 1 2 parts by mass | Photo acid generator 1 2 parts by mass |
| Crosslinking agent | CL-2 15 parts by mass | CL-2 15 parts by mass | CL-2 15 parts by mass | CL-2 15 parts by mass | CL-2 15 parts by mass | CL-2 15 parts by mass |

TABLE 5-continued

|  | Photosensitive resin composition 11 | Photosensitive resin composition 12 | Photosensitive resin composition 13 | Photosensitive resin composition 14 | Photosensitive resin composition 15 | Photosensitive resin composition 16 |
|---|---|---|---|---|---|---|
| Crosslinking agent | CL-3 15 parts by mass | CL-3 15 parts by mass | CL-3 15 parts by mass | CL-3 15 parts by mass | CL-3 15 parts by mass | CL-3 15 parts by mass |
| Solvent | Cyclopentanone 150 parts by mass | Cyclopentanone 150 parts by mass | Cyclopentanone 150 parts by mass | Cyclopentanone 150 parts by mass | Cyclopentanone 150 parts by mass | Cyclopentanone 150 parts by mass |

TABLE 6

|  | Photosensitive resin compositon 17 | Photosensitive resin compositon 18 |
|---|---|---|
| Polyimide precursor polymer | A-13 100 parts by mass | A-14 100 parts by mass |
| Photo acid generator | Photo acid generator 1 2 parts by mass | Photo acid generator 1 2 parts by mass |
| Crosslinking agent | CL-2 15 parts by mass | CL-2 15 parts by mass |
| Crosslinking agent | CL-3 15 parts by mass | CL-3 15 parts by mass |
| Solvent | Cyclopentanone 150 parts by mass | Cyclopentanone 150 parts by mass |

Photosensitive resin compositions 11 to 18 shown in Tables 5 and 6 relate to the negative photosensitive resin composition according to the third embodiment of the present invention.

TABLE 7

|  | Photosensitive resin composition 19 | Photosensitive resin composition 20 | Photosensitive resin composition 21 | Photosensitive resin composition 22 | Photosensitive resin composition 23 | Photosensitive resin composition 24 |
|---|---|---|---|---|---|---|
| Polyimide precursor polymer | A-1 100 parts by mass | A-2 100 parts by mass | A-3 100 parts by mass | A-4 100 parts by mass | A-5 100 parts by mass | A-6 100 parts by mass |
| Photosensitive agent | Photosensitive agent 1 15 parts by mass | Photosensitive agent 1 15 parts by mass | Photosensitive agent 1 15 parts by mass | Photosensitive agent 1 15 parts by mass | Photosensitive agent 1 15 parts by mass | Photosensitive agent 1 15 parts by mass |
| Crosslinking agent | CL-2 5 parts by mass | CL-2 5 parts by mass | CL-2 5 parts by mass | CL-2 5 parts by mass | CL-2 5 parts by mass | CL-2 5 parts by mass |
| Crosslinking agent | CL-3 15 parts by mass | CL-3 15 parts by mass | CL-3 15 parts by mass | CL-3 15 parts by mass | CL-3 15 parts by mass | CL-3 15 parts by mass |
| Solvent | Cyclopentanone 150 parts by mass | Cyclopentanone 150 parts by mass | Cyclopentanone 150 parts by mass | Cyclopentanone 150 parts by mass | Cyclopentanone 150 parts by mass | Cyclopentanone 150 parts by mass |

TABLE 8

|  | Photosensitive resin composition 25 | Photosensitive resin composition 26 | Photosensitive resin composition 27 | Photosensitive resin composition 28 | Photosensitive resin composition 29 | Photosensitive resin composition 30 | Photosensitive resin composition 31 |
|---|---|---|---|---|---|---|---|
| Polyimide precursor polymer | A-7 100 parts by mass | A-8 100 parts by mass | A-12 100 parts by mass | A-13 100 parts by mass | A-15 100 parts by mass | A-16 100 parts by mass | A-18 100 parts by mass |
| Photosensitive agent | Photosensitive agent 1 | Photosensitive agent 1 | Photosensitive agent 1 | Photosensitive agent 1 | Photosensitive agent 1 | Photosensitive agent 1 | Photosensitive agent 1 |

TABLE 8-continued

|  | Photosensitive resin composition 25 | Photosensitive resin composition 26 | Photosensitive resin composition 27 | Photosensitive resin composition 28 | Photosensitive resin composition 29 | Photosensitive resin composition 30 | Photosensitive resin composition 31 |
| --- | --- | --- | --- | --- | --- | --- | --- |
| Crosslinking agent | 15 parts by mass CL-2 5 parts by mass | 15 parts by mass CL-2 5 parts by mass | 15 parts by mass CL-2 5 parts by mass | 15 parts by mass CL-2 5 parts by mass | 15 parts by mass CL-2 5 parts by mass | 15 parts by mass CL-2 5 parts by mass | 15 parts by mass CL-2 5 parts by mass |
| Crosslinking agent | CL-3 15 parts by mass | CL-3 15 parts by mass | CL-3 15 parts by mass | CL-3 15 parts by mass | CL-3 15 parts by mass | CL-3 15 parts by mass | CL-3 15 parts by mass |
| Solvent | Cyclopentanone 150 parts by mass | Cyclopentanone 150 parts by mass | Cyclopentanone 150 parts by mass | Cyclopentanone 150 parts by mass | Cyclopentanone 150 parts by mass | Cyclopentanone 150 parts by mass | Cyclopentanone 150 parts by mass |

Photosensitive resin compositions 19 to 31 shown in Tables 7 and 8 relate to the positive photosensitive resin composition according to the present invention.

TABLE 9

|  | Comparative photosensitive resin composition 9 | Comparative photosensitive resin composition 10 | Comparative photosensitive resin composition 11 | Comparative photosensitive resin composition 12 |
| --- | --- | --- | --- | --- |
| Polyimide precursor polymer | A-19 100 parts by mass | A-20 100 parts by mass | A-21 100 parts by mass | A-22 100 parts by mass |
| Photosensitive agent | Photosensitive agent 1 15 parts by mass | Photosensitive agent 1 15 parts by mass | Photosensitive agent 1 15 parts by mass | Photosensitive agent 1 15 parts by mass |
| Crosslinking agent | CL-2 5 parts by mass | CL-2 5 parts by mass | CL-2 5 parts by mass | CL-2 5 parts by mass |
| Crosslinking agent | CL-3 15 parts by mass | CL-3 15 parts by mass | CL-3 15 parts by mass | CL-3 15 parts by mass |
| Solvent | Cyclopentanone 150 parts by mass | Cyclopentanone 150 parts by mass | Cyclopentanone 150 parts by mass | Cyclopentanone 150 parts by mass |
| Base resin solubility | insoluble | insoluble | insoluble | insoluble |

Comparative photosensitive resin compositions 9 to 12 shown in Table 9 use the polyimide precursor polymers synthesized in Comparative Synthesis Examples 1 to 4 as the base resin, in place of the inventive polyimide precursor polymer in the positive photosensitive resin compositions according to the present invention. Since the polyimide precursor polymers synthesized in Comparative Synthesis Examples are not inventive polyimide precursor polymer containing a hexafluoroisopropanol group, these polymers could not completely dissolve in the solvent of cyclopentanone.

TABLE 10

|  | Comparative photosensitive resin composition 13 | Comparative photosensitive resin composition 14 | Comparative photosensitive resin composition 15 | Comparative photosensitive resin composition 16 |
| --- | --- | --- | --- | --- |
| Polyimide precursor polymer | A-19 100 parts by mass | A-20 100 parts by mass | A-21 100 parts by mass | A-22 100 parts by mass |
| Photosensitive resin | Photosensitive agent 1 15 parts by mass | Photosensitive agent 1 15 parts by mass | Photosensitive agent 1 15 parts by mass | Photosensitive agent 1 15 parts by mass |
| Crosslinking agent | CL-2 5 parts by mass | CL-2 5 parts by mass | CL-2 5 parts by mass | CL-2 5 parts by mass |
| Crosslinking agent | CL-3 15 parts by mass | CL-3 15 parts by mass | CL-3 15 parts by mass | CL-3 15 parts by mass |
| Solvent | NMP 150 parts by mass | NMP 150 parts by mass | NMP 150 parts by mass | NMP 150 parts by mass |

Since the polyimide precursor polymers synthesized in Comparative Synthesis Examples 1 to 4 could not dissolve in cyclopentanone, a solvent of N-methyl-2-pyrrolidone (NMP) was used as shown in Table 10 to prepare Comparative photosensitive resin compositions 13 to 16.

TABLE 11

|  | Photosensitive resin composition 32 | Photosensitive resin composition 33 | Photosensitive resin composition 34 | Photosensitive resin composition 35 |
| --- | --- | --- | --- | --- |
| Polyimide precursor polymer | A-1 100 parts by mass | A-5 100 parts by mass | A-6 100 parts by mass | A-7 100 parts by mass |
| Photosensitive agent | Photosensitive agent 1 15 parts by mass | Photosensitive agent 1 15 parts by mass | Photosensitive agent 1 15 parts by mass | Photosensitive agent 1 15 parts by mass |
| Crosslinking agent | CL-2 5 parts by mass | CL-2 5 parts by mass | CL-2 5 parts by mass | CL-2 5 parts by mass |
| Crosslinking agent | CL-3 15 parts by mass | CL-3 15 parts by mass | CL-3 15 parts by mass | CL-3 15 parts by mass |
| Thermal acid generator | E-1 2 parts by mass | E-1 2 parts by mass | E-1 2 parts by mass | E-1 2 parts by mass |
| Solvent | Cyclopentanone 150 parts by mass | Cyclopentanone 150 parts by mass | Cyclopentanone 150 parts by mass | Cyclopentanone 150 parts by mass |

Photosensitive resin compositions 32 to 35 shown in Table 11 relate to the embodiment of the positive photosensitive resin composition especially containing the component (E) of the present invention.

TABLE 12

|  | Photosensitive resin composition 36 | Photosensitive resin composition 37 |
|---|---|---|
| Polyimide presursor polymer | A-12<br>100 parts by mass | A-13<br>100 parts by mass |
| Photosensitive agent | Photosensitive agent 1<br>15 parts by mass | Photosensitive agent 1<br>15 parts by mass |
| Crosslinking agent | CL-2<br>5 parts by mass | CL-2<br>5 parts by mass |
| Crosslinking agent | CL-3<br>15 parts by mass | CL-3<br>15 parts by mass |
| Thermal radical generator | E-2<br>2 parts by mass | E-2<br>2 parts by mass |
| Solvent | Cyclopentanone<br>150 parts by mass | Cyclopentanone<br>150 parts by mass |

Photosensitive resin compositions 36 and 37 shown in Table 12 also relate to the embodiment of the positive photosensitive resin composition especially containing the component (E) of the present invention.

Moreover, in Tables 1 to 12, the photo-radical initiator (Photo-radical initiator 1), the photo acid generator (Photo acid generator 1), the photosensitive agent of a quinone diazide compound (Photosensitive agent 1), the crosslinking agents (CL-1) to (CL-3), the thermal acid generator (E-1), and the thermal radical generator (E-2) are shown below.

Photo-radical initiator (Photo-radical initiator 1): NP-1919 manufactured by ADEKA Corp.

Photo acid generator (Photo acid generator 1)

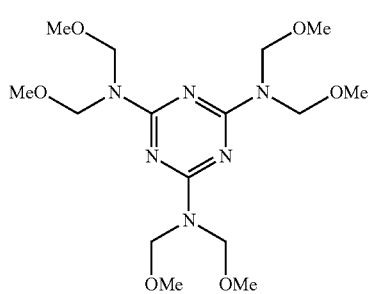

Photosensitive agent (Photosensitive agent 1)

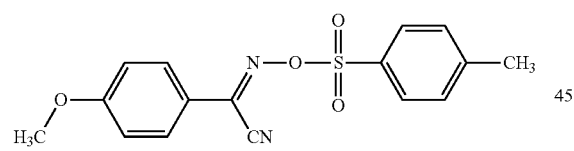

wherein Q represents a 1,2-naphthoquinone diazide sulfonyl group shown by the following formula (30) or a hydrogen atom, provided that 90% of Q is substituted with a 1,2-naphthoquinone diazide sulfonyl group shown by the formula (30).

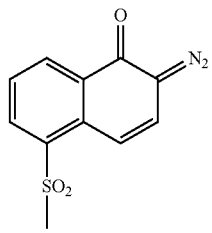

(30)

Crosslinking agent (CL-1): ethylene glycol diacrylate

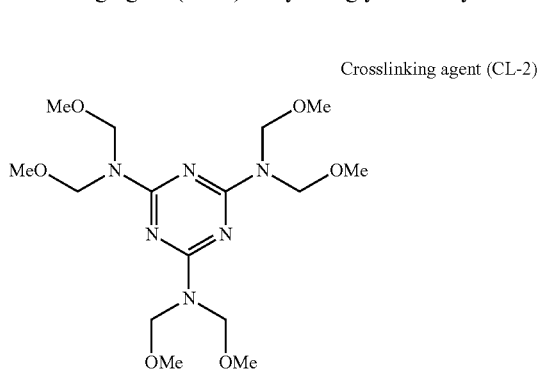

Crosslinking agent (CL-2)

Crosslinking agent (CL-3)

wherein 2≤t≤3.

Thermal acid generator (E-1)

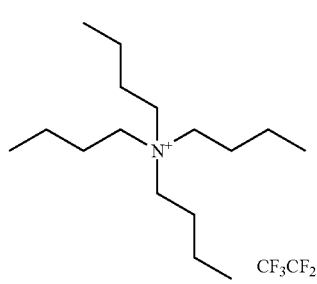

$CF_3CF_2CF_2CF_2SO_3^-$

Thermal radical generator (E-2): 2,3-dimethyl-2,3-diphenylbutane

III. Patterning Process 5 mL of Photosensitive resin compositions 1 to 37 and Comparative photosensitive resin compositions 5 to 8, 13 to 16 were each dispensed and applied onto a silicon substrate by rotating the substrate, i.e., by the spin coating method so as to give a film thickness of 10 μm after patterning and baking for post-curing. That is, the rotational speed during applying was adjusted such that a post-cured film had a thickness of 10 μm, in consideration of an expected reduction in film thickness after the post-curing step.

Then, pre-baking was performed on a hot plate at 100° C. for 2 minutes. The film was then exposed to an i-line beam with an i-line stepper, NSR-2205i11, manufactured by Nikon Corporation, to form a pattern. In the pattern formation, a mask for negative pattern or positive pattern was appropriately used according to the used photosensitive resin compositions. The mask had a pattern capable of forming 20 µm holes arranged with a 1:1 ratio lengthwise and breadthwise, and permitted to form a hole pattern of 50 µm to 20 µm holes with 10-µm pitch, 20 µm to 10 µm holes with 5-µm pitch, and 20 µm to 10 µm holes with 1-µm pitch.

Some examples were then subjected to the baking step under conditions shown in Tables 13 to 20.

In the development step, cyclopentanone was used in the case that an organic solvent was used as a developer, while a 2.38% tetramethylammonium hydroxide aqueous solution was used in the case that an alkaline aqueous solution was used as a developer. The organic solvent development was to perform one-time puddling development with cyclopentanone for 1 minute, followed by rinsing with isopropyl alcohol. The alkali development was to perform puddling development with 2.38% tetramethylammonium hydroxide (TMAH) aqueous solution for 1 minute for the appropriate number of times shown in Tables 16 to 20, followed by rinsing with ultrapure water.

The obtained pattern on the substrate was then post-cured with an oven at 250° C. for 2 hours while purging with nitrogen.

Then, each substrate was cut to observe the shape of the obtained hole pattern, and the hole pattern profile was observed with a scanning electron microscope (SEM). A minimum diameter of the opening holes was measured on the post-cured film having a thickness of 10 µm, and the pattern profile was evaluated. Tables 13 to 20 show these results and sensitivity at which a minimum pattern could be formed.

The hole pattern profile was evaluated based on the following criterion. The evaluation results are shown in Tables 13 to 20.

Good: The holes were rectangular or forward tapered (the upper part of the hole is larger than the bottom).

Poor: The holes were reverse tapered (the upper part of the hole is smaller than the bottom), overhanging (the upper part of the hole is protruded), or residues were observed in the hole bottom.

First, Tables 13 to 15 show results of the organic solvent development with the negative photosensitive resin composition (Photosensitive resin compositions 1 to 5, 7 to 15, 17, 18 and Comparative photosensitive resin compositions 5 to 8).

TABLE 13

| | Photosensitive resin composition | Pattern | Post exposure bake | Developer | Development condition | Hole shape | Minimum hole diameter (µm) | Sensitivity (mJ/cm2) |
|---|---|---|---|---|---|---|---|---|
| Example 1 | Photosensitive resin composition 1 | Negative | None | (Organic solvent development) cyclopentanone | Puddling 60 sec one time | Good | 8 | 320 |
| Example 2 | Photosensitive resin composition 2 | Negative | None | (Organic solvent development) cyclopentanone | Puddling 60 sec one time | Good | 8 | 320 |
| Example 3 | Photosensitive resin composition 3 | Negative | None | (Organic solvent development) cyclopentanone | Puddling 60 sec one time | Good | 8 | 300 |
| Example 4 | Photosensitive resin composition 4 | Negative | None | (Organic solvent development) cyclopentanone | Puddling 60 sec one time | Good | 6 | 250 |
| Example 5 | Photosensitive resin composition 5 | Negative | None | (Organic solvent development) cyclopentanone | Puddling 60 sec one time | Good | 7 | 340 |
| Example 6 | Photosensitive resin composition 7 | Negative | None | (Organic solvent development) cyclopentanone | Puddling 60 sec one time | Good | 7 | 340 |
| Example 7 | Photosensitive resin composition 8 | Negative | None | (Organic solvent development) cyclopentanone | Puddling 60 sec one time | Good | 7 | 320 |
| Example 8 | Photosensitive resin composition 9 | Negative | None | (Organic solvent development) cyclopentanone | Puddling 60 sec one time | Good | 8 | 300 |
| Example 9 | Photosensitive resin composition 10 | Negative | None | (Organic solvent development) cyclopentanone | Puddling 60 sec one time | Good | 6 | 320 |
| Example 10 | Photosensitive resin composition 11 | Negative | None | (Organic solvent development) cyclopentanone | Puddling 60 sec one time | Good | 7 | 480 |

TABLE 13-continued

| | Photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Example 11 | Photosensitive resin composition 12 | Negative | None | (Organic solvent development) cyclopentanone | Puddling 60 sec one time | Good | 7 | 500 |
| Example 12 | Photosensitive resin composition 13 | Negative | None | (Organic solvent development) cyclopentanone | Puddling 60 sec one time | Good | 7 | 480 |
| Example 13 | Photosensitive resin composition 14 | Negative | None | (Organic solvent development) cyclopentanone | Puddling 60 sec one time | Good | 7 | 480 |
| Example 14 | Photosensitive resin composition 15 | Negative | None | (Organic solvent development) cyclopentanone | Puddling 60 sec one time | Good | 8 | 520 |
| Example 15 | Photosensitive resin composition 17 | Negative | None | (Organic solvent development) cyclopentanone | Puddling 60 sec one time | Good | 8 | 500 |
| Example 16 | Photosensitive resin composition 18 | Negative | None | (Organic solvent development) cyclopentanone | Puddling 60 sec one time | Good | 8 | 540 |

As shown in Table 13, in the organic solvent development, the inventive negative photosensitive resin composition could give a good pattern profile and a small minimum hole dimension, compared to a final film thickness of 10 μm. It was thus revealed that an aspect ratio of 1 or more could be achieved.

TABLE 14

| | Photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Comparative Example 1 | Comparative photosensitive resin composition 5 | Negative | None | (Organic solvent development) cyclopentanone | Puddling 60 sec one time | Unresolvable Pattern cannot be obtained | | |
| Comparative Example 2 | Comparative photosensitive resin composition 6 | Negative | None | (Organic solvent development) cyclopentanone | Puddling 60 sec one time | Unresolvable Pattern cannot be obtained | | |
| Comparative Example 3 | Comparative photosensitive resin composition 7 | Negative | None | (Organic solvent development) cyclopentanone | Puddling 60 sec one time | Unresolvable Pattern cannot be obtained | | |
| Comparative Example 4 | Comparative photosensitive resin composition 8 | Negative | None | (Organic solvent development) cyclopentanone | Puddling 60 sec one time | Unresolvable Pattern cannot be obtained | | |

In contrast, as shown in Table 14, Comparative photosensitive resin compositions 5 to 8 using the polyimide precursor polymer containing no hexafluoroisopropanol group failed to form a pattern by the organic solvent development with cyclopentanone because the base resins of these photosensitive resin compostions themselves were insoluble in cyclopentanone.

As shown in Table 14, Comparative photosensitive resin compositions 5 to 8 could not form a pattern by the organic solvent development with cyclopentanone. Then, N-methyl-2-pyrrolidone (NMP) was used for organic solvent development of Comparative photosensitive resin compositions 5 to 8. The results are shown in Table 15.

TABLE 15

| | Photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Comparative Example 5 | Comparative photosensitive resin composition 5 | Negative | None | (Organic solvent development) NMP | Puddling 60 sec twice | Poor | 20 | 360 |
| Comparative Example 6 | Comparative photosensitive resin composition 6 | Negative | None | (Organic solvent development) NMP | Puddling 60 sec twice | Poor | 20 | 380 |
| Comparative Example 7 | Comparative photosensitive resin composition 7 | Negative | None | (Organic solvent development) NMP | Puddling 60 sec twice | Poor | 20 | 380 |
| Comparative Example 8 | Comparative photosensitive resin composition 8 | Negative | None | (Organic solvent development) NMP | Puddling 60 sec twice | Poor | 20 | 400 |

As shown in Table 15, Comparative photosensitive resin compositions 5 to 8 using the polyimide precursor polymer containing no hexafluoroisopropanol group could form a pattern by using NMP. However, the pattern dimension was large, and an aspect ratio of 1 or more could not be achieved. In addition, overhanging profile was observed on many patterns, and thus the pattern profile was poor. The overhanging profile is supposed to be caused by swelling of the pattern during development.

Next, Tables 16 and 17 show results of the alkaline aqueous solution development with the negative photosensitive resin composition (Photosensitive resin compositions 6, 7, 9 to 14, 16, 17 and Comparative photosensitive resin compositions 5 to 8).

TABLE 16

| | Photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Example 17 | Photosensitive resin composition 6 | Negative | None | (Alkali development) 2.38% TMAH | Puddling 60 sec twice | Good | 6 | 360 |
| Example 18 | Photosensitive resin composition 7 | Negative | None | (Alkali development) 2.38% TMAH | Puddling 60 sec twice | Good | 6 | 380 |
| Example 19 | Photosensitive resin composition 9 | Negative | None | (Alkali development) 2.38% TMAH | Puddling 60 sec three times | Good | 6 | 400 |
| Example 20 | Photosensitive resin composition 10 | Negative | None | (Alkali development) 2.38% TMAH | Puddling 60 sec three times | Good | 6 | 400 |
| Example 21 | Photosensitive resin composition 11 | Negative | 100° C. 90 sec | (Alkali development) 2.38% TMAH | Puddling 60 sec one time | Good | 6 | 440 |

TABLE 16-continued

|  | Photosensitive resin composition | Pattern | Post exposure bake | Developer | Development condition | Hole shape | Minimum hole diameter (µm) | Sensitivity (mJ/cm2) |
|---|---|---|---|---|---|---|---|---|
| Example 22 | Photosensitive resin composition 12 | Negative | 100° C. 90 sec | (Alkali development) 2.38% TMAH | Puddling 60 sec one time | Good | 6 | 460 |
| Example 23 | Photosensitive resin composition 13 | Negative | 100° C. 90 sec | (Alkali development) 2.38% TMAH | Puddling 60 sec one time | Good | 6 | 480 |
| Example 24 | Photosensitive resin composition 14 | Negative | 100° C. 90 sec | (Alkali development) 2.38% TMAH | Puddling 60 sec one time | Good | 7 | 480 |
| Example 25 | Photosensitive resin composition 16 | Negative | 100° C. 90 sec | (Alkali development) 2.38% TMAH | Puddling 60 sec twice | Good | 7 | 500 |
| Example 26 | Photosensitive resin composition 17 | Negative | 100° C. 90 sec | (Alkali development) 2.38% TMAH | Puddling 60 sec twice | Good | 7 | 480 |

As shown in Table 16, also in the development with alkaline developer, the inventive negative photosensitive resin composition could give a good pattern profile and a small minimum hole dimension, compared to a final film thickness of 10 µm. It was thus revealed that an aspect ratio of 1 or more could be achieved.

TABLE 17

|  | Photosensitive resin composition | Pattern | Post exposure bake | Developer | Development condition | Hole shape | Minimum hole diameter (µm) | Sensitivity (mJ/cm2) |
|---|---|---|---|---|---|---|---|---|
| Comparative Example 9 | Comparative photosensitive resin composition 5 | Negative | None | (Alkali development) 2.38% TMAH | Puddling 60 sec three times | Opening failure Residue is observed at a large space | | |
| Comparative Example 10 | Comparative photosensitive resin composition 6 | Negative | None | (Alkali development) 2.38% TMAH | Puddling 60 sec three times | Opening failure Residue is observed at a large space | | |
| Comparative Example 11 | Comparative photosensitive resin composition 7 | Negative | None | (Alkali development) 2.38% TMAH | Puddling 60 sec three times | Opening failure Residue is observed at a large space | | |
| Comparative Example 12 | Comparative photosensitive resin composition 8 | Negative | None | (Alkali development) 2.38% TMAH | Puddling 60 sec three times | Opening failure Residue is observed at a large space | | |

In contrast, Comparative photosensitive resin compositions 5 to 8, which are negative photosensitive resin compositions using the polyimide precursor polymer containing no hexafluoroisopropanol group, caused opening failure and residues at a space by patterning with an alkaline developer, as shown in Comparative Examples 9 to 12 of Table 17. The reason is that the base resins used in Comparative photosensitive resin compositions 5 to 8 had no hexafluoroisopropanol group, i.e., no alkali-soluble organic group, and thus the alkali development was difficult.

Next, Tables 18 to 20 show results of patterning with the positive photosensitive resin composition (Photosensitive resin compositions 19 to 37 and Comparative photosensitive resin compositions 13 to 16).

TABLE 18

| | Photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Example 27 | Photosensitive resin composition 19 | Positive | None | (Alkali development) 2.38% TMAH | Puddling 60 sec one time | Good | 6 | 440 |
| Example 28 | Photosensitive resin composition 20 | Positive | None | (Alkali development) 2.38% TMAH | Puddling 60 sec one time | Good | 6 | 460 |
| Example 29 | Photosensitive resin composition 21 | Positive | None | (Alkali development) 2.38% TMAH | Puddling 60 sec one time | Good | 6 | 440 |
| Example 30 | Photosensitive resin composition 22 | Positive | None | (Alkali development) 2.38% TMAH | Puddling 60 sec one time | Good | 6 | 480 |
| Example 31 | Photosensitive resin composition 23 | Positive | None | (Alkali development) 2.38% TMAH | Puddling 60 sec one time | Good | 6 | 480 |
| Example 32 | Photosensitive resin composition 24 | Positive | None | (Alkali development) 2.38% TMAH | Puddling 60 sec one time | Good | 6 | 460 |
| Example 33 | Photosensitive resin composition 25 | Positive | None | (Alkali development) 2.38% TMAH | Puddling 60 sec one time | Good | 6 | 440 |
| Example 34 | Photosensitive resin composition 26 | Positive | None | (Alkali development) 2.38% TMAH | Puddling 60 sec one time | Good | 6 | 460 |
| Example 35 | Photosensitive resin composition 27 | Positive | None | (Alkali development) 2.38% TMAH | Puddling 60 sec one time | Good | 6 | 440 |
| Example 36 | Photosensitive resin composition 28 | Positive | None | (Alkali development) 2.38% TMAH | Puddling 60 sec one time | Good | 6 | 460 |
| Example 37 | Photosensitive resin composition 29 | Positive | None | (Alkali development) 2.38% TMAH | Puddling 60 sec one time | Good | 6 | 440 |
| Example 38 | Photosensitive resin composition 30 | Positive | None | (Alkali development) 2.38% TMAH | Puddling 60 sec one time | Good | 6 | 480 |
| Example 39 | Photosensitive resin composition 31 | Positive | None | (Alkali development) 2.38% TMAH | Puddling 60 sec one time | Good | 6 | 440 |

TABLE 19

| | Photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Example 40 | Photosensitive resin composition 36 | Positive | None | (Alkali development) 2.38% TMAH | Puddling 60 sec one time | Good | 6 | 480 |
| Example 41 | Photosensitive resin composition 37 | Positive | None | (Alkali development) 2.38% TMAH | Puddling 60 sec one time | Good | 6 | 500 |
| Example 42 | Photosensitive resin composition 32 | Positive | None | (Alkali development) 2.38% TMAH | Puddling 60 sec one time | Good | 6 | 500 |
| Example 43 | Photosensitive resin composition 33 | Positive | None | (Alkali development) 2.38% TMAH | Puddling 60 sec one time | Good | 6 | 500 |
| Example 44 | Photosensitive resin composition 34 | Positive | None | (Alkali development) 2.38% TMAH | Puddling 60 sec one time | Good | 6 | 500 |
| Example 45 | Photosensitive resin composition 35 | Positive | None | (Alkali development) 2.38% TMAH | Puddling 60 sec one time | Good | 6 | 500 |

As shown in Tables 18 and 19, in the development with alkaline developer, the inventive positive photosensitive resin composition could give a good pattern profile and a small minimum hole dimension, compared to a final film thickness of 10 μM. It was thus revealed that an aspect ratio of 1 or more could be achieved.

the base resins used in Comparative photosensitive resin compositions 13 to 16 had no hexafluoroisopropanol group, i.e., no alkali-soluble organic group, and thus the alkali development was difficult.

It should be noted that the present invention is not limited to the foregoing embodiment. The embodiment is just an

TABLE 20

| | Photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Comparative Example 13 | Comparative photosensitive resin composition 13 | Positive | None | (Alkali development) 2.38% TMAH | Puddling 60 sec three times | Poor | 20 | 500 |
| Comparative Example 14 | Comparative photosensitive resin composition 14 | Positive | None | (Alkali development) 2.38% TMAH | Puddling 60 sec three times | Poor | 20 | 500 |
| Comparative Example 15 | Comparative photosensitive resin composition 15 | Positive | None | (Alkali development) 2.38% TMAH | Puddling 60 sec three times | Poor | 20 | 500 |
| Comparative Example 16 | Comparative photosensitive resin composition 16 | Positive | None | (Alkali development) 2.38% TMAH | Puddling 60 sec three times | Poor | 20 | 500 |

In contrast, Comparative photosensitive resin compositions 13 to 16, which are positive photosensitive resin compositions using the polyimide precursor polymer containing no hexafluoroisopropanol group, by patterning with an alkaline developer, could form a large pattern of 20 μm, but were difficult to achieve an aspect ratio more than 1, and residues were observed in the hole bottom even when the number of development was increased, as shown in Comparative Examples 13 to 16 of Table 20. The reason is that exemplification, and any examples that have substantially the same feature and demonstrate the same functions and effects as those in the technical concept described in claims of the present invention are included in the technical scope of the present invention.

What is claimed is:
1. A tetracarboxylic acid diester compound shown by the following general formula (1),

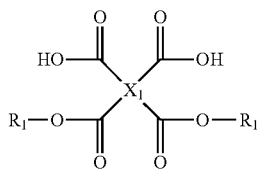
(1)

wherein $X_1$ represents a tetravalent organic group; and $R_1$ represents a group shown by the following general formula (2),

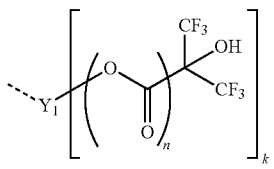
(2)

wherein the dotted line represents a bond; $Y_1$ represents a divalent organic group selected from linear or branched alkylene groups having 1 to 6 carbon atoms; "k" represents 1; and "n" represents 0 or 1.

2. The tetracarboxylic acid diester compound according to claim 1, wherein $R_1$ in the general formula (1) is an organic group selected from groups shown by the following formulae (3), (4), and (5),

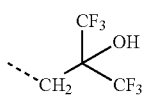
(3)

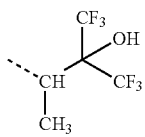
(4)

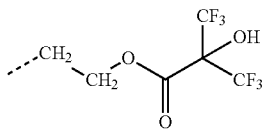
(5)

wherein the dotted line represents a bond.

3. A polyimide precursor polymer comprising a structural unit shown by the following general formula (6),

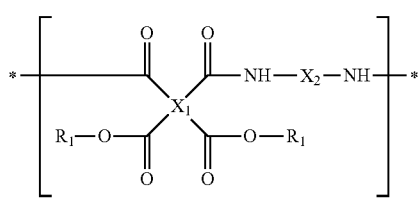
(6)

wherein $X_1$ represents a tetravalent organic group; $X_2$ represents a divalent organic group; and $R_1$ represents a group shown by the following general formula (2),

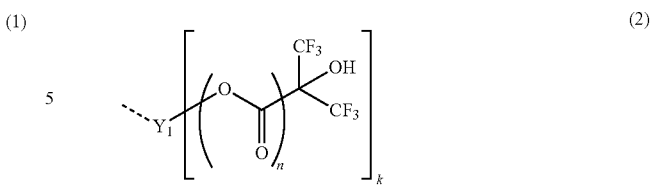
(2)

wherein the dotted line represents a bond; $Y_1$ represents an organic group with a valency of k+1; "k" represents 1 or 2; and "n" represents 0 or 1.

4. The polyimide precursor polymer according to claim 3, further comprising a structural unit shown by the following general formula (7),

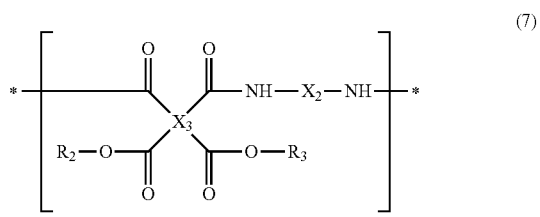
(7)

wherein $X_2$ has the same meaning as above; $X_3$ represents a tetravalent organic group that is the same as or different from $X_1$; and $R_2$ and $R_3$ independently represent a hydrogen atom, a linear, branched, or cyclic alkyl group having 1 to 6 carbon atoms, or an organic group shown by the following general formula (8), provided that at least one of $R_2$ and $R_3$ is an organic group shown by the general formula (8),

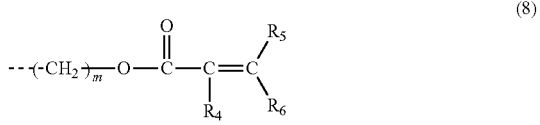
(8)

wherein the dotted line represents a bond; $R_4$ represents a hydrogen atom or an organic group having 1 to 3 carbon atoms; $R_5$ and $R_6$ independently represent a hydrogen atom or an organic group having 1 to 3 carbon atoms; and "m" represents an integer of 2 to 10.

5. A method for producing the polyimide precursor polymer according to claim 3, comprising reacting a tetracarboxylic acid diester compound shown by the following general formula (1) with a diamine shown by the following general formula (9),

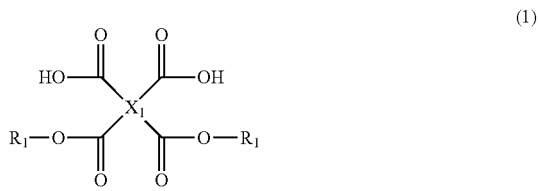
(1)

wherein $X_1$ and $R_1$ have the same meanings as above, $$H_2N-X_2-NH_2 \quad (9)$$

wherein $X_2$ has the same meaning as above.

6. A method for producing the polyimide precursor polymer according to claim 4, comprising
reacting a tetracarboxylic acid diester compound shown by the following general formula (1) with a diamine shown by the following general formula (9) and a tetracarboxylic acid diester compound shown by the following general formula (10),

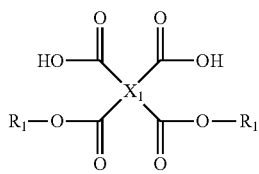
(1)

wherein $X_1$ and $R_1$ have the same meanings as above, $$H_2N-X_2-NH_2 \quad (9)$$

wherein $X_2$ has the same meaning as above,

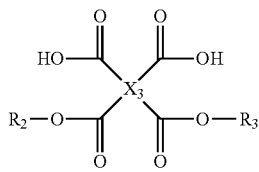
(10)

wherein $X_3$, $R_2$, and $R_3$ have the same meanings as above.

7. A negative photosensitive resin composition comprising:
(A) the polyimide precursor polymer according to claim 4;
(B) a photo-radical initiator; and
(D) a solvent.

8. A negative photosensitive resin composition comprising:
(A') the polyimide precursor polymer according to claim 3;
(B) a photo-radical initiator;
(C) a crosslinking agent having two or more photo-polymerizable unsaturated bonding groups per molecule; and
(D) a solvent.

9. A negative photosensitive resin composition comprising:
(A') the polyimide precursor polymer according to claim 4;
(B) a photo-radical initiator;
(C) a crosslinking agent having two or more photo-polymerizable unsaturated bonding groups per molecule; and
(D) a solvent.

10. A negative photosensitive resin composition comprising:
(A') the polyimide precursor polymer according to claim 3;
(B') a photo acid generator;
(C') one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

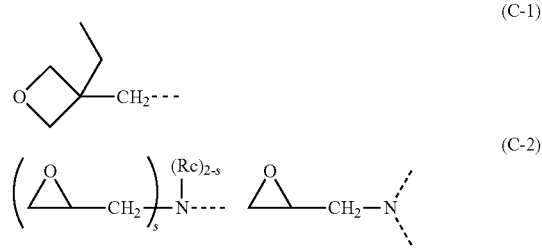

wherein the dotted line represents a bond, Rc represents a linear, branched, or cyclic alkyl group having 1 to 6 carbon atoms, and "s" represents 1 or 2; and
(D) a solvent.

11. A negative photosensitive resin composition comprising:
(A') the polyimide precursor polymer according to claim 4;
(B') a photo acid generator;
(C') one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

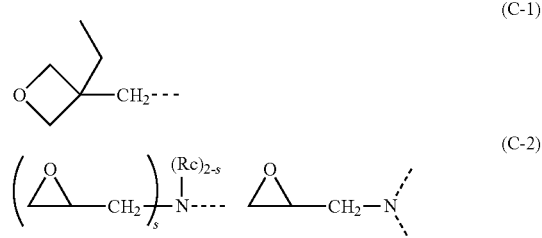

wherein the dotted line represents a bond, Rc represents a linear, branched, or cyclic alkyl group having 1 to 6 carbon atoms, and "s" represents 1 or 2; and
(D) a solvent.

12. A positive photosensitive resin composition comprising:
(A') the polyimide precursor polymer according to claim 3;
(B") a compound having a quinonediazide structure for serving as a photosensitive agent capable of generating an acid by light and increasing a dissolution rate in an alkaline aqueous solution;
(C") one or two or more crosslinking agents selected from a crosslinking agent having two or more photo-polymerizable unsaturated bonding groups per molecule, an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

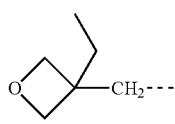
(C-1)

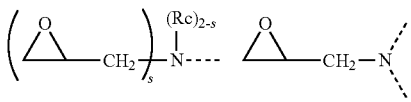
(C-2)

wherein the dotted line represents a bond, Rc represents a linear, branched, or cyclic alkyl group having 1 to 6 carbon atoms, and "s" represents 1 or 2; and
(D) a solvent.

13. A positive photosensitive resin composition comprising:
(A') the polyimide precursor polymer according to claim 4;
(B") a compound having a quinonediazide structure for serving as a photosensitive agent capable of generating an acid by light and increasing a dissolution rate in an alkaline aqueous solution;
(C") one or two or more crosslinking agents selected from a crosslinking agent having two or more photo-polymerizable unsaturated bonding groups per molecule, an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms bonded to a glycidyl group as shown by the following formula (C-2),

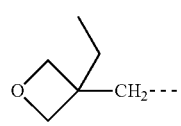
(C-1)

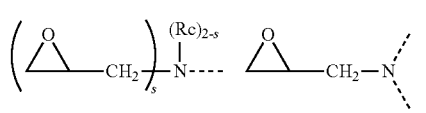
(C-2)

wherein the dotted line represents a bond, Rc represents a linear, branched, or cyclic alkyl group having 1 to 6 carbon atoms, and "s" represents 1 or 2; and
(D) a solvent.

14. The positive photosensitive resin composition according to claim 12, further comprising
(E) a compound capable of generating an acid or a radical by heat.

15. A patterning process comprising:
(1) applying the negative photosensitive resin composition according to claim 7 onto a substrate to form a photosensitive material film;
(2) exposing the photosensitive material film to a high energy beam having a wavelength of 1.90 to 500 nm or an electron beam via a photomask after a heat treatment; and
(3) performing development with a developer of an alkaline aqueous solution or an organic solvent.

16. The patterning process according to claim 15, further comprising performing post-exposure bake between the exposing step and the development step.

17. A patterning process comprising:
(I) applying the positive photosensitive resin composition according to claim 12 onto a substrate to form a photosensitive material film;
(II) exposing the photosensitive material film to a high energy beam having a wavelength of 190 to 500 nm or an electron beam via a photomask after a heat treatment; and
(III) performing development with a developer of an alkaline aqueous solution.

18. A method for forming a cured film, comprising baking a film having a pattern formed by the patterning process according to claim 15 at 100 to 300° C. and post-curing the film.

* * * * *